United States Patent
Kearney et al.

(10) Patent No.: US 11,193,935 B2
(45) Date of Patent: *Dec. 7, 2021

(54) COMPOSITIONS, METHODS AND KITS FOR DIAGNOSIS OF LUNG CANCER

(71) Applicant: Biodesix, Inc., Boulder, CO (US)

(72) Inventors: Paul Edward Kearney, Seattle, WA (US); Kenneth Charles Fang, San Francisco, CA (US); Xiao-Jun Li, Bellevue, WA (US); Clive Hayward, Seattle, WA (US)

(73) Assignee: Biodesix, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/680,656

(22) Filed: Aug. 18, 2017

(65) Prior Publication Data

US 2018/0011099 A1    Jan. 11, 2018

Related U.S. Application Data

(63) Continuation of application No. 15/041,775, filed on Feb. 11, 2016, now abandoned, which is a continuation of application No. 14/341,245, filed on Jul. 25, 2014, now Pat. No. 9,297,805.

(60) Provisional application No. 61/858,760, filed on Jul. 26, 2013.

(51) Int. Cl.
*G01N 33/574* (2006.01)
*G16B 20/00* (2019.01)

(52) U.S. Cl.
CPC .  *G01N 33/57423* (2013.01); *G01N 33/57488* (2013.01); *G01N 2333/46* (2013.01); *G01N 2333/78* (2013.01); *G01N 2333/785* (2013.01); *G01N 2333/96433* (2013.01); *G01N 2333/988* (2013.01); *G16B 20/00* (2019.02)

(58) Field of Classification Search
CPC .............................................. G01N 33/57423
See application file for complete search history.

(56) References Cited

U.S. PATENT DOCUMENTS

| | | |
|---|---|---|
| 7,183,188 B2 | 2/2007 | Kronke et al. |
| 2006/0257857 A1 | 11/2006 | Keene et al. |
| 2007/0099251 A1 | 5/2007 | Zhang et al. |
| 2007/0111322 A1 | 5/2007 | Yang |
| 2007/0128598 A1 | 6/2007 | Boender |
| 2007/0202539 A1 | 8/2007 | Aebersold et al. |
| 2007/0269895 A1 | 11/2007 | Aebersold et al. |
| 2009/0317392 A1 | 12/2009 | Nakamura et al. |
| 2010/0093108 A1 | 4/2010 | Khattar et al. |
| 2010/0184034 A1 | 7/2010 | Bankaitis-Davis et al. |
| 2010/0279382 A1 | 11/2010 | Aebersold et al. |
| 2012/0142558 A1 | 6/2012 | Li et al. |
| 2013/0230877 A1 | 9/2013 | Kearney et al. |

FOREIGN PATENT DOCUMENTS

| | | |
|---|---|---|
| WO | WO-2011085163 A2 | 7/2011 |
| WO | WO-2012075042 A1 | 6/2012 |
| WO | WO-2013/096845 A2 | 6/2013 |
| WO | WO-2013/096862 A2 | 6/2013 |

OTHER PUBLICATIONS

Bouchal et al (Journal of Proteome Research, 2009, 8:362-373).*
Ricolleau et al (Proteomics, 2006, 6:1963-1975).*
Kitada et al (World Journal of Surgical Oncology, 2011, 9:124; internet pp. 1-5).*
Bouchal et al (Journal of Proteome Research, 2009, 8:362-373) Supplemental Table 2.*
Robin et al (Expert Review of Proteomics, 2009, 6:675-689).*
Walsh et al (Expert Reviews in Molecular Medicine, 2010, 12:e30, internet pp. 1-28).*
Lange et al (Molecular Systems Biology; 2008; 4:222, internet pp. 1-14).*
"Evolution of Translational Omics: Lessons Learned and the Path FoNNard." *Committee on the Review of Omics-Based Tests for Predicting Patient Outcomes in Clinical Trials.* Micheel et al., eds. (2012):xv-338.
Addona et al. "A Pipeline that Integrates the Discovery and Verification of Plasma Protein Biomarkers Reveals Candidate Markers for Cardiovascular Disease." *Nat. Biotechnol.* 29.7(2011):635-643.
Addona et al. "Multi-Site Assessment of the Precision and Reproducibility of Multiple Reaction Monitoring-Based Measurements of Proteins in Plasma." *Nat. Biotechnol.* 27.7(2009):633-641.
Albert et al. "Evaluation of the Solitary Pulmonary Nodule." *Am. Fam. Physician.* 80.8(2009):827-831.
Bigbee et al. "A Multiplexed Serum Biomarker Immunoassay Panel Discriminates Clinical Lung Cancer Patients from High-Risk Individuals Found to be Cancer-Free by CT Scanning." *J. Thorac Oncol.* 7.4(2012):698-708.
Brusniak et al. "Corra: Computational Framework and Tools for LC-MS Discovery and Targeted Mass Spectrometry-Based Proteomics." *BMC Bioinformatics.* 9(2008):542.
Carozzi et al. "Molecular Profile in Body Fluids in Subjects Enrolled in a Randomised Trial for Lung Cancer Screening: Perspectives of Integrated Strategies for Early Diagnosis." *Lung Cancer.* 68.2(2010):2216-221.

(Continued)

*Primary Examiner* — Laura B Goddard
(74) *Attorney, Agent, or Firm* — Foley Hoag LLP

(57) ABSTRACT

The present invention provides methods for identifying biomarker proteins that exhibit differential expression in subjects with a first lung condition versus healthy subjects or subjects with a second lung condition. The present invention also provides compositions comprising these biomarker proteins and methods of using these biomarker proteins or panels thereof to diagnose, classify, and monitor various lung conditions. The methods and compositions provided herein may be used to diagnose or classify a subject as having lung cancer or a non-cancerous condition, and to distinguish between different types of cancer (e.g., malignant versus benign, SCLC versus NSCLC).

18 Claims, 5 Drawing Sheets

Specification includes a Sequence Listing.

(56) References Cited

OTHER PUBLICATIONS

Chapman et al. "EarlyCDT®-Lung Test: Improved Clinical Utility Through Additional Autoantibody Assays." *Tumor Biol.* 33.5(2012):1319-1326.
Cima et al. "Cancer Genetics-Guided Discovery of Serum Biomarker Signatures for Diagnosis and Prognosis of Prostate Cancer." *PNAS.* 108.8(2011):3342-3347.
Desiere et al. "The PeptideAtlas Project." *Nucleic Acids Res.* 34(2006):D655-D658.
Farrah et al. "A High-Confidence Human Plasma Proteome Reference Set with Estimated Concentrations in PeptideAtlas." *Mol. Cell. Proteomics.* 10.9(2011):M110.006353.
Fracchia A. et al., "A Comparative Study on Ferritin Concentration in Serum and Bilateral Bronchoalveolar Lavage Fluid of Patients with Peripheral Lung Cancer versus Control Subjects", *Oncology,* (1999), vol. 56, p. 181-188.
Gould et al. "Evaluation of Patients with Pulmonary Nodules: When is it Lung Cancer?" *Chest.* 132.53(2007):1085-1305.
Halliwell et al. "Oxidative Stress and Cancer: Have We Moved Forward?" *Biochem. J.* 401.1(2007):1-11.
Hanash et al. "Emerging Molecular Biomarkers—Blood-Based Strategies to Detect and Monitor Cancer." *Nat. Rev. Clin. Oncol.* 8.3(2011):142-150.
Hassanein et al. "Advances in Proteomic Strategies Toward the Early Detection of Lung Cancer." *Proc. Am. Thorac. Soc.* 8.2(2011):183-188.
Hennessey et al. "Serum MicroRNA Biomarkers for Detection of Non-Small Cell Lung Cancer." *PLoS One.* 7.2(2012):e32307.
Henschke et al. "CT Screening for Lung Cancer: Suspiciousness of Nodules According to Size on Baseline Scans." *Radiology.* 231.1(2004):164-168.
Henschke et al. "Early Lung Cancer Action Project: Overall Design and Findings from Baseline Screenings." *Lancet.* 354.9173(1999):99-105.
Huttenhain et al. "Reproducible Quantification of Cancer-Associated Proteins in Body Fluids using Targeted Proteomics." *Sci. Transl. Med.* 4.142(2012):149ra194.
International Search Report for International Application No. PCT/US2014/048260 dated Dec. 23, 2014.
Kearney et al. "Protein Identification and Peptide Expression Resolver: Harmonizing Protein Identification with Protein Expression Data." *J. Proteome Res.* 7.1(2008):234-244.
Kitteringham et al. "Multiple Reaction Monitoring for Quantitative Biomarker Analysis in Proteomics and Metabolomics." *J. Chromatogr. B.* 877.13(2009):12291239.
Lam et al. "EarlyCDT-Lung: An Immunobiomarker Test as an Aid to Early Detection of Lung Cancer." *Cancer Prev. Res.* 4.7(2011):1126-1134.
Lehtio et al. "Lung Cancer Proteomics, Clinical and Technological Considerations." *J. Proteomics.* 73.10(2010):1851-1863.
Lombardi et al. Clinical Significance of a Multiple BiomarkerAssay in Patients with Lung Cancer. *Chest.* 97.3(1990):639-644.
MacMahon et al. "Guidelines for Management of Small Pulmonary Nodules Detected on CT Scans: A Statement from the Fleischner Society." *Radiology.* 237.2(2005):395-400.
Makawita et al. "The Bottleneck in the Cancer Biomarker Pipeline and Protein Quantification through Mass Spectrometry-Based Approaches: Current Strategies for Candidate Verification." *Clin. Chem.* 56.2(2010):212-222.
McClish. "Analyzing a Portion of the ROC Curve." *Med. Decis. Making.* 9.3(1989):190-195.
Miller et al. "Minimizing Unintended Consequences of Detecting Lung Nodules by Computed Tomography." *Am. J. Resp. Crit. Care Med.* 178.9(2008):891-892.
Milman et al., "The serum ferritin concentration is a significant prognostic indicator of survival in primary lung cancer", *Oncology Reports,* (2002), vol. 9, No. 1, p. 193198.
Ocak et al. "Mass Spectrometry-Based Proteomic Profiling of Lung Cancer." *Proc. Am. Thorac. Soc.* 6.2(2009):159-170.
Omenn et al. "Overview of the HUPO Plasma Proteome Project: Results from the Pilot Phase with 35 Collaborating Laboratories and Multiple Analytical Groups, Generating a Core Dataset of 3020 Proteins and a Publicly-Available Database." *Proteomics.* 5.13(2005):3226-3245.
Ost et al. "Decision Making in Patients with Pulmonary Nodules." *Am. J. Respir. Crit. Care Med.* 185.4(2012):363-372.
Ostroff et al. "Unlocking Biomarker Discovery: Large Scale Application of Aptamer Proteomic Technology for Early Detection of Lung Cancer." *PLoS One.* 5.12(2010):e15003.
Ozaki Y. et al., "Expression and Immunogenicity of a Tumor-Associated Antigen, 90K/Mac-2 Binding Protein, in Lung Carcinoma", *Cancer,* (2002), vol. 95, p. 19541962.
Pecot et al. "Added Value of a Serum Proteomic Signature in the Diagnostic Evaluation of Lung Nodules." *Cancer Epidemiol. Biomarkers Prev.* 21.5(2012):786792.
Perkins et al. "Probability-Based Protein Identification by Searching Sequence Databases Using Mass Spectrometry Data." *Electrophoresis.* 20.18(1999):3551-3567.
Picotti et al. "High-Throughput Generation of Selected Reaction-Monitoring Assays for Proteins and Proteomes." *Nat. Meth.* 7.1(2010):43-46.
Polanski et al. "A List of Candidate Cancer Biomarkers for Targeted Proteomics." *Biomarker Insights.* 1(2007):1-48.
Price et al. "Highly Accurate Two-Gene Classifier for Differentiating Gastrointestinal Stromal Tumors and Leiomyosarcomas." *PNAS.* 104.9(2007):3414-3419.
Qin et al. "SRM Targeted Proteomics in Seach for Biomarkers of HCV-Induced Progression of Fibrosis to Cirrhosis in HALT-C Patients." *Proteomics.* 12.8(2012):1244-1252.
Radulovic et al. "Informatics Platform for Global Proteomic Profiling and Biomarker Discovery Using Liquid Chromatography-Tandem Mass Spectrometry." *Mol. Cell. Proteins.* 3.10(2004):984-997.
Reiter et al. "mProphet: Automated Data Processing and Statistical Validation for Large-Scale SRM Exgeriments." *Nat. Meth.* 8.5(2011):430-435.
Rho J. et al. "Glycoproteomic Analysis of Human Lung Adenocarcinomas Using Glycoarrays and Tandem Mass Spectrometry: Differential Expression and Glycosylation Patterns of Vimentin and Fetuin A Isoforms." *Protein J.* 28.34(2009):148-160.
Rom et al. "Identification of an Autoantibody Panel to Separate Lung Cancer from Smokers and Nonsmokers." *BMC Cancer.* 10(2010):234.
Schauer et al. "National Council on Radiation Protection and Measurements Report Shows Substantial Medical Exgosure Increase." *Radio!.* 253.2(2009):293-296.
States et al. "Challenges in Deriving High-Confidence Protein Identifications from Data Gathered by a HUPO Plasma Proteome Collaborative Study." *Nat. Biotechnol.* 24.3(2006):333-338.
Stern et al. "Nationwide Evaluation of X-Ray Trends (NEXT) Jan. 2000 Survey of Patient Radiation Exposure from Computed Tomographic (CT) Examinations in the United States." *87th Scientific Assembly and Annual Meeting of the Radiological Society of North America, Chicago,* Nov. 25-30, 2001.
Swensen et al., "Lung Cancer Screening with CT: Mayo Clinic Experience", *Radiology,* (2003), vol. 226, p. 756-761.
Taguchi et al. "Unleashing the Power of Proteomics to Develop Blood-Based Cancer Markers." *Clin. Chem.* 59(2013):1.
Teutsch et al. "The Evaluation of Genomic Applications in Practice and Prevention (EGAPP) Initiative: Methods of the EGAPP Working Groug." *Genet. Med.* 11.1(2009):3-14.
Tockman M. et al., "Considerations in Bringing a Cancer Biomarker to Clinical Applications", *Cancer Research,* (1992), vol. 52, p. 2711s-2718s.
Ueda K. et al., "A Comprehensive Peptidome Profiling Technology for the Identification of Early Detection Biomarkers for Lung Adenocarcinoma", *PloS One,* (Apr. 12, 2011), vol. 6, issue 4, e18567, p. 1-12.
Walser et al. "Smoking and Lung Cancer: The Role of Inflammation." *Proc. Am. Thorac. Soc.* 5.8(2008):811-815.

(56) References Cited

OTHER PUBLICATIONS

Wang et al. "The evolving role of mass spectrometry in cancer biomarker discovery", *Cancer Biology and Therapy*, (2009), vol. 8, p. 1083-1094.
Wei et al. "Primary Tumor Xenografts of Human Lung Adeno and Squamous Cell Carcinoma Express Distinct Proteomic Signatures", *Journal of Proteome Research*, (2011), vol. 10, p. 161-174, Qublished online Sep. 3, 2010.
Whiteaker et al. "A Targeted Proteomics-Based Pipeline for Verification of Biomarkers in Plasma." *Nat. Biotechnol.* 29.7(2011):625-634.
Wiener et al. "Population-Based Risk for Complications after Transthoracic Needle Lung Biopsy of a Pulmonary Nodule: An Analysis of Discharge Records." *Ann. Int. Med.* 155.3(2011):137-144.
Yildiz et al. "Diagnostic Accuracy of MALDI Mass Spectrometic Analysis of Unfractionated Serum in Lung Cancer." *J. Thorac. Oncol.* 2.10(2007):893-901.
Zeng et al. "Lung Cancer Serum Biomarker Discovery Using Glycoprotein Capture and Liquid Chromatography Mass Spectrometry." *J. Proteome Res.* 9.12(2010):64406449.

\* cited by examiner

COMPOSITIONS, METHODS AND KITS FOR DIAGNOSIS OF LUNG CANCER

CROSS-REFERENCE TO RELATED APPLICATIONS

This application is a continuation application of U.S. application Ser. No. 15/041,775, filed on Feb. 11, 2016, which is a continuation application of U.S. application Ser. No. 14/341,245, filed on Jul. 25, 2014, now U.S. Pat. No. 9,297,805, which claims priority to, and the benefit of, U.S. Ser. No. 61/858,760, filed on Jul. 26, 2013, the entire contents of each of which are incorporated herein by reference in their entireties.

INCORPORATION-BY-REFERENCE OF SEQUENCE LISTING

The contents of the text file named "IDIA-009 Sequence listing_ST25.txt", which was created on Sep. 29, 2014, and is 108 KB in size, are hereby incorporated by reference in their entireties.

BACKGROUND OF THE INVENTION

Lung conditions and particularly lung cancer present significant diagnostic challenges. In many asymptomatic patients, radiological screens such as computed tomography (CT) scanning are a first step in the diagnostic paradigm. Pulmonary nodules (PNs) or indeterminate nodules are located in the lung and are often discovered during screening of both high risk patients or incidentally. The number of PNs identified is expected to rise due to increased numbers of patients with access to health care, the rapid adoption of screening techniques and an aging population. It is estimated that over 3 million PNs are identified annually in the US. Although the majority of PNs are benign, some are malignant leading to additional interventions. For patients considered low risk for malignant nodules, current medical practice dictates scans every three to six months for at least two years to monitor for lung cancer. The time period between identification of a PN and diagnosis is a time of medical surveillance or "watchful waiting" and may induce stress on the patient and lead to significant risk and expense due to repeated imaging studies. If a biopsy is performed on a patient who is found to have a benign nodule, the costs and potential for harm to the patient increase unnecessarily. Major surgery is indicated in order to excise a specimen for tissue biopsy and diagnosis. All of these procedures are associated with risk to the patient including: illness, injury and death as well as high economic costs.

Frequently, PNs cannot be biopsied to determine if they are benign or malignant due to their size and/or location in the lung. However, PNs are connected to the circulatory system, and so if malignant, protein markers of cancer can enter the blood and provide a signal for determining if a PN is malignant or not.

Diagnostic methods that can replace or complement current diagnostic methods for patients presenting with PNs are needed to improve diagnostics, reduce costs and minimize invasive procedures and complications to patients.

SUMMARY OF THE INVENTION

The present invention provides novel compositions, methods and kits for identifying protein markers to identify, diagnose, classify and monitor lung conditions, particularly lung cancer. The present invention uses a multiplexed assay to distinguish benign pulmonary nodules from malignant pulmonary nodules to classify patients with or without lung cancer. The present invention may be used in patients who present with symptoms of lung cancer, but do not have pulmonary nodules.

The present invention provides a method of determining the likelihood that a lung condition in a subject is cancer by measuring the abundance of proteins in a sample obtained from the subject; calculating a probability of cancer score based on the protein abundance and a protein-protein (mathematical) interaction between FRIL_HUMAN and COIA1_HUMAN; and ruling out cancer for the subject if the score is lower than a pre-determined score. When cancer is ruled out, the subject does not receive a treatment protocol. Treatment protocols include for example pulmonary function test (PFT), pulmonary imaging, a biopsy, a surgery, chemotherapy, a radiotherapy, or any combination thereof. In some embodiments, the imaging is an x-ray, a chest computed tomography (CT) scan, or a positron emission tomography (PET) scan.

The present invention further provides a method of determining the likelihood of the presence of a lung condition in a subject by measuring the abundance of proteins in a sample obtained from the subject, calculating a probability of cancer score based on the protein abundance and a protein-protein (mathematical) interaction between FRIL_HUMAN and COIA1_HUMAN; and concluding the presence of said lung condition if the score is equal or greater than a pre-determined score. The pre-determined score can be determined by scoring a plurality of subjects as part of a reference population. The lung condition is lung cancer such as for example, non-small cell lung cancer (NSCLC). The subject is at risk of developing lung cancer. The likelihood of cancer can be determined by the sensitivity, specificity, negative predictive value or positive predictive value associated with the score.

The present invention also provides methods of determining that a lung condition in a subject is cancer comprising assessing the expression of a plurality of proteins comprising determining the protein expression level of at least each of ALDOA_HUMAN, FRIL_HUMAN, LG3BP_HUMAN, TSP1_HUMAN and COIA1_HUMAN from a biological sample obtained from the subject; calculating a score from the protein expression of at least each of ALDOA_HUMAN, FRIL_HUMAN, LG3BP_HUMAN, TSP1_HUMAN and COIA1_HUMAN from the biological sample determined in the preceding step; and comparing the score from the biological sample to a plurality of scores obtained from a reference population, wherein the comparison provides a determination that the lung condition is not cancer.

The determination that a lung condition is not cancer can include assessing the expression of a plurality of proteins to determine the protein expression level of at least each of ALDOA_HUMAN, FRIL_HUMAN, LG3BP_HUMAN, TSP1_HUMAN, and COIA1_HUMAN obtained from a biological sample from a subject. A score is calculated from these assessments and this score is further compared with a plurality of scores obtained from a reference population, wherein the comparison provides a determination that the lung condition is not cancer. The method can also include determining an interaction between FRIL_HUMAN AND COIA1_HUMAN.

Comparing the score from the subject with the plurality of scores obtained from the reference population can provide a cancer probability. Preferably, when the comparison provides a cancer probability and the probability is 15% or less, the lung condition is classified as not cancer. More preferably, when the comparison provides a cancer probability and the probability is 10% or less, the lung condition is classified as not cancer. Most preferably, when the comparison provides a cancer probability and the probability is 5% or less, the lung condition is classified as not cancer.

The subject can be one that has or is suspected of having a pulmonary nodule. The pulmonary nodule can have a diameter of 30 mm or less. Preferably, the pulmonary nodule has a diameter of about 8 mm to 30 mm.

The subject can be suspected of having a cancerous or non-cancerous lung condition. A cancerous lung condition can include non-small cell lung cancer. A s non-cancerous lung condition can include chronic obstructive pulmonary disease, hamartoma, fibroma, neurofibroma, granuloma, sarcoidosis, bacterial infection or fungal infection.

The subject can be a mammal. Preferably, the subject is a human.

The biological sample can be any sample obtained from the subject, e.g., tissue, cell, fluid. Preferably, the biological sample is tissue, blood, plasma, serum, whole blood, urine, saliva, genital secretions, cerebrospinal fluid, sweat, excreta, or bronchioalveolar lavage.

The methods of the present invention can also include assessing the expression of a plurality of proteins which comprises determining the protein expression level of at least one of PEDF_HUMAN, MASP1_HUMAN, GELS_HUMAN, LUM_HUMAN, C163A_HUMAN and PTPRJ_HUMAN.

Determining the protein level of at least one of, or each of, the proteins of the present invention can include fragmenting the protein to generate at least one peptide per protein. Preferably, the fragmentation of the protein is accomplished by trypsin digestion.

The methods of the present invention can further include normalizing the protein measurements. For example, the protein measurements can normalized by one or more "housekeeping" proteins, e.g., proteins which do not have variable expression across different samples or subjects. Preferable normalizing proteins can include at least one of PEDF_HUMAN, MASP1_HUMAN, GELS_HUMAN, LUM_HUMAN, C163A_HUMAN and PTPRJ_HUMAN.

The invention further provides methods of using synthetic, modified, heavy peptides corresponding to at least one of, or each of, ALDOA_HUMAN, FRIL_HUMAN, LG3BP_HUMAN, TSP1_HUMAN, COIA1_HUMAN, PEDF_HUMAN, MASP1_HUMAN, GELS_HUMAN, LUM_HUMAN, C163A_HUMAN or PTPRJ_HUMAN. At least one of, or each of, the synthetic peptides can an isotopic label attached.

Methods to assess the expression of a plurality of proteins can include mass spectrometry (MS), liquid chromatography-selected reaction monitoring/mass spectrometry (LC-SRM-MS), reverse transcriptase-polymerase chain reaction (RT-PCR), microarray, serial analysis of gene expression (SAGE), gene expression analysis by massively parallel signature sequencing (MPSS), immunoassays, immunohistochemistry (IHC), transcriptomics, or proteomics. Preferably, the expression of a plurality of proteins is assessed LC-SRM-MS. LC-SRM-MS can be used to determine transitions for each peptide analyzed. Preferably, peptide transitions can be determined for at least one of, or each of, ALQASALK (SEQ ID NO: 25) (401.25, 617.4), AVGLAGTFR (SEQ ID NO: 26), GFLLLASLR (SEQ ID NO: 27), LGGPEAGLGEYLFER (SEQ ID NO: 28) or VEIFYR (SEQ ID NO: 29). More preferably the peptide transitions include at least ALQASALK (SEQ ID NO: 25) (401.25, 617.4), AVGLAGTFR (SEQ ID NO: 26) (446.26, 721.4), GFLLLASLR (SEQ ID NO: 27) (495.31, 559.4), LGGPEAGLGEYLFER (SEQ ID NO: 28) (804.4, 1083.6), and VEIFYR (SEQ ID NO: 29) (413.73, 598.3).

The measuring step may also be performed using a compound that specifically binds the protein being detected or a peptide transition. For example, a compound that specifically binds to the protein being measured can be an antibody or an aptamer.

The score can be calculated from a logistic regression model applied to the protein measurements. For example, the score is determined as $P_s=1/[1+\exp(-\alpha-\Sigma_{i=1}^{5}\beta_i*\breve{I}_{i,s}-\gamma*\breve{I}_{COIA1}*\breve{I}_{FRIL})]$, where $\breve{I}_{i,s}$ is Box-Cox transformed and normalized intensity of transition i in said sample (s), $\beta_i$ is the corresponding logistic regression coefficient, $\alpha$ is a panel-specific constant, and $\gamma$ is a coefficient for the interaction term.

The reference population can include at least 100 subjects with a lung condition and wherein each subject in the reference population has been assigned a score based on the protein expression of at least each of ALDOA_HUMAN, FRIL_HUMAN, LG3BP_HUMAN, TSP1_HUMAN and COIA1_HUMAN obtained from a biological sample from the subject. The invention further provides methods for the treatment of a subject, wherein if the lung condition is not cancer the subject is treated based on clinical practice guidelines. Preferably, if a lung condition is not cancer the subject receives image monitoring for at least a 1 year period, for at least a 2 year period or at least a 3 year period. More preferably, if the lung condition is not cancer, the subject receives chest computed tomography scans for at least a 1 year period, for at least a 2 year period or at least a 3 year period.

The present invention also provides that at least one step of any disclosed method can be performed on a computer or computer system.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. GenBank and NCBI submissions indicated by accession number cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims.

DETAILED DESCRIPTION OF THE INVENTION

Figure 1:
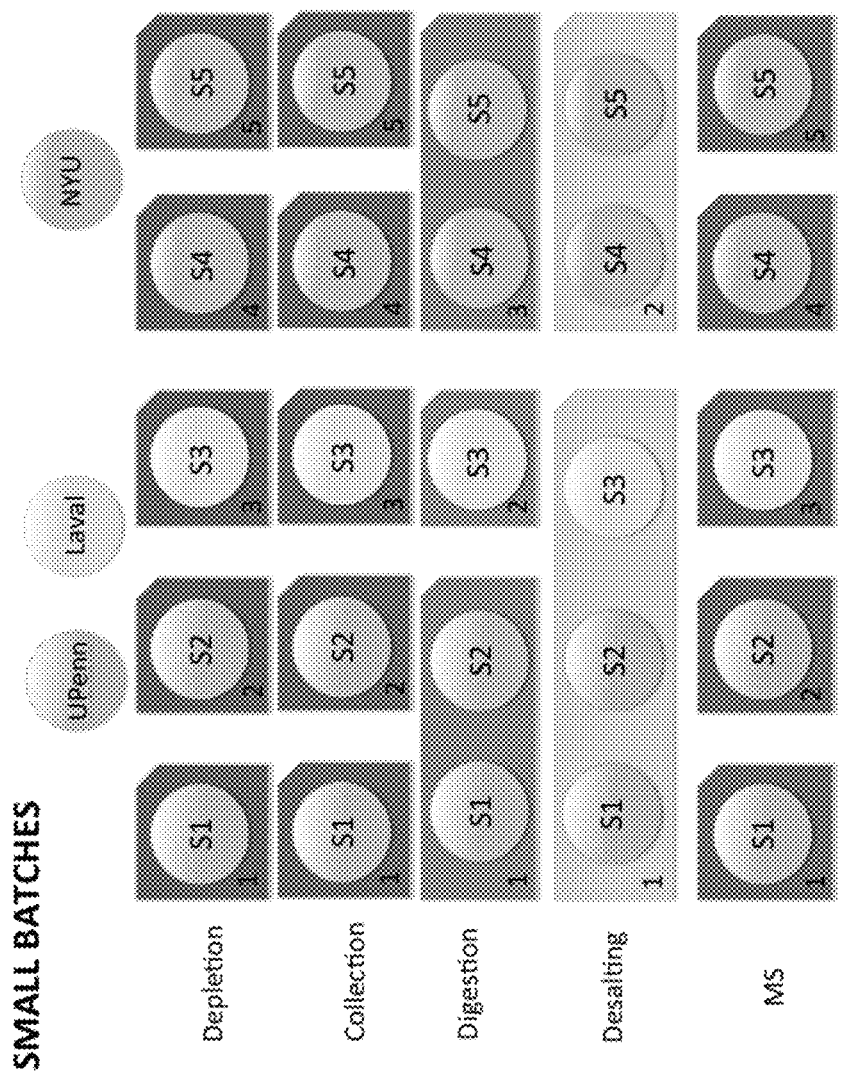
FIG. 1 is a graph showing sample batches used in the experiments from three sites UPenn, Laval and NYU.

The disclosed invention derives from the surprising discovery, that in patients presenting with pulmonary nodule(s), a small panel of protein markers in the blood is able to specifically identify and distinguish malignant and benign lung nodules with high negative predictive value (NPV). More importantly, at least two protein markers among the panel mathematically interact in the model for determining the probability score. Such protein-protein interaction surprisingly increases the specificity of the methods described herein. The classifier (C4 Classifier) described herein also demonstrates remarkable independence and accuracy. None of the clinical factors impact the classifier's score.

Accordingly the invention provides unique advantages to the patient associated with early detection of lung cancer in a patient, including increased life span, decreased morbidity and mortality, decreased exposure to radiation during screening and repeat screenings and a minimally invasive diagnostic model. Importantly, the methods of the invention allow for a patient to avoid invasive procedures.

The routine clinical use of chest computed tomography (CT) scans identifies millions of pulmonary nodules annually, of which only a small minority are malignant but contribute to the dismal 15% five-year survival rate for patients diagnosed with non-small cell lung cancer (NSCLC). The early diagnosis of lung cancer in patients with pulmonary nodules is a top priority, as decision-making based on clinical presentation, in conjunction with current non-invasive diagnostic options such as chest CT and positron emission tomography (PET) scans, and other invasive alternatives, has not altered the clinical outcomes of patients with Stage I NSCLC. The subgroup of pulmonary nodules between 8 mm and 20 mm in size is increasingly recognized as being "intermediate" relative to the lower rate of malignancies below 8 mm and the higher rate of malignancies above 20 mm. Invasive sampling of the lung nodule by biopsy using transthoracic needle aspiration or bronchoscopy may provide a cytopathologic diagnosis of NSCLC, but are also associated with both false-negative and non-diagnostic results. In summary, a key unmet clinical need for the management of pulmonary nodules is a non-invasive diagnostic test that discriminates between malignant and benign processes in patients with indeterminate pulmonary nodules (IPNs), especially between 8 mm and 20 mm in size.

The clinical decision to be more or less aggressive in treatment is based on risk factors, primarily nodule size, smoking history and age in addition to imaging. As these are not conclusive, there is a great need for a molecular-based blood test that would be both non-invasive and provide complementary information to risk factors and imaging.

Accordingly, these and related embodiments will find uses in screening methods for lung conditions, and particularly lung cancer diagnostics. More importantly, the invention finds use in determining the clinical management of a patient. That is, the method of invention is useful in ruling in or ruling out a particular treatment protocol for an individual subject.

Cancer biology requires a molecular strategy to address the unmet medical need for an assessment of lung cancer risk. The field of diagnostic medicine has evolved with technology and assays that provide sensitive mechanisms for detection of changes in proteins. The methods described herein use a LC-SRM-MS technology for measuring the concentration of blood plasma proteins that are collectively changed in patients with a malignant PN. This protein signature is indicative of lung cancer. LC-SRM-MS is one method that provides for both quantification and identification of circulating proteins in plasma. Changes in protein expression levels, such as but not limited to signaling factors, growth factors, cleaved surface proteins and secreted proteins, can be detected using such a sensitive technology to assay cancer. Presented herein is a blood-based classification test to determine the likelihood that a patient presenting with a pulmonary nodule has a nodule that is benign or malignant. The present invention presents a classification algorithm that predicts the relative likelihood of the PN being benign or malignant.

More broadly, it is demonstrated that there are many variations on this invention that are also diagnostic tests for the likelihood that a PN is benign or malignant. These are variations on the panel of proteins, protein standards, measurement methodology and/or classification algorithm.

The present invention also provides methods of determining that a lung condition in a subject is cancer comprising assessing the expression of a plurality of proteins comprising determining the protein expression level of at least each of ALDOA_HUMAN, FRIL_HUMAN, LG3BP_HUMAN, TSP1_HUMAN and COIA1_HUMAN from a biological sample obtained from the subject; calculating a score from the protein expression of at least each of ALDOA_HUMAN, FRIL_HUMAN, LG3BP_HUMAN, TSP1_HUMAN and COIA1_HUMAN from the biological sample determined in the preceding step; and comparing the score from the biological sample to a plurality of scores obtained from a reference population, wherein the comparison provides a determination that the lung condition is not cancer.

The determination that a lung condition is not cancer can include assessing the expression of a plurality of proteins to determine the protein expression level of at least each of ALDOA_HUMAN, FRIL_HUMAN, LG3BP_HUMAN, TSP1_HUMAN, and COIA1_HUMAN obtained from a biological sample from a subject. A score is calculated from these assessments and this score is further compared with a plurality of scores obtained from a reference population, wherein the comparison provides a determination that the lung condition is not cancer. The method can also include determining an interaction between FRIL_HUMAN AND COIA1_HUMAN.

Comparing the score from the subject with the plurality of scores obtained from the reference population can provide a cancer probability. Preferably, when the comparison provides a cancer probability and the probability is 15% or less, the lung condition is classified as not cancer. More preferably, when the comparison provides a cancer probability and the probability is 10% or less, the lung condition is classified as not cancer. Most preferably, when the comparison provides a cancer probability and the probability is 5% or less, the lung condition is classified as not cancer.

The subject can be one that has or is suspected of having a pulmonary nodule. The pulmonary nodule can have a diameter of 30 mm or less. Preferably, the pulmonary nodule has a diameter of about 8 mm to 30 mm.

The subject can be suspected of having a cancerous or non-cancerous lung condition. A cancerous lung condition can include non-small cell lung cancer. A s non-cancerous lung condition can include chronic obstructive pulmonary disease, hamartoma, fibroma, neurofibroma, granuloma, sarcoidosis, bacterial infection or fungal infection.

The subject can be a mammal. Preferably, the subject is a human.

The biological sample can be any sample obtained from the subject, e.g., tissue, cell, fluid. Preferably, the biological sample is tissue, blood, plasma, serum, whole blood, urine, saliva, genital secretions, cerebrospinal fluid, sweat, excreta, or bronchoalveolar lavage.

The methods of the present invention can also include assessing the expression of a plurality of proteins which comprises determining the protein expression level of at least one of PEDF_HUMAN, MASP1_HUMAN, GELS_HUMAN, LUM_HUMAN, C163A_HUMAN and PTPRJ_HUMAN.

Determining the protein level of at least one of, or each of, the proteins of the present invention can include fragmenting the protein to generate at least one peptide per protein. Preferably, the fragmentation of the protein is accomplished by trypsin digestion.

The methods of the present invention can further include normalizing the protein measurements. For example, the protein measurements can normalized by one or more "housekeeping" proteins, e.g., proteins which do not have variable expression across different samples or subjects. Preferable normalizing proteins can include at least one of PEDF_HUMAN, MASP1_HUMAN, GELS_HUMAN, LUM_HUMAN, C163A_HUMAN and PTPRJ_HUMAN.

The invention further provides methods of using synthetic, modified, heavy peptides corresponding to at least one of, or each of, ALDOA_HUMAN, FRIL_HUMAN, LG3BP_HUMAN, TSP1_HUMAN, COIA1_HUMAN, PEDF_HUMAN, MASP1_HUMAN, GELS_HUMAN, LUM_HUMAN, C163A_HUMAN or PTPRJ_HUMAN. At least one of, or each of, the synthetic peptides can an isotopic label attached.

Methods to assess the expression of a plurality of proteins can include mass spectrometry (MS), liquid chromatography-selected reaction monitoring/mass spectrometry (LC-SRM-MS), reverse transcriptase-polymerase chain reaction (RT-PCR), microarray, serial analysis of gene expression (SAGE), gene expression analysis by massively parallel signature sequencing (MPSS), immunoassays, immunohistochemistry (IHC), transcriptomics, or proteomics. Preferably, the expression of a plurality of proteins is assessed LC-SRM-MS. LC-SRM-MS can be used to determine transitions for each peptide analyzed. Preferably, peptide transitions can be determined for at least one of, or each of, ALQASALK (SEQ ID NO: 25), AVGLAGTFR (SEQ ID NO: 26), GFLLLASLR (SEQ ID NO: 27), LGGPEAGLGEYLFER (SEQ ID NO: 28) or VEIFYR (SEQ ID NO: 29). More preferably the peptide transitions include at least ALQASALK (SEQ ID NO: 25) (401.25, 617.4), AVGLAGTFR (SEQ ID NO: 26) (446.26, 721.4), GFLLLASLR (SEQ ID NO: 27) (495.31, 559.4), LGGPEAGLGEYLFER (SEQ ID NO: 28) (804.4, 1083.6), and VEIFYR (SEQ ID NO: 29) (413.73, 598.3).

The measuring step may also be performed using a compound that specifically binds the protein being detected or a peptide transition. For example, a compound that specifically binds to the protein being measured can be an antibody or an aptamer.

The score can be calculated from a logistic regression model applied to the protein measurements. For example, the score is determined as $P_s = 1/[1+\exp(-\alpha - \Sigma_{i=1}^{5} \beta_i * \breve{I}_{i,s} - \gamma * \breve{I}_{COIA1} * \breve{I}_{FRIL})]$, where $\breve{I}_{i,s}$ is Box-Cox transformed and normalized intensity of transition i in said sample (s), $\beta_i$ is the corresponding logistic regression coefficient, $\alpha$ is a panel-specific constant, and $\gamma$ is a coefficient for the interaction term.

The reference population can include at least 100 subjects with a lung condition and wherein each subject in the reference population has been assigned a score based on the protein expression of at least each of ALDOA_HUMAN, FRIL_HUMAN, LG3BP_HUMAN, TSP1_HUMAN and COIA1_HUMAN obtained from a biological sample from the subject. The invention further provides methods for the treatment of a subject, wherein if the lung condition is not cancer the subject is treated based on clinical practice guidelines. Preferably, if a lung condition is not cancer the subject receives image monitoring for at least a 1 year period, for at least a 2 year period or at least a 3 year period. More preferably, if the lung condition is not cancer, the subject receives chest computed tomography scans for at least a 1 year period, for at least a 2 year period or at least a 3 year period.

The present invention also provides that at least one step of any disclosed method can be performed on a computer or computer system.

As disclosed herein, archival plasma samples from subjects presenting with PNs were analyzed for differential protein expression by mass spectrometry and the results were used to identify biomarker proteins and panels of biomarker proteins that are differentially expressed in conjunction with various lung conditions (cancer vs. non-cancer).

In one aspect of the invention, the panel comprises at least 2, 3, 4, 5, or more protein markers with at least one protein-protein interaction. In some embodiments, the panel comprises 5 protein markers with at least one protein-protein interaction. In some embodiments, the panel comprises ALDOA_HUMAN, FRIL_HUMAN, LG3BP_HUMAN, TSP1_HUMAN, and COIA1_HUMAN; and FRIL_HUMAN and COIA1_HUMAN interact in the model for determining the probability score of cancer. In some embodiments, the panel comprises 2, 3, or 4 biomarkers selected from the group consisting of ALDOA_HUMAN, FRIL_HUMAN, LG3BP_HUMAN, TSP1_HUMAN, and COIA1_HUMAN; and at least one protein-protein mathematical interaction exits among the biomarkers.

Additional biomarkers that can be used herein are described in WO 13/096845, the contents of which are incorporated herein by reference in its entireties.

The term "interact", "interacted", "interaction" or "protein-protein interaction" used herein refers to mathematical interaction between peptides (or peptide transitions) derived from two or more protein markers when calculating the probability score of cancer.

The term "pulmonary nodules" (PNs) refers to lung lesions that can be visualized by radiographic techniques. A pulmonary nodule is any nodules less than or equal to three centimeters in diameter. In one example a pulmonary nodule has a diameter of about 0.8 cm to 2 cm.

The term "masses" or "pulmonary masses" refers to lung nodules that are greater than three centimeters maximal diameter.

The term "blood biopsy" refers to a diagnostic study of the blood to determine whether a patient presenting with a nodule has a condition that may be classified as either benign or malignant.

The term "acceptance criteria" refers to the set of criteria to which an assay, test, diagnostic or product should conform to be considered acceptable for its intended use. As used herein, acceptance criteria are a list of tests, references to analytical procedures, and appropriate measures, which are defined for an assay or product that will be used in a diagnostic. For example, the acceptance criteria for the classifier refer to a set of predetermined ranges of coefficients.

The term "average maximal AUC" refers to the methodology of calculating performance. For the present invention, in the process of defining the set of proteins that should be in a panel by forward or backwards selection proteins are removed or added one at a time. A plot can be generated with performance (AUC or partial AUC score on the Y axis and proteins on the X axis) the point which maximizes performance indicates the number and set of proteins the gives the best result.

The term "partial AUC factor or pAUC factor" is greater than expected by random prediction. At sensitivity=0.90 the pAUC factor is the trapezoidal area under the ROC curve from 0.9 to 1.0 Specificity/(0.1*0.1/2).

The term "incremental information" refers to information that may be used with other diagnostic information to enhance diagnostic accuracy. Incremental information is independent of clinical factors such as including nodule size, age, or gender.

The term "score" or "scoring" refers to calculating a probability likelihood for a sample. For the present invention, values closer to 1.0 are used to represent the likelihood that a sample is cancer, values closer to 0.0 represent the likelihood that a sample is benign.

The term "robust" refers to a test or procedure that is not seriously disturbed by violations of the assumptions on which it is based. For the present invention, a robust test is a test wherein the proteins or transitions of the mass spectrometry chromatograms have been manually reviewed and are "generally" free of interfering signals.

The term "coefficients" refers to the weight assigned to each protein used to in the logistic regression model to score a sample.

In certain embodiments of the invention, it is contemplated that in terms of the logistic regression model of MC CV, the model coefficient and the coefficient of variation (CV) of each protein's model coefficient may increase or decrease, dependent upon the method (or model) of measurement of the protein classifier. For each of the listed proteins in the panels, there is about, at least, at least about, or at most about a 2-, 3-, 4-, 5-, 6-, 7-, 8-, 9-, or 10-, -fold or any range derivable therein for each of the coefficient and CV. Alternatively, it is contemplated that quantitative embodiments of the invention may be discussed in terms of as about, at least, at least about, or at most about 10, 20, 30, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

The term "best team players" refers to the proteins that rank the best in the random panel selection algorithm, i.e., perform well on panels. When combined into a classifier these proteins can segregate cancer from benign samples. "Best team player proteins" are synonymous with "cooperative proteins". The term "cooperative proteins" refers to proteins that appear more frequently on high performing panels of proteins than expected by chance. This gives rise to a protein's cooperative score which measures how (in)frequently it appears on high performing panels. For example, a protein with a cooperative score of 1.5 appears on high performing panels 1.5× more than would be expected by chance alone.

The term "classifying" as used herein with regard to a lung condition refers to the act of compiling and analyzing expression data for using statistical techniques to provide a classification to aid in diagnosis of a lung condition, particularly lung cancer.

The term "classifier" as used herein refers to an algorithm that discriminates between disease states with a predetermined level of statistical significance. A two-class classifier is an algorithm that uses data points from measurements from a sample and classifies the data into one of two groups. In certain embodiments, the data used in the classifier is the relative expression of proteins in a biological sample. Protein expression levels in a subject can be compared to levels in patients previously diagnosed as disease free or with a specified condition. Table 4 lists a representative classifier (C4 Classifier).

The "classifier" maximizes the probability of distinguishing a randomly selected cancer sample from a randomly selected benign sample, i.e., the AUC of ROC curve.

In addition to the classifier's constituent proteins with differential expression, it may also include proteins with minimal or no biologic variation to enable assessment of variability, or the lack thereof, within or between clinical specimens; these proteins may be termed endogenous proteins and serve as internal controls for the other classifier proteins.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression. This prevents the technical variation of sample preparation and mass spectrometry measurement from impeding the measurement of protein concentration levels in the sample.

The term "condition" as used herein refers generally to a disease, event, or change in health status.

The term "treatment protocol" as used herein including further diagnostic testing typically performed to determine whether a pulmonary nodule is benign or malignant. Treatment protocols include diagnostic tests typically used to diagnose pulmonary nodules or masses such as for example, CT scan, positron emission tomography (PET) scan, bronchoscopy or tissue biopsy. Treatment protocol as used herein is also meant to include therapeutic treatments typically used to treat malignant pulmonary nodules and/or lung cancer such as for example, chemotherapy, radiation or surgery.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop a hyperproliferative disease) b. prognosis (predicting whether a patient will likely have a better or worse outcome at a pre-selected time in the future) c. therapy selection d. therapeutic drug monitoring e. relapse monitoring.

In some embodiments, for example, classification of a biological sample as being derived from a subject with a lung condition may refer to the results and related reports generated by a laboratory, while diagnosis may refer to the act of a medical professional in using the classification to identify or verify the lung condition.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

As used herein, "lung cancer" preferably refers to cancers of the lung, but may include any disease or other disorder of the respiratory system of a human or other mammal. Respiratory neoplastic disorders include, for example small cell carcinoma or small cell lung cancer (SCLC), non-small cell carcinoma or non-small cell lung cancer (NSCLC), squamous cell carcinoma, adenocarcinoma, broncho-alveolar carcinoma, mixed pulmonary carcinoma, malignant pleural mesothelioma, undifferentiated large cell carcinoma, giant cell carcinoma, synchronous tumors, large cell neuroendocrine carcinoma, adenosquamous carcinoma, undifferentiated carcinoma; and small cell carcinoma, including oat cell cancer, mixed small cell/large cell carcinoma, and combined small cell carcinoma; as well as adenoid cystic carcinoma, hamartomas, mucoepidermoid tumors, typical carcinoid lung tumors, atypical carcinoid lung tumors, peripheral carcinoid lung tumors, central carcinoid lung tumors, pleural mesotheliomas, and undifferentiated pulmonary carcinoma and cancers that originate outside the lungs such as secondary cancers that have metastasized to the lungs from other parts of the body. Lung cancers may be of any stage or grade. Preferably the term may be used to refer collectively to any dysplasia, hyperplasia, neoplasia, or metastasis in which the protein biomarkers expressed above normal levels as may be determined, for example, by comparison to adjacent healthy tissue.

Examples of non-cancerous lung condition include chronic obstructive pulmonary disease (COPD), benign tumors or masses of cells (e.g., hamartoma, fibroma, neurofibroma), granuloma, sarcoidosis, and infections caused by bacterial (e.g., tuberculosis) or fungal (e.g. histoplasmosis) pathogens. In certain embodiments, a lung condition may be associated with the appearance of radiographic PNs.

As used herein, "lung tissue", and "lung cancer" refer to tissue or cancer, respectively, of the lungs themselves, as well as the tissue adjacent to and/or within the strata underlying the lungs and supporting structures such as the pleura, intercostal muscles, ribs, and other elements of the respiratory system. The respiratory system itself is taken in this context as representing nasal cavity, sinuses, pharynx, larynx, trachea, bronchi, lungs, lung lobes, aveoli, aveolar ducts, aveolar sacs, aveolar capillaries, bronchioles, respiratory bronchioles, visceral pleura, parietal pleura, pleural cavity, diaphragm, epiglottis, adenoids, tonsils, mouth and tongue, and the like. The tissue or cancer may be from a mammal and is preferably from a human, although monkeys, apes, cats, dogs, cows, horses and rabbits are within the scope of the present invention. The term "lung condition" as used herein refers to a disease, event, or change in health status relating to the lung, including for example lung cancer and various non-cancerous conditions.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

The term "biomarker protein" as used herein refers to a polypeptide in a biological sample from a subject with a lung condition versus a biological sample from a control subject. A biomarker protein includes not only the polypeptide itself, but also minor variations thereof, including for example one or more amino acid substitutions or modifications such as glycosylation or phosphorylation.

The term "biomarker protein panel" as used herein refers to a plurality of biomarker proteins. In certain embodiments, the expression levels of the proteins in the panels can be correlated with the existence of a lung condition in a subject. In certain embodiments, biomarker protein panels comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 proteins. In certain embodiments, the biomarker proteins panels comprise 2-5 proteins, 5-10 proteins, 10-20 proteins or more.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. One skilled in the art should be able to determine a reasonable measurable change. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

Using the methods of the current invention, a clinical assessment of a patient is first performed. If there exists is a higher likelihood for cancer, the clinician may rule in the disease which will require the pursuit of diagnostic testing options yielding data which increase and/or substantiate the likelihood of the diagnosis. "Rule in" of a disease requires a test with a high specificity.

"FN" is false negative, which for a disease state test means classifying a disease subject incorrectly as non-disease or normal.

"FP" is false positive, which for a disease state test means classifying a normal subject incorrectly as having disease.

The term "rule in" refers to a diagnostic test with high specificity that optionally coupled with a clinical assessment indicates a higher likelihood for cancer. If the clinical assessment is a lower likelihood for cancer, the clinician may adopt a stance to rule out the disease, which will require diagnostic tests which yield data that decrease the likelihood of the diagnosis. "Rule out" requires a test with a high sensitivity. Accordingly, the term "ruling in" as used herein is meant that the subject is selected to receive a treatment protocol.

The term "rule out" refers to a diagnostic test with high sensitivity that optionally coupled with a clinical assessment indicates a lower likelihood for cancer. Accordingly, the term "ruling out" as used herein is meant that the subject is selected not to receive a treatment protocol.

The term "sensitivity of a test" refers to the probability that a patient with the disease will have a positive test result. This is derived from the number of patients with the disease who have a positive test result (true positive) divided by the total number of patients with the disease, including those with true positive results and those patients with the disease who have a negative result, i.e. false negative.

The term "specificity of a test" refers to the probability that a patient without the disease will have a negative test result. This is derived from the number of patients without the disease who have a negative test result (true negative) divided by all patients without the disease, including those with a true negative result and those patients without the disease who have a positive test result, e.g. false positive. While the sensitivity, specificity, true or false positive rate, and true or false negative rate of a test provide an indication of a test's performance, e.g. relative to other tests, to make a clinical decision for an individual patient based on the test's result, the clinician requires performance parameters of the test with respect to a given population.

The term "positive predictive value" (PPV) refers to the probability that a positive result correctly identifies a patient who has the disease, which is the number of true positives divided by the sum of true positives and false positives.

The term "negative predictive value" or "NPV" is calculated by TN/(TN+FN) or the true negative fraction of all negative test results. It also is inherently impacted by the prevalence of the disease and pre-test probability of the population intended to be tested. The term NPV refers to the probability that a negative test correctly identifies a patient without the disease, which is the number of true negatives divided by the sum of true negatives and false negatives. A positive result from a test with a sufficient PPV can be used to rule in the disease for a patient, while a negative result from a test with a sufficient NPV can be used to rule out the disease, if the disease prevalence for the given population, of which the patient can be considered a part, is known.

The term "disease prevalence" refers to the number of all new and old cases of a disease or occurrences of an event during a particular period. Prevalence is expressed as a ratio in which the number of events is the numerator and the population at risk is the denominator.

The term disease incidence refers to a measure of the risk of developing some new condition within a specified period of time; the number of new cases during some time period, it is better expressed as a proportion or a rate with a denominator.

Lung cancer risk according to the "National Lung Screening Trial" is classified by age and smoking history. High risk—age ≥55 and ≥30 pack-years smoking history; Moderate risk—age ≥50 and ≥20 pack-years smoking history; Low risk—<age 50 or <20 pack-years smoking history.

The clinician must decide on using a diagnostic test based on its intrinsic performance parameters, including sensitivity and specificity, and on its extrinsic performance parameters, such as positive predictive value and negative predictive value, which depend upon the disease's prevalence in a given population.

Additional parameters which may influence clinical assessment of disease likelihood include the prior frequency and closeness of a patient to a known agent, e.g. exposure risk, that directly or indirectly is associated with disease causation, e.g. second hand smoke, radiation, etc., and also the radiographic appearance or characterization of the pulmonary nodule exclusive of size. A nodule's description may include solid, semi-solid or ground glass which characterizes it based on the spectrum of relative gray scale density employed by the CT scan technology.

"Mass spectrometry" refers to a method comprising employing an ionization source to generate gas phase ions from an analyte presented on a sample presenting surface of a probe and detecting the gas phase ions with a mass spectrometer.

In an embodiment of the invention, a panel of 5 proteins (ALDOA, FRIL, LG3BP, TSP1, and COIA1) and one protein-protein interaction term (FRIL and COIA1) effectively distinguish between samples derived from patients with benign and malignant nodules less than 2 cm diameter.

Bioinformatic and biostatistical analyses were used first to identify individual proteins with statistically significant differential expression, and then using these proteins to derive one or more combinations of proteins or panels of proteins, which collectively demonstrated superior discriminatory performance compared to any individual protein. Bioinformatic and biostatistical methods are used to derive coefficients (C) for each individual protein in the panel that reflects its relative expression level, i.e. increased or decreased, and its weight or importance with respect to the panel's net discriminatory ability, relative to the other proteins. The quantitative discriminatory ability of the panel can be expressed as a mathematical algorithm with a term for each of its constituent proteins being the product of its coefficient and the protein's plasma expression level (P) (as measured by LC-SRM-MS), e.g. C×P, with an algorithm consisting of n proteins described as: $C1 \times P1 + C2 \times P2 + C3 \times P3 + + Cn \times Pn$. An algorithm that discriminates between disease states with a predetermined level of statistical significance may be refers to a "disease classifier". In addition to the classifier's constituent proteins with differential expression, it may also include proteins with minimal or no biologic variation to enable assessment of variability, or the lack thereof, within or between clinical specimens; these proteins may be termed typical native proteins and serve as internal controls for the other classifier proteins.

In certain embodiments, expression levels are measured by MS. MS analyzes the mass spectrum produced by an ion after its production by the vaporization of its parent protein and its separation from other ions based on its mass-to-charge ratio. The most common modes of acquiring MS data are 1) full scan acquisition resulting in the typical total ion current plot (TIC), 2) selected ion monitoring (SIM), and 3) selected reaction monitoring (SRM).

In certain embodiments of the methods provided herein, biomarker protein expression levels are measured by LC-SRM-MS. LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio is superior to conventional tandem mass spectrometry (MS/MS) experiments, which select one mass window in the first quadrupole and then measure all generated transitions in the ion detector. LC-SRM-MS.

In certain embodiments, an SRM-MS assay for use in diagnosing or monitoring lung cancer as disclosed herein may utilize one or more peptides and/or peptide transitions derived from the proteins ALDOA_HUMAN, FRIL_HUMAN, LG3BP_HUMAN, TSP1_HUMAN, and COIA1_HUMAN. In certain embodiments, the peptides and/or peptide transitions derived from 2 or more proteins "interact" mathematically. In certain embodiments, the peptides and/or peptide transitions derived from FRIL and COIA1 mathematically interact in the model for determining the probability score of lung cancer.

The expression level of a biomarker protein can be measured using any suitable method known in the art, including but not limited to mass spectrometry (MS), reverse transcriptase-polymerase chain reaction (RT-PCR), microarray, serial analysis of gene expression (SAGE), gene expression analysis by massively parallel signature sequencing (MPSS), immunoassays (e.g., ELISA), immunohistochemistry (IHC), transcriptomics, and proteomics.

To evaluate the diagnostic performance of a particular set of peptide transitions, a ROC curve is generated for each significant transition.

An "ROC curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a biomarker or a panel of biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a biomarker protein has an AUC in the range of about 0.75 to 1.0. In certain of these embodiments, the AUC is in the range of about 0.8 to 0.8, 0.9 to 0.95, or 0.95 to 1.0.

The methods provided herein are minimally invasive and pose little or no risk of adverse effects. As such, they may be used to diagnose, monitor and provide clinical management of subjects who do not exhibit any symptoms of a lung condition and subjects classified as low risk for developing a lung condition. For example, the methods disclosed herein may be used to diagnose lung cancer in a subject who does not present with a PN and/or has not presented with a PN in the past, but who nonetheless deemed at risk of developing a PN and/or a lung condition. Similarly, the methods disclosed herein may be used as a strictly precautionary measure to diagnose healthy subjects who are classified as low risk for developing a lung condition.

The present invention provides a method of determining the likelihood that a lung condition in a subject is cancer by measuring an abundance of a panel of proteins in a sample obtained from the subject; calculating a probability of cancer score based on the protein measurements and ruling out cancer for the subject if the score is lower than a predetermined score, when cancer is ruled out the subject does not receive a treatment protocol. Treatment protocols include for example pulmonary function test (PFT), pulmonary imaging, a biopsy, a surgery, a chemotherapy, a radiotherapy, or any combination thereof. In some embodiments, the imaging is an x-ray, a chest computed tomography (CT) scan, or a positron emission tomography (PET) scan.

The present invention further provides a method of ruling in the likelihood of cancer for a subject by measuring an abundance of panel of proteins in a sample obtained from the subject, calculating a probability of cancer score based on the protein measurements and ruling in the likelihood of cancer for the subject if the score is higher than a predetermined score In another aspect the invention further provides a method of determining the likelihood of the presence of a lung condition in a subject by measuring an abundance of panel of proteins in a sample obtained from the subject, calculating a probability of cancer score based on the protein measurements and concluding the presence of this lung condition if the score is equal or greater than a pre-determined score. The lung condition is lung cancer such as for example, non-small cell lung cancer (NSCLC). The subject is at risk of developing lung cancer.

The panel includes 5 proteins ALDOA_HUMAN, FRIL_HUMAN, LG3BP_HUMAN, TSP1_HUMAN, and COIA1_HUMAN. Nucleic acid and amino acid sequences for these can be found in Table 6 and Table 7, respectively. Preferably, FRIL_HUMAN and COIA1_HUMAN mathematically interact in the model for determining the probability score.

In merely illustrative embodiments, the methods described herein include steps of (a) measuring the abundance (intensity) of one representative peptide transition derived from each of the proteins comprising ALDOA_HUMAN, FRIL_HUMAN, LG3BP_HUMAN, TSP1_HUMAN, and COIA1_HUMAN in a sample obtained from a subject; (b) determining the coefficient for each representative peptide transition; (c) calculating a sum of the products of each logarithmically transformed (and optionally normalized) intensity of each transition and its corresponding coefficient; (d) calculating a mathematical interaction between FRIL and COIA1 by multiplying their logarithmically transformed (and optionally normalized) intensity of their representative peptide transitions; and (e)

calculating a probability of cancer score based on the sum calculated in step (c) and the mathematical interaction calculated in step (d).

In some embodiments, the representative peptide transitions for proteins ALDOA_HUMAN, COIA1_HUMAN, TSP1_HUMAN, FRIL_HUMAN, and LG3BP_HUMAN are ALQASALK (SEQ ID NO: 25) (401.25, 617.4), AVGLAGTFR (SEQ ID NO: 26) (446.26, 721.4), GFLL-LASLR (SEQ ID NO: 27) (495.31, 559.4), LGG-PEAGLGEYLFER (SEQ ID NO: 28) (804.4, 1083.6), and VEIFYR (SEQ ID NO: 29) (413.73, 598.3), respectively.

In some embodiments, the measuring step of any method described herein is performed by detecting transitions comprising ALQASALK (SEQ ID NO: 25) (401.25, 617.4), AVGLAGTFR (SEQ ID NO: 26) (446.26, 721.4), GFLL-LASLR (SEQ ID NO: 27) (495.31, 559.4), LGG-PEAGLGEYLFER (SEQ ID NO: 28) (804.4, 1083.6), and VEIFYR (SEQ ID NO: 29) (413.73, 598.3).

The subject has or is suspected of having a pulmonary nodule. The pulmonary nodule has a diameter of less than or equal to 3.0 cm. In one embodiment, the pulmonary nodule has a diameter of about 0.8 cm to 2.0 cm. The subject may have stage IA lung cancer (i.e., the tumor is smaller than 3 cm).

The probability score is calculated from a logistic regression model applied to the protein measurements. For example, the score is determined as $P_s=1/[1+\exp(-\alpha-\Sigma_{i=1}^{5}\beta_i*\check{I}_{i,s}-\gamma*\check{I}_{COIA1}*\check{I}_{FRIL})]$, where $\check{I}_{i,s}$ is Box-Cox transformed and normalized intensity of transition i in said sample (s), $\beta_i$ is the corresponding logistic regression coefficient, $\alpha$ is a panel-specific constant, and $\gamma$ is a coefficient for the interaction term. The score determined has a negative predictive value (NPV) of at least about 85%, at least 90% or higher (91%, 92%, 93%, 94%, 95%, 96%, 97%, 98%, 99% or higher).

In various embodiments, the method of the present invention further comprises normalizing the protein measurements. For example, the protein measurements are normalized by one or more proteins selected from PEDF_HUMAN, MASP1_HUMAN, GELS_HUMAN, LUM_HUMAN, C163A_HUMAN and PTPRJ_HUMAN. Nucleic acid and amino acid sequences for these can be found in Table 8 and Table 9, respectively.

The biological sample includes such as for example tissue, blood, plasma, serum, whole blood, urine, saliva, genital secretion, cerebrospinal fluid, sweat and excreta.

In some embodiments, the determining the likelihood of cancer is determined by the sensitivity, specificity, negative predictive value or positive predictive value associated with the score.

The measuring step is performed by selected reaction monitoring mass spectrometry, using a compound that specifically binds the protein being detected or a peptide transition. In one embodiment, the compound that specifically binds to the protein being measured is an antibody or an aptamer.

In specific embodiments, the diagnostic methods disclosed herein are used to rule out a treatment protocol for a subject, measuring the abundance of a panel of proteins in a sample obtained from the subject, calculating a probability of cancer score based on the protein measurements and protein-protein interaction and ruling out the treatment protocol for the subject if the score determined in the sample is lower than a pre-determined score. In some embodiments the panel contains ALDOA_HUMAN, FRIL_HUMAN, LG3BP_HUMAN, TSP1_HUMAN, and COIA1_HUMAN; and FRIL_HUMAN and COIA1_HUMAN interact in the model for determining the score.

In specific embodiments, the diagnostic methods disclosed herein are used to rule in a treatment protocol for a subject by measuring the abundance of a panel of proteins in a sample obtained from the subject, calculating a probability of cancer score based on the protein measurements and protein-protein interaction and ruling in the treatment protocol for the subject if the score determined in the sample is greater than a pre-determined score. In some embodiments the panel contains ALDOA_HUMAN, FRIL_HUMAN, LG3BP_HUMAN, TSP1_HUMAN, and COIA1_HUMAN; and FRIL_HUMAN and COIA1_HUMAN interact in the model for determining the score.

In certain embodiments, the diagnostic methods disclosed herein can be used in combination with other clinical assessment methods, including for example various radiographic and/or invasive methods. Similarly, in certain embodiments, the diagnostic methods disclosed herein can be used to identify candidates for other clinical assessment methods, or to assess the likelihood that a subject will benefit from other clinical assessment methods.

The high abundance of certain proteins in a biological sample such as plasma or serum can hinder the ability to assay a protein of interest, particularly where the protein of interest is expressed at relatively low concentrations. Several methods are available to circumvent this issue, including enrichment, separation, and depletion. Enrichment uses an affinity agent to extract proteins from the sample by class, e.g., removal of glycosylated proteins by glycocapture. Separation uses methods such as gel electrophoresis or isoelectric focusing to divide the sample into multiple fractions that largely do not overlap in protein content. Depletion typically uses affinity columns to remove the most abundant proteins in blood, such as albumin, by utilizing advanced technologies such as IgY14/Supermix (SigmaSt. Louis, Mo.) that enable the removal of the majority of the most abundant proteins.

In certain embodiments of the methods provided herein, a biological sample may be subjected to enrichment, separation, and/or depletion prior to assaying biomarker or putative biomarker protein expression levels. In certain of these embodiments, blood proteins may be initially processed by a glycocapture method, which enriches for glycosylated proteins, allowing quantification assays to detect proteins in the high pg/ml to low ng/ml concentration range. Exemplary methods of glycocapture are well known in the art (see, e.g., U.S. Pat. No. 7,183,188; U.S. Patent Appl. Publ. No. 2007/0099251; U.S. Patent Appl. Publ. No. 2007/0202539; U.S. Patent Appl. Publ. No. 2007/0269895; and U.S. Patent Appl. Publ. No. 2010/0279382). In other embodiments, blood proteins may be initially processed by a protein depletion method, which allows for detection of commonly obscured biomarkers in samples by removing abundant proteins. In one such embodiment, the protein depletion method is a Supermix (Sigma) depletion method.

In certain embodiments, a biomarker protein panel comprises two to 100 biomarker proteins. In certain of these embodiments, the panel comprises 2 to 5, 6 to 10, 11 to 15, 16 to 20, 21-25, 5 to 25, 26 to 30, 31 to 40, 41 to 50, 25 to 50, 51 to 75, 76 to 100, biomarker proteins. In certain embodiments, a biomarker protein panel comprises one or more subpanels of biomarker proteins that each comprises at least two biomarker proteins. For example, biomarker protein panel may comprise a first subpanel made up of biomarker proteins that are overexpressed in a particular lung condition and a second subpanel made up of biomarker proteins that are under-expressed in a particular lung condition.

In certain embodiments of the methods, compositions, and kits provided herein, a biomarker protein may be a protein that exhibits differential expression in conjunction with lung cancer.

In other embodiments, the diagnosis methods disclosed herein may be used to distinguish between two different lung conditions. For example, the methods may be used to classify a lung condition as malignant lung cancer versus benign lung cancer, NSCLC versus SCLC, or lung cancer versus non-cancer condition (e.g., inflammatory condition).

In certain embodiments, kits are provided for diagnosing a lung condition in a subject. These kits are used to detect expression levels of one or more biomarker proteins. Optionally, a kit may comprise instructions for use in the form of a label or a separate insert. The kits can contain reagents that specifically bind to proteins in the panels described, herein. These reagents can include antibodies. The kits can also contain reagents that specifically bind to mRNA expressing proteins in the panels described, herein. These reagents can include nucleotide probes. The kits can also include reagents for the detection of reagents that specifically bind to the proteins in the panels described herein. These reagents can include fluorophores.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention

EXAMPLES

Example 1: Identification of a Robust Classifier that Distinguishes Malignant and Benign Lung Nodule Plasma samples of patients originated from three sites (UPenn, Laval and NYU) were divided into five experimental batches. Within each batch, four aliquots of a pooled human plasma standard (HPS) sample were processed. Plasma samples were immuno-depleted, denatured, reduced, trypsin-digested, and analyzed by LC-MRM-MS at Integrated Diagnostics using protocols developed in previous studies.

The 100 clinical samples were all from patients with lung nodules of 8-20 mm in size and age >40 years. Cancer and benign samples were matched on gender, age (+/−10 years) and nodule size (+/−8 mm). There were some bias between cancer and benign samples on smoking history and on smoking pack-years.

TABLE 1

Sources of samples and their assignment to five batches.

| Batch | Center | Benign | Cancer | Total |
|---|---|---|---|---|
| S1 | UPenn | 10 | 10 | 20 |
| S2 | UPenn | 10 | 10 | 20 |
| S3 | Laval | 10 | 10 | 20 |
| S4 | NYU | 10 | 10 | 20 |
| S5 | NYU | 10 | 10 | 20 |
| Total | 3 Sites | 50 | 50 | 100 |

Detailed procedures for sample preparation and data processing, including normalization of the raw data can be found in PCT/US2012/071387 (WO13/096845), the contents of which are incorporated herein by their entireties.

Among all the possible panels formed by the 13 proteins identified in WO13/096845, there were 28 panels with a cross-validated performance with partial AUC at specificity=0.9 greater than two-fold the number expected by random chance (0.1^2/2). These models were retained and using 100,000 cross-validation models to get a more accurate measure of their logistic regression coefficients and to determine the coefficient of variability for the model coefficients. Measure the CVs of each protein coefficient and report the NPV, SPC performance, on median panel was performed at a prevalence of 20%.

TABLE 2

| Robust 28 panels | | | | | | | |
|---|---|---|---|---|---|---|---|
| Proteins | max_cv | max_cv_protein | ALPHA_CV | NPV | specificity | threshold | xv_pAUC_factor |
| ALDOA, TSP1, PRDX1, LG3BP | 0.54 | ALDOA | 0.73 | 0.90 | 0.68 | 0.50 | 3.33 |
| ALDOA, TSP1, LG3BP | 0.58 | TSP1 | 0.73 | 0.90 | 0.55 | 0.49 | 4.47 |
| ALDOA, COIA1, TSP1, LG3BP | 0.73 | COIA1 | 0.62 | 0.90 | 0.55 | 0.49 | 4.17 |
| ALDOA, COIA1, FRIL, LG3BP | 0.62 | COIA1 | 0.38 | 0.90 | 0.51 | 0.48 | 3.89 |
| COIA1, LG3BP | 0.78 | COIA1 | 0.57 | 0.90 | 0.51 | 0.49 | 3.75 |
| LG3BP | 0.23 | LG3BP | 0.32 | 0.90 | 0.49 | 0.48 | 4.05 |
| ALDOA, LG3BP | 0.44 | ALDOA | 0.38 | 0.91 | 0.47 | 0.47 | 5.45 |
| ALDOA, LRP1, LG3BP | 0.54 | LRP1 | 0.66 | 0.91 | 0.47 | 0.46 | 4.26 |
| ALDOA, COIA1, PRDX1, LG3BP | 0.73 | ALDOA | 0.75 | 0.90 | 0.45 | 0.45 | 3.82 |
| COIA1, PRDX1, LG3BP | 0.70 | COIA1 | 0.89 | 0.90 | 0.43 | 0.45 | 3.35 |
| ALDOA, COIA1, LG3BP | 0.65 | COIA1 | 0.52 | 0.90 | 0.38 | 0.45 | 5.26 |
| ISLR, ALDOA, COIA1, TSP1, FRIL, PRDX1, LRP1, LG3BP | 6.85 | COIA1 | 0.96 | 0.90 | 0.72 | 0.49 | 2.10 |
| PRDX1, LG3BP | 0.37 | PRDX1 | 1.50 | 0.90 | 0.55 | 0.49 | 3.34 |
| ALDOA, PRDX1, LG3BP | 0.82 | ALDOA | 2.61 | 0.90 | 0.53 | 0.47 | 3.74 |
| ISLR, ALDOA, TSP1, PRDX1, LG3BP | 1.50 | ISLR | 2.00 | 0.90 | 0.53 | 0.48 | 3.31 |
| ISLR, ALDOA, COIA1, TSP1, PRDX1, LG3BP | 42.98 | ISLR | 4.48 | 0.90 | 0.53 | 0.48 | 2.90 |
| ISLR, ALDOA, TSP1, LG3BP | 1.13 | ISLR | 1.04 | 0.90 | 0.51 | 0.48 | 4.08 |

TABLE 2-continued

Robust 28 panels

| Proteins | max_cv | max_cv_protein | ALPHA_CV | NPV | specificity | threshold | xv_pAUC_factor |
|---|---|---|---|---|---|---|---|
| ISLR, ALDOA, COIA1, TSP1, LG3BP | 4.33 | ISLR | 1.50 | 0.90 | 0.51 | 0.48 | 3.76 |
| ISLR, ALDOA, PRDX1, LG3BP | 1.17 | ISLR | 1.24 | 0.90 | 0.51 | 0.47 | 3.74 |
| ISLR, LG3BP | 1.18 | ISLR | 1.01 | 0.91 | 0.47 | 0.47 | 3.57 |
| ISLR, COIA1, LG3BP | 4.46 | ISLR | 1.43 | 0.91 | 0.47 | 0.48 | 3.30 |
| ISLR, PRDX1, LG3BP | 1.32 | ISLR | 1.46 | 0.91 | 0.47 | 0.46 | 3.28 |
| ISLR, ALDOA, LG3BP | 1.01 | ISLR | 0.89 | 0.90 | 0.45 | 0.46 | 4.91 |
| ALDOA, COIA1, LRP1, LG3BP | 0.83 | COIA1 | 3.18 | 0.90 | 0.45 | 0.46 | 4.01 |
| ISLR, ALDOA, COIA1, PRDX1, LG3BP | 8.97 | ISLR | 2.14 | 0.90 | 0.45 | 0.45 | 3.58 |
| ISLR, COIA1, PRDX1, LG3BP | 20.54 | ISLR | 2.86 | 0.90 | 0.43 | 0.45 | 3.12 |
| ISLR, ALDOA, COIA1, LG3BP | 3.63 | ISLR | 1.27 | 0.90 | 0.38 | 0.44 | 4.71 |
| ISLR, ALDOA, LPR1, LG3BP | 0.95 | ISLR | 2.97 | 0.90 | 0.38 | 0.44 | 3.97 |

All possible panels of proteins ALDOA, COIA1, FRIL, LG3BP, LRP1, PRDX1, TSP1, TETN, and BGH3 are next generated. A set of 27 panels were selected to be carried forward by the following criteria:
Median Specificity >=0.5
Max Coefficient CV<=1.5
Maximum ALPHA CV<=1.5
Cross-validated pAUC at specificity=0.9 greater than one fold random.
A minimum of four proteins per panel.
The top 6 panels were carried forward.

TABLE 3

Top 6 panels

| Panel | Proteins | Size | Median Specificity | Rank | xv_Specificity |
|---|---|---|---|---|---|
| ID_341 | ALDOA, TSP1, FRIL, PRDX1, LG3BP | 5 | 0.62 | 3 | 0.32 |
| ID_85 | TSP1, FRIL, PRDX1, LG3BP | 4 | 0.55 | 5 | 0.31 |
| ID_340 | ALDOA, TSP1, FRIL, PRDX1 | 4 | 0.66 | 1 | 0.29 |
| ID_449 | ALDOA, COIA1, TSP1, LG3BP | 4 | 0.51 | 6 | 0.27 |
| ID_465 | ALDOA, COIA1, TSP1, FRIL, LG3BP | 5 | 0.60 | 4 | 0.24 |
| ID_469 | ALDOA, COIA1, TSP1, FRIL, PRDX1, LG3BP | 6 | 0.64 | 2 | 0.23 |

Figure 2:
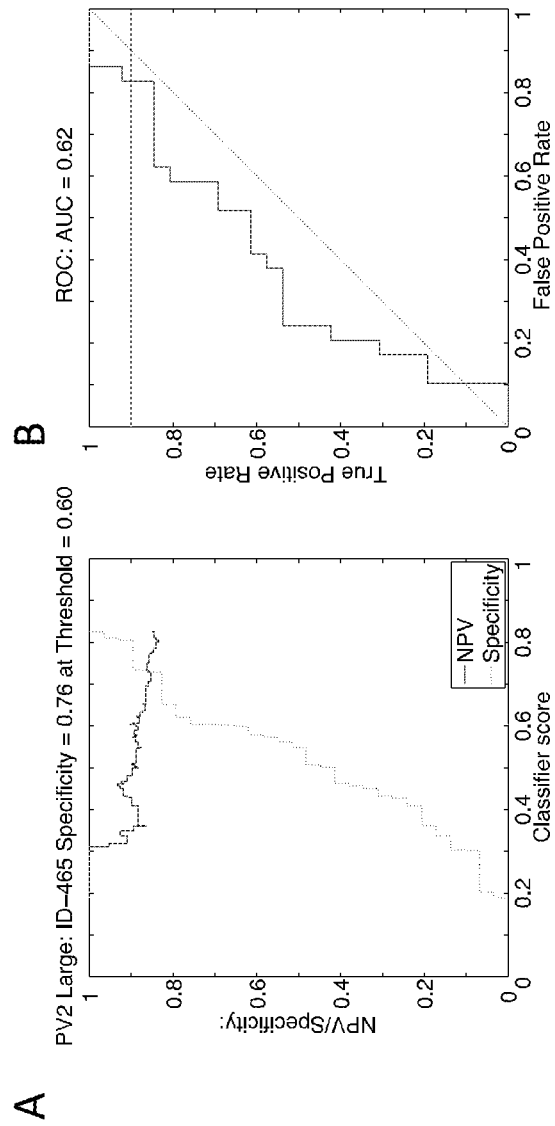
FIG. 2 is a panel of graphs showing A) NPV and specificity of panel ID_465 and B) area under the curve for a receiving operating curve for panel ID_465.
Figure 3:
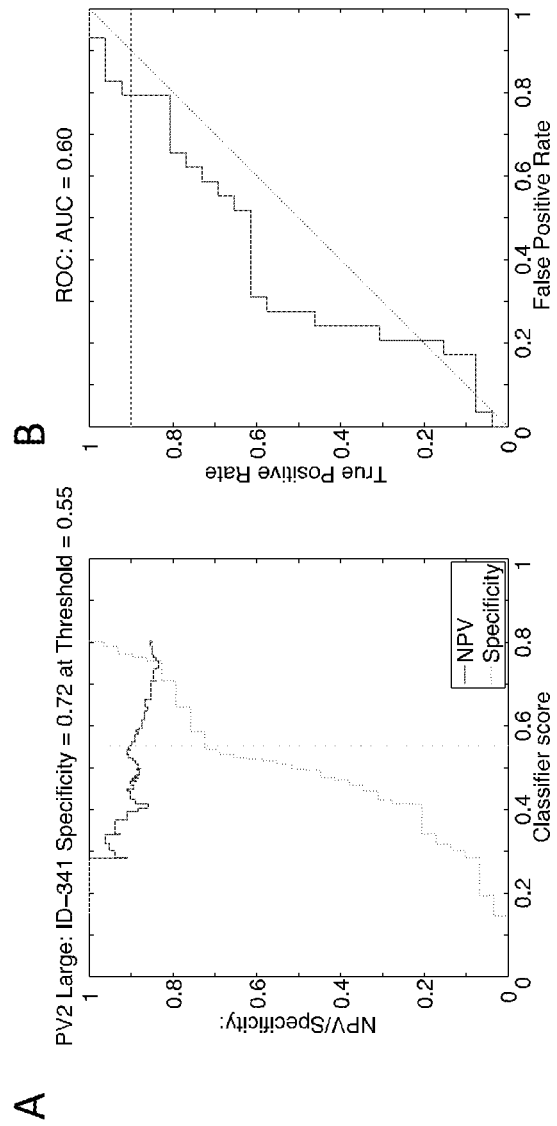
FIG. 3 is a panel of graphs showing A) NPV and specificity of panel ID_341 and B) area under the curve for a receiving operating curve for panel ID_341.
Figure 4:
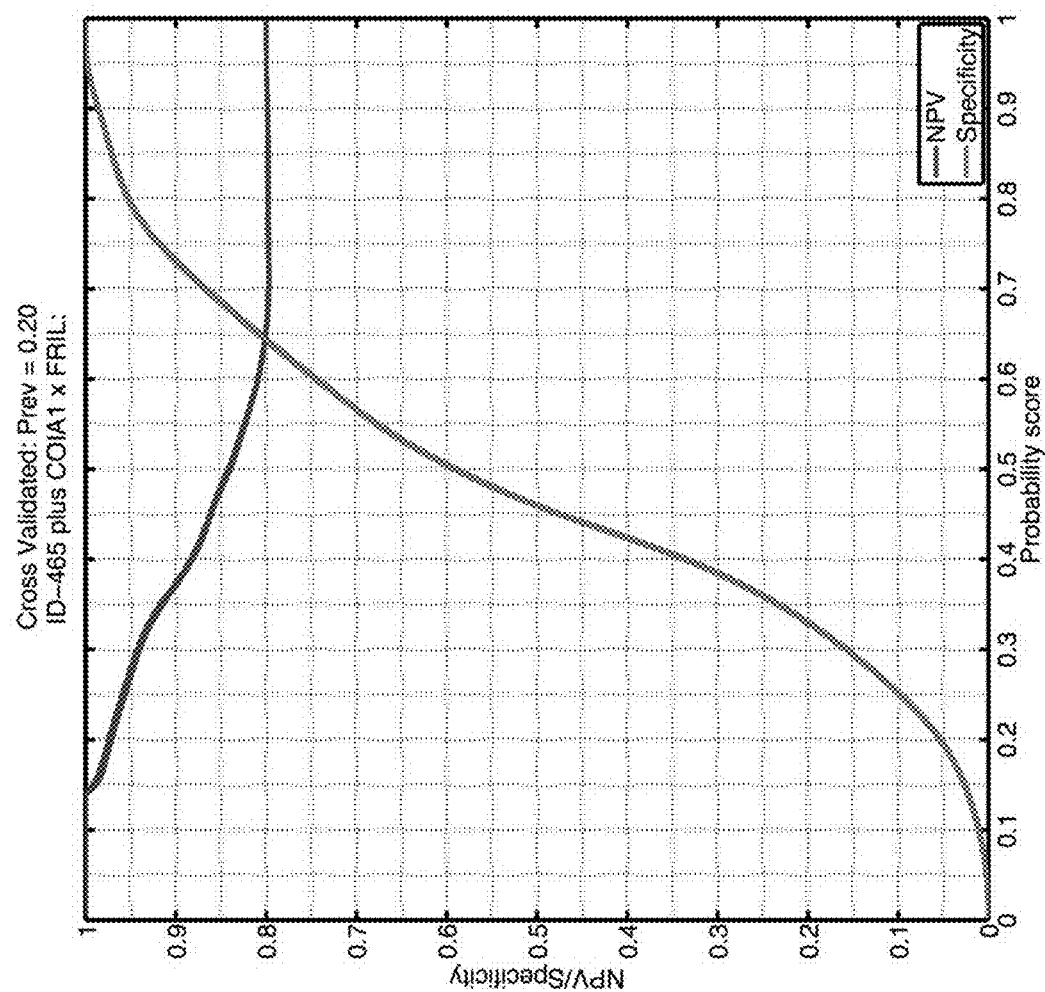
FIG. 4 is a graph showing NPV and specificity of panel ID_465 plus COIA1×FRIL interaction (C4 Classifier).
Figure 5:
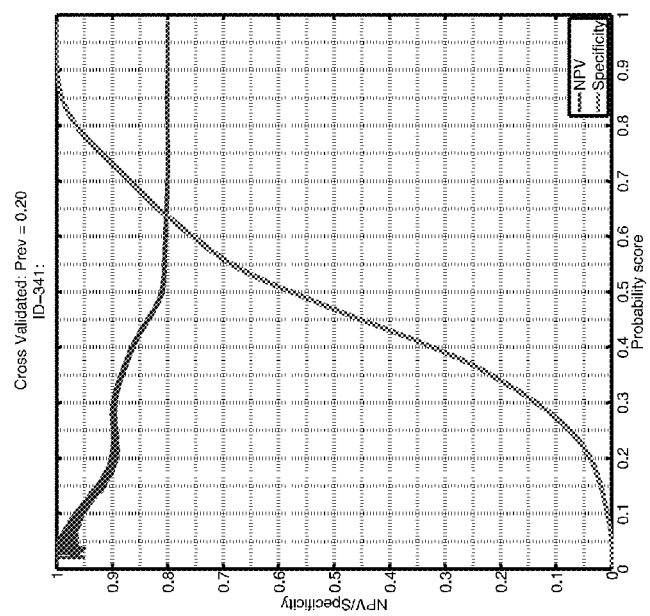
FIG. 5 is a graph showing NPV and specificity of panel ID_341.

Representative NPV/Specificity plot for ID_465 and ID_341 panels can be found in FIGS. 2 and 3, respectively.

All possible interaction pairs were added to panel 465. The cross validated performance (Specificity at NPV=0.90) and partial AUC was measured. The below table displays the performance:

Cross validated performance and partial AUC for panel 465.

| Name | Max_cv | Max_cv_protein | ALPHA_CV | NPV | Median specificity | Median threshold | xv_pAUC_xv | NPV | xv_Spec | xv_Threshold | ID_465 xv-spec | ID465 xv_pAUC |
|---|---|---|---|---|---|---|---|---|---|---|---|---|
| ID_465 ALQASALK (SEQ ID NO: 25)_401.25_6 17.40_times_AVGLAGTFR (SEQ ID NO: 26)_446.26_7 21.40 | 0.981 | Interaction term | 0.429 | 0.901 | 0.617 | 0.483 | 1.751 | 0.900 | 0.182 | 0.346 | 0 | 0 |

| Name | Max_cv | Max_cv_protein | ALPHA_CV | NPV | Median specificity | Median threshold | xv_pAUC_xv | NPV | xv_Spec | xv_Threshold | ID_465 xv-spec | ID465 xv_pAUC |
|---|---|---|---|---|---|---|---|---|---|---|---|---|
| ID_465 ALQASALK (SEQ ID NO: 25)_401.25_617.40_times_GFLLLASLR (SEQ ID NO: 27)_495.31_559.40 | 0.955 | GFLLLASLR (SEQ ID NO: 27)_495.31_559.40 | 0.381 | 0.904 | 0.638 | 0.481 | 1.571 | 0.900 | 0.201 | 0.355 | 0 | 0 |
| ID_465 ALQASALK (SEQ ID NO: 25)_401.25_617.40_times_LGGPEAGLGEYLFER (SEQ ID NO: 28)_804.40_1083.60 | 0.735 | LGGPEAGLGEYLFER (SEQ ID NO: 28)_804.40_1083.60 | 0.529 | 0.901 | 0.681 | 0.501 | 1.944 | 0.900 | 0.240 | 0.375 | 0 | 0 |
| ID_465 ALQASALK (SEQ ID NO: 25)_401.25_617.40_times_VEIFYR (SEQ ID NO: 29)_413.73_598.30 | 0.953 | Interaction term | 0.397 | 0.901 | 0.617 | 0.495 | 2.209 | 0.900 | 0.241 | 0.376 | 0 | 1 |

-continued

| Name | Max_cv | Max_cv_protein | ALPHA_CV | NPV | Median specificity | Median threshold | xv_pAUC_xv | NPV | xv_Spec | xv_Threshold | ID_465 xv-spec | ID465 xv_pAUC |
|---|---|---|---|---|---|---|---|---|---|---|---|---|
| ID_465 AVGLAGTFR (SEQ ID NO: 26)_446.26_721.40_times_GFLLLASLR (SEQ ID NO: 27)_495.31_559.40 | 0.891 | Interaction term | 0.475 | 0.901 | 0.511 | 0.455 | 1.734 | 0.900 | 0.188 | 0.336 | 0 | 0 |
| ID_465 AVGLAGTFR (SEQ ID NO: 26)_446.26_721.40_times_LGGPEAGLGEYLFER (SEQ ID NO: 28)_804.40_1083.60 | 0.466 | LGGPEAGLGEYLFER (SEQ ID NO: 28)_804.40_1083.60 | 0.619 | 0.902 | 0.660 | 0.496 | 2.402 | 0.900 | 0.396 | 0.422 | 1 | 1 |
| ID_465 AVGLAGTFR (SEQ ID NO: 26)_446.26_721.40_times_VEIFYR (SEQ ID NO: 29)_413. | 4.349 | VEIFYR (SEQ ID NO: 29)_413.73_598.30 | 0.510 | 0.905 | 0.574 | 0.481 | 1.643 | 0.900 | 0.216 | 0.360 | 0 | 0 |

-continued

| Name | Max_cv | Max_cv_protein | ALPHA_CV | NPV | Median specificity | Median threshold | xv_pAUC_xv | NPV | xv_Spec | xv_Threshold | ID_465 xv-spec | ID465 xv_pAUC |
|---|---|---|---|---|---|---|---|---|---|---|---|---|
| 73_5 98.30 | | | | | | | | | | | | |
| ID_465 GFLLLASLR (SEQ ID NO: 27)_495. 31_5 59.40_ times_LGPEAGLGEYLFER (SEQ ID NO: 28)_804. 40_1 083.60 | 556.510 | Interaction term | 0.420 | 0.901 | 0.617 | 0.485 | 1.217 | 0.900 | 0.165 | 0.337 | 0 | 0 |
| ID_465 GFLLLASLR (SEQ ID NO: 27)_495. 31_5 59.40_ times_VEIFYR (SEQ ID NO: 29)_413. 73_5 98.30 | 0.806 | AVGLAGTFR (SEQ ID NO: 26)_446.26_721.40 | 0.392 | 0.903 | 0.702 | 0.509 | 1.955 | 0.900 | 0.222 | 0.370 | 0 | 0 |
| ID_465 LGGPEAGLGEYLFER (SEQ ID NO: 28)_804. 40_1 083.60_t imes_VEIFYR (SEQ ID NO: 29)_413. | 0.743 | AVGLAGTFR (SEQ ID NO: 26)_446.26_721.40 | 0.387 | 0.902 | 0.660 | 0.496 | 1.947 | 0.900 | 0.283 | 0.392 | 1 | 0 |

-continued

| Name | Max_cv | Max_cv_protein | ALPHA_CV | NPV | Median specificity | Median threshold | xv_pAUC_xv | NPV | xv_Spec | xv_Threshold | ID_465 xv-spec | ID465 xv_pAUC |
|---|---|---|---|---|---|---|---|---|---|---|---|---|
| 73_5 98.30 | | | | | | | | | | | | |
| ID_4 65 | 0.700 | AVGLAGTFR(SEQ ID NO: 26)_446.26_721.40 | 0.404 | 0.903 | 0.596 | 0.482 | 1.974 | 0.900 | 0.246 | 0.381 | | |

The panel including the interaction term from COIA1 and FRIL performed much better than the panel without interaction terms in both cross validated specificity at NPV=0.9 and cross validated partial AUC.

TABLE 4

C4 Classifier

| Protein | Compound Name | SEQ ID NO: | Precursor Ion | Product Ion | Coefficient |
|---|---|---|---|---|---|
| ALDOA_HUMAN | ALQASALK | 25 | 401.25 | 617.4 | −0.47459794 (Beta) |
| COIA1_HUMAN | AVGLAGTFR | 26 | 446.26 | 721.4 | −2.468073083 (Beta) |
| TSP1_HUMAN | GFLLLASLR | 27 | 495.31 | 559.4 | 0.33223188 (Beta) |
| FRIL_HUMAN | LGGPEAGLGEYLFER | 28 | 804.4 | 1083.6 | −0.864887827 |
| LG3BP_HUMAN | VEIFYR | 29 | 413.73 | 598.3 | −0.903170248 |
| COIA1 × FRIL | Interaction | | | | −1.227671396 |
| ALPHA | Constant | | | | −1.621210001 |

TABLE 5

Performance of C4 Classifier

| Threshold | NPV | Specificity |
|---|---|---|
| 0.48 | 0.85 | 0.55 |
| 0.37 | 0.90 | 0.28 |
| 0.27 | 0.95* | 0.13 |

TABLE 6

Nucleotide sequences of proteins in high performing panels.

| Gene Name | Nucleotide Sequence | Seq. ID. |
|---|---|---|
| ALDOA_HUMAN | ATGCCCTACCAATATCCAGCACTGACCCCGGAGCAGAAGAAGGAGCTGTCT GACATCGCTCACCGCATCGTGGCACCTGGCAAGGGCATCCTGGCTGCAGAT GAGTCCACTGGGAGCATTGCCAAGCGGCTGCAGTCCATTGGCACCGAGAAC ACCGAGGAGAACCGGCGCTTCTACCGCCAGCTGCTGCTGACAGCTGACGAC CGCGTGAACCCCTGCATTGGGGGTGTCATCCTCTTCCATGAGACACTCTAC CAGAAGGCGGATGATGGGCGTCCCTTCCCCCAAGTTATCAAATCCAAGGGC GGTGTTGTGGGCATCAAGGTAGACAAGGGCGTGGTCCCCCTGGCAGGGACA AATGGCGAGACTACCACCCAAGGGTTGGATGGGCTGTCTGAGCGCTGTGCC CAGTACAAGAAGGACGGAGCTGACTTCGCCAAGTGGCGTTGTGTGCTGAAG ATTGGGGAACACACCCCCTCAGCCCTCGCCATCATGGAAAATGCCAATGTT CTGGCCCGTTATGCCAGTATCTGCCAGCAGAATGGCATTGTGCCCATCGTG GAGCCTGAGATCCTCCCTGATGGGGACCATGACTTGAAGCGCTGCCAGTAT GTGACCGAGAAGGTGCTGGCTGCTGTCTACAAGGCTCTGAGTGACCACCAC ATCTACCTGGAAGGCACCTTGCTGAAGCCCAACATGGTCACCCCAGGCCAT GCTTGCACTCAGAAGTTTTCTCATGAGGAGATTGCCATGGCGACCGTCACA GCGCTGCGCCGCACAGTGCCCCCCGCTGTCACTGGGATCACCTTCCTGTCT GGAGGCCAGAGTGAGGAGGAGGCGTCCATCAACCTCAATGCCATTAACAAG TGCCCCCTGCTGAAGCCCTGGGCCCTGACCTTCTCCTACGGCCGAGCCCTG CAGGCCTCTGCCCTGAAGGCCTGGGGCGGGAAGAAGGAGAACCTGAAGGCT GCGCAGGAGGAGTATGTCAAGCGAGCCCTGGCCAACAGCCTTGCCTGTCAA GGAAAGTACACTCCGAGCGGTCAGGCTGGGGCTGCTGCCAGCGAGTCCCTC TTCGTCTCTAACCACGCCTATTAA | 1 |

TABLE 6-continued

Nucleotide sequences of proteins in high performing panels.

| Gene Name | Nucleotide Sequence | Seq. ID. |
|---|---|---|
| ALDOA_HUMAN (isoform 2) | ATGGCAAGGCGCAAGCCAGAAGGGTCCAGCTTCAACATGACCCACCTGTCC ATGGCTATGGCCTTTTCCTTTCCCCCAGTTGCCAGTGGGCAACTCCACCCT CAGCTGGGCAACACCCAGCACCAGACAGAGTTAGGAAAGGAACTTGCTACT ACCAGCACCATGCCCTACCAATATCCAGCACTGACCCCGGAGCAGAAGAAG GAGCTGTCTGACATCGCTCACCGCATCGTGGCACCTGGCAAGGGCATCCTG GCTGCAGATGAGTCCACTGGGAGCATTGCCAAGCGGCTGCAGTCCATTGGC ACCGAGAACACCGAGGAGAACCGGCGCTTCTACCGCCAGCTGCTGCTGACA GCTGACGACCGCGTGAACCCCTGCATTGGGGGTGTCATCCTCTTCCATGAG ACACTCTACCAGAAGGCGGATGATGGGCGTCCCTTCCCCCAAGTTATCAAA TCCAAGGGCGGTGTTGTGGGCATCAAGGTAGACAAGGGCGTGGTCCCCCTG GCAGGGACAAATGGCGAGACTACCACCCAAGGGTTGGATGGGCTGTCTGAG CGCTGTGCCCAGTACAAGAAGGACGGAGCTGACTTCGCCAAGTGGCGTTGT GTGCTGAAGATTGGGGAACACACCCCCTCAGCCCTCGCCATCATGGAAAAT GCCAATGTTCTGGCCCGTTATGCCAGTATCTGCCAGCAGAATGGCATTGTG CCCATCGTGGAGCCTGAGATCCTCCCTGATGGGGACCATGACTTGAAGCGC TGCCAGTATGTGACCGAGAAGGTGCTGGCTGCTGTCTACAAGGCTCTGAGT GACCACCACATCTACCTGGAAGGCACCTTGCTGAAGCCCAACATGGTCACC CCAGGCCATGCTTGCACTCAGAAGTTTTCTCATGAGGAGATTGCCATGGCG ACCGTCACAGCGCTGCGCCGCACAGTGCCCCCCGCTGTCACTGGGATCACC TTCCTGTCTGGAGGCCAGAGTGAGGAGGAGGCGTCCATCAACCTCAATGCC ATTAACAAGTGCCCCCTGCTGAAGCCCTGGGCCCTGACCTTCTCCTACGGC CGAGCCCTGCAGGCCTCTGCCCTGAAGGCCTGGGGCGGGAAGAAGGAGAAC CTGAAGGCTGCGCAGGAGGAGTATGTCAAGCGAGCCCTGGCCAACAGCCTT GCCTGTCAAGGAAAGTACACTCCGAGCGGTCAGGCTGGGGCTGCTGCCAGC GAGTCCCTCTTCGTCTCTAACCACGCCTATTAA | 2 |
| FRIL_HUMAN | ATGAGCTCCCAGATTCGTCAGAATTATTCCACCGACGTGGAGGCAGCCGTC AACAGCCTGGTCAATTTGTACCTGCAGGCCTCCTACACCTACCTCTCTCTG GGCTTCTATTTCGACCGCGATGATGTGGCTCTGGAAGGCGTGAGCCACTTC TTCCGCGAATTGGCCGAGGAGAAGCGCGAGGGCTACGAGCGTCTCCTGAAG ATGCAAAACCAGCGTGGCGGCCGCGCTCTCTTCCAGGACATCAAGAAGCCA GCTGAAGATGAGTGGGGTAAAACCCCAGACGCCATGAAAGCTGCCATGGCC CTGGAGAAAAAGCTGAACCAGGCCCTTTTGGATCTTCATGCCCTGGGTTCT GCCCGCACGGACCCCCATCTCTGTGACTTCCTGGAGACTCACTTCCTAGAT GAGGAAGTGAAGCTTATCAAGAAGATGGGTGACCACCTGACCAACCTCCAC AGGCTGGGTGGCCCGGAGGCTGGGCTGGGCGAGTATCTCTTCGAAAGGCTC ACTCTCAAGCACGACTAA | 3 |
| LG3BP_HUMAN | ATGACCCCTCCGAGGCTCTTCTGGGTGTGGCTGCTGGTTGCAGGAACCCAA GGCGTGAACGATGGTGACATGCGGCTGGCCGATGGGGGCGCCACCAACCAG GGCCGCGTGGAGATCTTCTACAGAGGCCAGTGGGGCACTGTGTGTGACAAC CTGTGGGACCTGACTGATGCCAGCGTCGTCTGCCGGGCCCTGGGCTTCGAG AACGCCACCCAGGCTCTGGGCAGAGCTGCCTTCGGGCAAGGATCAGGCCCC ATCATGCTGGATGAGGTCCAGTGCACGGGAACCGAGGCCTCACTGGCCGAC TGCAAGTCCCTGGGCTGGCTGAAGAGCAACTGCAGGCACGAGAGAGACGCT GGTGTGGTCTGCACCAATGAAACCAGGAGCACCCACACCCTGGACCTCTCC AGGGAGCTCTCGGAGGCCCTTGGCCAGATCTTTGACAGCCAGCGGGGCTGC GACCTGTCCATCAGCGTGAATGTGCAGGGCGAGGACGCCCTGGGCTTCTGT GGCCACACGGTCATCCTGACTGCCAACCTGGAGGCCAGGCCTGTGGAAG GAGCCGGGCAGCAATGTCACCATGAGTGTGGATGCTGAGTGTGTGCCCATG GTCAGGGACCTTCTCAGGTACTTCTACTCCCGAAGGATTGACATCACCCTG TCGTCAGTCAAGTGCTTCCACAAGCTGGCCTCTGCCTATGGGGCCAGGCAG CTGCAGGGCTACTGCGCAAGCCTCTTTGCCATCCTCCTCCCCCAGGACCCC TCGTTCCAGATGCCCCTGGACCTGTATGCCTATGCAGTGGCCACAGGGGAC GCCCTGCTGGAGAAGCTCTGCCTACAGTTCCTGGCCTGGAACTTCGAGGCC TTGACGCAGGCCGAGGCCTGGCCCAGTGTCCCCACAGACCTGCTCCAACTG CTGCTGCCCAGGAGCGACCTGGCGGTGCCCAGCGAGCTGGCCCTACTGAAG GCCGTGGACACCTGGAGCTGGGGGAGCGTGCCTCCCATGAGGAGGTGGAG GGCTTGGTGGAGAAGATCCGCTTCCCCATGATGCTCCCTGAGGAGCTCTTT GAGCTGCAGTTCAACCTGTCCCTGTACTGGAGCCACGAGGCCCTGTTCCAG AAGAAGACTCTGCAGGCCCTGGAATTCCACACTGTGCCCTTCCAGTTGCTG GCCCGGTACAAAGGCCTGAACCTCACCGAGGATACCTACAAGCCCCGGATT TACACCTCGCCCACCTGGAGTGCCTTTGTGACAGACAGTTCCTGGAGTGCA CGGAAGTCACAACTGGTCTATCAGTCCAGACGGGGGCCTTTGGTCAAATAT TCTTCTGATTACTTCCAAGCCCCTCTGACTACAGATACTACCCCTACCAG TCCTTCCAGACTCCACAACACCCCAGCTTCCTCTTCCAGGACAAGAGGGTG TCCTGGTCCCTGGTCTACCTCCCCACCATCCAGAGCTGTGGAACTACGGC TTCTCCTGCTCCTCGGACGAGCTCCCTGTCCTGGGCCTCACCAAGTCTGGC GGCTCAGATCGCACCATTGCCTACGAAAACAAAGCCCTGATGCTCTGCGAA GGGCTCTTCGTGGCAGACGTCACCGATTTCGAGGGCTGGAAGGCTGCGATT CCCAGTGCCCTGGACACCAACAGCTCGAAGAGCACCTCCTCCTTCCCCTGC CCGGCAGGGCACTTCAACGGCTTCCGCACGGTCATCCGCCCCTTCTACCTG ACCAACTCCTCAGGTGTGGACTAG | 4 |

TABLE 6-continued

Nucleotide sequences of proteins in high performing panels.

| Gene Name | Nucleotide Sequence | Seq. ID. |
|---|---|---|
| TSP1_HUMAN | ATGGGGCTGGCCTGGGGACTAGGCGTCCTGTTCCTGATGCATGTGTGTGGC<br>ACCAACCGCATTCCAGAGTCTGGCGGAGACAACAGCGTGTTTGACATCTTT<br>GAACTCACCGGGGCCGCCCGCAAGGGGTCTGGGCGCCGACTGGTGAAGGGC<br>CCCGACCCTTCCAGCCCAGCTTTCCGCATCGAGGATGCCAACCTGATCCCC<br>CCTGTGCCTGATGACAAGTTCCAAGACCTGGTGGATGCTGTGCGGGCAGAA<br>AAGGGTTTCCTCCTTCTGGCATCCCTGAGGCAGATGAAGAAGACCCGGGGC<br>ACGCTGCTGGCCCTGGAGCGGAAAGACCACTCTGGCCAGGTCTTCAGCGTG<br>GTGTCCAATGGCAAGGCGGGCACCCTGGACCTCAGCCTGACCGTCCAAGGA<br>AAGCAGCACGTGGTGTCTGTGGAAGAAGCTCTCCTGGCAACCGGCCAGTGG<br>AAGAGCATCACCCTGTTTGTGCAGGAAGACAGGGCCCAGCTGTACATCGAC<br>TGTGAAAAGATGGAGAATGCTGAGTTGGACGTCCCCATCCAAAGCGTCTTC<br>ACCAGAGACCTGGCCAGCATCGCCAGACTCCGCATCGCAAAGGGGGCGTC<br>AATGACAATTTCCAGGGGGTGCTGCAGAATGTGAGGTTTGTCTTTGGAACC<br>ACACCAGAAGACATCCTCAGGAACAAAGGCTGCTCCAGCTCTACCAGTGTC<br>CTCCTCACCCTTGACAACAACGTGGTGAATGGTTCCAGCCCTGCCATCCGC<br>ACTAACTACATTGGCCACAAGACAAAGGACTTGCAAGCCATCTGCGGCATC<br>TCCTGTGATGAGCTGTCCAGCATGGTCCTGGAACTCAGGGGCCTGCGCACC<br>ATTGTGACCACGCTGCAGGACAGCATCCGCAAAGTGACTGAAGAGAACAAA<br>GAGTTGGCCAATGAGCTGAGGCGGCCTCCCCTATGCTATCACAACGGAGTT<br>CAGTACAGAAATAACGAGGAATGGACTGTTGATAGCTGCACTGAGTGTCAC<br>TGTCAGAACTCAGTTACCATCTGCAAAAAGGTGTCCTGCCCCATCATGCCC<br>TGCTCCAATGCCACAGTTCCTGATGGAGAATGCTGTCCTCGCTGTTGGCCC<br>AGCGACTCTGCGGACGATGGCTGGTCTCCATGGTCCGAGTGGACCTCCTGT<br>TCTACGAGCTGTGGCAATGGAATTCAGCAGCGCGGCCGCTCCTGCGATAGC<br>CTCAACAACCGATGTGAGGGCTCCTCGGTCCAGACACGGACCTGCCACATT<br>CAGGAGTGTGACAAGAGATTTAAACAGGATGGTGGCTGGAGCCACTGGTCC<br>CCGTGGTCATCTTGTTCTGTGACATGTGGTGATGGTGTGATCACAAGGATC<br>CGGCTCTGCAACTCTCCCAGCCCCCAGATGAACGGGAAACCCTGTGAAGGC<br>GAAGCGCGGGAGACCAAAGCCTGCAAGAAAGACGCCTGCCCCATCAATGGA<br>GGCTGGGGTCCTTGGTCACCATGGGACATCTGTTCTGTCACCTGTGGAGGA<br>GGGGTACAGAAACGTAGTCGTCTCTGCAACAACCCCACACCCCAGTTTGGA<br>GGCAAGGACTGCGTTGGTGATGTAACAGAAAACCAGATCTGCAACAAGCAG<br>GACTGTCCAATTGATGGATGCCTGTCCAATCCCTGCTTTGCCGGCGTGAAG<br>TGTACTAGCTACCCTGATGGCAGCTGGAAATGTGGTGCTTGTCCCCCTGGT<br>TACAGTGGAAATGGCATCCAGTGCACAGATGTTGATGAGTGCAAAGAAGTG<br>CCTGATGCCTGCTTCAACCACAATGGAGAGCACCGGTGTGAGAACACGGAC<br>CCCGGCTACAACTGCCTGCCCTGCCCCCCACGCTTCACCGGCTCACAGCCC<br>TTCGGCCAGGGTGTCGAACATGCCACGGCCAACAAACAGGTGTGCAAGCCC<br>CGTAACCCCTGCACGGATGGGACCCACGACTGCAACAAGAACGCCAAGTGC<br>AACTACCTGGGCCACTATAGCGACCCCATGTACCGCTGCGAGTGCAAGCCT<br>GGCTACGCTGGCAATGGCATCATCTGCGGGGAGGACACAGACCTGGATGGC<br>TGGCCCAATGAGAACCTGGTGTGCGTGGCCAATGCGACTTACCACTGCAAA<br>AAGGATAATTGCCCCAACCTTCCCAACTCAGGGCAGGAAGACTATGACAAG<br>GATGGAATTGGTGATGCCTGTGATGATGACGATGACAATGATAAAATTCCA<br>GATGACAGGGACAACTGTCCATTCCATTACAACCCAGCTCAGTATGACTAT<br>GACAGAGATGATGTGGGAGACCGCTGTGACAACTGTCCCTACAACCACAAC<br>CCAGATCAGGCAGACACAGACAACAATGGGGAAGGAGACGCCTGTGCTGCA<br>GACATTGATGGAGACGGTATCCTCAATGAACGGGACAACTGCCAGTACGTC<br>TACAATGTGGACCAGAGAGACACTGATATGGATGGGGTTGGAGATCAGTGT<br>GACAATTGCCCCTTGGAACACAATCCGGATCAGCTGGACTCTGACTCAGAC<br>CGCATTGGAGATACCTGTGACAACAATCAGGATATTGATGAAGATGGCCAC<br>CAGAACAATCTGGACAACTGTCCCTATGTGCCCAATGCCAACCAGGCTGAC<br>CATGACAAAGATGGCAAGGGAGATGCCTGTGACCACGATGATGACAACGAT<br>GGCATTCCTGATGACAAGGACAACTGCAGACTCGTGCCCAATCCCGACCAG<br>AAGGACTCTGACGGCGATGGTCGAGGTGATGCCTGCAAAGATGATTTTGAC<br>CATGACAGTGTGCCAGACATCGATGACATCTGTCCTGAGAATGTTGACATC<br>AGTGAGACCGATTTCCGCCGATTCCAGATGATTCCTCTGGACCCCAAAGGG<br>ACATCCCAAAATGACCCTAACTGGGTTGTACGCCATCAGGGTAAAGAACTC<br>GTCCAGACTGTCAACTGTGATCCTGGACTCGCTGTAGGTTATGATGAGTTT<br>AATGCTGTGGACTTCAGTGGCACCTTCTTCATCAACACCGAAAGGGACGAT<br>GACTATGCTGGATTTGTCTTTGGCTACCAGTCCAGCAGCGCTTTTATGTT<br>GTGATGTGGAAGCAAGTCACCCAGTCCTACTGGGACACCAACCCCACGAGG<br>GCTCAGGGATACTCGGGCCTTTCTGTGAAAGTTGTAAACTCCACCACAGGG<br>CCTGGCGAGCACCTGCGGAACGCCCTGTGGCACACAGGAAACACCCTGGC<br>CAGGTGCGCACCCTGTGGCATGACCCTCGTCACATAGGCTGGAAAGATTTC<br>ACCGCCTACAGATGGCGTCTCAGCCACAGGCCAAAGACGGGTTTCATTAGA<br>GTGGTGATGTATGAAGGGAAGAAAATCATGGCTGACTCAGGACCCATCTAT<br>GATAAAACCTATGCTGGTGGTAGACTAGGGTTGTTTGTCTTCTCTCAAGAA<br>ATGGTGTTCTTCTCTGACCTGAAATACGAATGTAGAGATCCCTAA | 5 |
| CO1A1_HUMAN | ATGTTCAGCTTTGTGGACCTCCGGCTCCTGCTCCTCTTAGCGGCCACCGCC<br>CTCCTGACGCACGGCCAAGAGGAAGGCCAAGTCGAGGGCCAAGACGAAGAC<br>ATCCCACCAATCACCTGCGTACAGAACGGCCTCAGGTACCATGACCGAGAC<br>GTGTGGAAACCCGAGCCCTGCCGGATCTGCGTCTGCGACAACGGCAAGGTG<br>TTGTGCGATGACGTGATCTGTGACGAGACCAAGAACTGCCCCGGCGCCGAA | 6 |

TABLE 6-continued

Nucleotide sequences of proteins in high performing panels.

| Gene Name | Nucleotide Sequence | Seq. ID. |
|---|---|---|
| | GTCCCCGAGGGCGAGTGCTGTCCCGTCTGCCCCGACGGCTCAGAGTCACCC | |
| | ACCGACCAAGAAACCACCGGCGTCGAGGGACCCAAGGGAGACACTGGCCCC | |
| | CGAGGCCCAAGGGGACCCGCAGGCCCCCCTGGCCGAGATGGCATCCCTGGA | |
| | CAGCCTGGACTTCCCGGACCCCCCGGACCCCCCGGACCTCCCGGACCCCCT | |
| | GGCCTCGGAGGAAACTTTGCTCCCCAGCTGTCTTATGGCTATGATGAGAAA | |
| | TCAACCGGAGGAATTTCCGTGCCTGGCCCCATGGGTCCCTCTGGTCCTCGT | |
| | GGTCTCCCTGGCCCCCCTGGTGCACCTGGTCCCCAAGGCTTCCAAGGTCCC | |
| | CCTGGTGAGCCTGGCGAGCCTGGAGCTTCAGGTCCCATGGGTCCCCGAGGT | |
| | CCCCCAGGTCCCCCTGGAAAGAATGGAGATGATGGGGAAGCTGGAAAACCT | |
| | GGTCGTCCTGGTGAGCGTGGGCCTCCTGGGCCTCAGGGTGCTCGAGGATTG | |
| | CCCGGAACAGCTGGCCTCCCTGGAATGAAGGGACACAGAGGTTTCAGTGGT | |
| | TTGGATGGTGCCAAGGGAGATGCTGGTCCTGCTGGTCCTAAGGGTGAGCCT | |
| | GGCAGCCCTGGTGAAAATGGAGCTCCTGGTCAGATGGGCCCCGTGGCCTG | |
| | CCTGGTGAGAGAGGTCGCCCTGGAGCCCCTGGCCCTGCTGGTGCTCGTGGA | |
| | AATGATGGTGCTACTGGTGCTGCCGGGCCCCTGGTCCCACCGGCCCCGCT | |
| | GGTCCTCCTGGCTTCCCTGGTGCTGTTGGTGCTAAGGGTGAAGCTGGTCCC | |
| | CAAGGGCCCCGAGGCTCTGAAGGTCCCCAGGGTGTGCGTGGTGAGCCTGGC | |
| | CCCCCTGGCCCTGCTGGTGCTGCTGGCCCTGCTGGAAACCCTGGTGCTGAT | |
| | GGACAGCCTGGTGCTAAAGGTGCCAATGGTGCTCCTGGTATTGCTGGTGCT | |
| | CCTGGCTTCCCTGGTGCCCGAGGCCCCTCTGGACCCCAGGGCCCCGGCGGC | |
| | CCTCCTGGTCCCAAGGGTAACAGCGGTGAACCTGGTGCTCCTGGCAGCAAA | |
| | GGAGACACTGGTGCTAAGGGAGAGCCTGGCCCTGTTGGTGTTCAAGGACCC | |
| | CCTGGCCCTGCTGGAGAGGAAGGAAAGCGAGGAGCTCGAGGTGAACCCGGA | |
| | CCCACTGGCCTGCCCGGACCCCCTGGCGAGCGTGGTGGACCTGGTAGCCGT | |
| | GGTTTCCCTGGCGCAGATGGTGTTGCTGGTCCCAAGGGTCCCGCTGGTGAA | |
| | CGTGGTTCTCCTGGCCCTGCTGGCCCCAAAGGATCTCCTGGTGAAGCTGGT | |
| | CGTCCCGGTGAAGCTGGTCTGCCTGGTGCCAAGGGTCTGACTGGAAGCCCT | |
| | GGCAGCCCTGGTCCTGATGGCAAAACTGGCCCCCCTGGTCCCGCCGGTCAA | |
| | GATGGTCGCCCCGGACCCCCAGGCCCACCTGGTGCCCGTGGTCAGGCTGGT | |
| | GTGATGGGATTCCCTGGACCTAAAGGTGCTGCTGGAGAGCCCGGCAAGGCT | |
| | GGAGAGCGAGGTGTTCCCGGACCCCCTGGCGCTGTCGGTCCTGCTGGCAAA | |
| | GATGGAGAGGCTGGAGCTCAGGGACCCCCTGGCCCTGCTGGTCCCGCTGGC | |
| | GAGAGAGGTGAACAAGGCCCTGCTGGCTCCCCCGGATTCCAGGGTCTCCCT | |
| | GGTCCTGCTGGTCCTCAGGTGAAGCAGGCAAACCTGGTGAACAGGGTGTT | |
| | CCTGGAGACCTTGGCGCCCCTGGCCCCTCTGGAGCAAGAGGCGAGAGAGGT | |
| | TTCCCTGGCGAGCGTGGTGTGCAAGGTCCCCCTGGTCCTGCTGGTCCCCGA | |
| | GGGGCCAACGGTGCTCCCGGCAACGATGGTGCTAAGGGTGATGCTGGTGCC | |
| | CCTGGAGCTCCCGGTAGCCAGGGCGCCCCTGGCCTTCAGGGAATGCCTGGT | |
| | GAACGTGGTGCAGCTGGTCTTCCAGGGCCTAAGGGTGACAGAGGTGATGCT | |
| | GGTCCCAAAGGTGCTGATGGCTCTCCTGGCAAAGATGGCGTCCGTGGTCTG | |
| | ACTGGCCCCATTGGTCCTCCTGGCCCTGCTGGTGCCCCTGGTGACAAGGGT | |
| | GAAAGTGGTCCCAGCGGCCCTGCTGGTCCCACTGGAGCTCGTGGTGCCCCC | |
| | GGAGACCGTGGTGAGCCTGGTCCCCCGGCCCTGCTGGCTTTGCTGGCCCC | |
| | CCTGGTGCTGACGGCCAACCTGGTGCTAAAGGCGAACCTGGTGATGCTGGT | |
| | GCTAAAGGCGATGCTGGTCCCCCTGGCCCTGCCGGACCCGCTGGACCCCCT | |
| | GGCCCCATTGGTAATGTTGGTGCTCCTGGAGCCAAAGGTGCTCGCGGCAGC | |
| | GCTGGTCCCCCTGGTGCTACTGGTTTCCCTGGTGCTGCTGGCCGAGTCGGT | |
| | CCTCCTGGCCCCTCTGGAAATGCTGGACCCCCTGGCCCTCCTGGTCCTGCT | |
| | GGCAAAGAAGGCGGCAAAGGTCCCCGTGGTGAGACTGGCCCTGCTGGACGT | |
| | CCTGGTGAAGTTGGTCCCCCTGGTCCCCCTGGCCCTGCTGGCGAGAAAGGA | |
| | TCCCCTGGTGCTGATGGTCCTGCTGGTGCTCCTGGTACTCCCGGGCCTCAA | |
| | GGTATTGCTGGACAGCGTGGTGTGGTCGGCCTGCCTGGTCAGAGAGGAGAG | |
| | AGAGGCTTCCCTGGTCTTCCTGGCCCCTCTGGTGAACCTGGCAAACAAGGT | |
| | CCCTCTGGAGCAAGTGGTGAACGTGGTCCCCCTGGTCCCATGGGCCCCCT | |
| | GGATTGCTGGACCCCCTGGTGAATCTGGACGTGAGGGGCTCCTGGTGCC | |
| | GAAGGTTCCCCTGGACGAGACGGTTCTCCTGGCGCCAAGGGTGACCGTGGT | |
| | GAGACCGGCCCCGCTGGACCCCCTGGTGCTCCTGGTGCTCCTGGTGCCCCT | |
| | GGCCCCGTTGGCCCTGCTGGCAAGAGTGGTGATCGTGGTGAGACTGGTCCT | |
| | GCTGGTCCCACCGGTCCTGTCGGCCCTGTTGGCGCCCGTGGCCCCGCCGGA | |
| | CCCCAAGGCCCCCGTGGTGACAAGGGTGAGACAGGCGAACAGGGCGACAGA | |
| | GGCATAAAGGGTCACCGTGGCTTCTCTGGCCTCCAGGGTCCCCCTGGCCCT | |
| | CCTGGCTCTCCTGGTGAACAAGGTCCCTCTGGAGCCTCTGGTCCTGCTGGT | |
| | CCCCGAGGTCCCCCTGGCTCTGCTGGTGCTCCTGGCAAAGATGGACTCAAC | |
| | GGTCTCCCTGGCCCCATTGGGCCCCCTGGTCCTCGCGGTCGCACTGGTGAT | |
| | GCTGGTCCTGTTGGTCCCCCGGCCCTCCTGGACCTCCTGGTCCCCCTGGT | |
| | CCTCCCAGCGCTGGTTTCGACTTCAGCTTCCTGCCCCAGCCACCTCAAGAG | |
| | AAGGCTCACGATGGTGGCCGCTACTACCGGGCTGATGATGCCAATGTGGTT | |
| | CGTGACCGTGACCTCGAGGTGGACACCACCCTCAAGAGCCTGAGCCAGCAG | |
| | ATCGAGAACATCCGGAGCCCAGAGGGCAGCCGCAAGAACCCCGCCCGCACC | |
| | TGCCGTGACCTCAAGATGTGCCACTCTGACTGGAAGAGTGGAGAGTACTGG | |
| | ATTGACCCCAACCAAGGCTGCAACCTGGATGCCATCAAAGTCTTCTGCAAC | |
| | ATGGAGACTGGTGAGACCTGCGTGTACCCCACTCAGCCCAGTGTGGCCCAG | |
| | AAGAACTGGTACATCAGCAAGAACCCCAAGGACAAGAGGCATGTCTGGTTC | |
| | GGCGAGAGCATGACCGATGGATTCCAGTTCGAGTATGGCGGCCAGGGCTCC | |
| | GACCCTGCCGATGTGGCCATCCAGCTGACCTTCCTGCGCCTGATGTCCACC | |

TABLE 6-continued

Nucleotide sequences of proteins in high performing panels.

| Gene Name | Nucleotide Sequence | Seq. ID. |
|---|---|---|
| | GAGGCCTCCCAGAACATCACCTACCACTGCAAGAACAGCGTGGCCTACATG GACCAGCAGACTGGCAACCTCAAGAAGGCCCTGCTCCTCCAGGGCTCCAAC GAGATCGAGATCCGCGCCGAGGGCAACAGCCGCTTCACCTACAGCGTCACT GTCGATGGCTGCACGAGTCACACCGGAGCCTGGGGCAAGACAGTGATTGAA TACAAAACCACCAAGACCTCCCGCCTGCCCATCATCGATGTGGCCCCCTTG GACGTTGGTGCCCCAGACCAGGAATTCGGCTTCGACGTTGGCCCTGTCTGC TTCCTGTAA | |

TABLE 7

Amino acid sequences of proteins in high performing panels.

| Protein Name | Amino Acid Sequence | Seq. ID. |
|---|---|---|
| ALDOA_HUMAN | MPYQYPALTPEQKKELSDIAHRIVAPGKGILAADESTGSIAKRLQSIGTEN TEENRRFYRQLLLTADDRVNPCIGGVILFHETLYQKADDGRPFPQVIKSKG GVVGIKVDKGVVPLAGTNGETTTQGLDGLSERCAQYKKDGADFAKWRCVLK IGEHTPSALAIMENANVLARYASICQQNGIVPIVEPEILPDGDHDLKRCQY VTEKVLAAVYKALSDHHIYLEGTLLKPNMVTPGHACTQFKSHEEIAMATVT ALRRTVPPAVTGITFLSGGQSEEEASINLNAINKCPLLKPWALTFSYGRAL QASALKAWGGKKENLKAAQEEYVKRALANSLACQGKYTPSGQAGAAASESL FVSNHAY | 7 |
| ALDOA_HUMAN (isoform 2) | MARRKPEGSSFNMTHLSMAMAFSFPFVASGQLHPQLGNTQHQTELGKELAT TSTMFYQYPALTPEQKKELSDIAERIVAPGKGILAADESTGSIAKRLQSIG TENTEENRRFYRQLLLTADDRVNPCIGGVILFHETLYQKADDGRPFPQVIK SKGGVVGIKVDKGVVPLAGTNGETTTQGLDGLSERCAQYKKDGADFAKWRC VLKIGEHTPSALAIMENANVLARYASICQQNGIVPIVEPEILPDGDHDLKR CQYVTEKVLAAVYKALSDHHIYLEGTLLKPNMVTPGHACTQFKSHEEIAMA TVTALRRTVPPAVTGITFLSGGQSEEEASINLNAINKCPLLKPWALTFSYG RALQASALKAWGGKKENLKAAQEEYVKRALANSLACQGKYTPSGQAGAAAS ESLFVSNHAY | 8 |
| FRIL_HUMAN | MSSQIRQNYSTDVEAAVNSLVNLYLQASYTYLSLGFYFDRDDVALEGVSHF FRELAEEKREGYERLLKMQNQRGGRALFQDIKKPAEDEWGKTPDAMKAAMA LEKKLNQALLDLHALGSARTDPHLCDFLETHFLDEEVKLIKKMGDHLTNLH RLGGPEAGLGEYLFERLTLKHD | 9 |
| LG3BP_HUMAN | MTPPRLFWVWLLVAGTQGVNDGDMRLADGGATNQGRVEIFYRGQWGTVCDN LWDLTDASVVCRALGFENATQALGRAAFGQGSGPIMLDEVQCTGTEASLAD CKSLGWLKSNCRHERDAGVVCTNETRSTHTLDLSRELSEALGQIFDSQRGC DLSISVNVQGEDALGFCGHTVILTANLEAQALWKEPGSNVTMSVDAECVPM VRDLLRYFYSRRIDITLSSVKCFHKLASAYGARQLQGYCASLFAILLPQDP SFQMPLDLYAYAVATGDALLEKLCLQFLAWNFEALTQAEAWPSVPTDLLQL LLPRSDLAVPSELALLKAVDTWSWGERASHEEVEGLVEKIRFPMMLPEELF ELQFNLSLYWSHEALFQKKTLQALEFHTVPFQLLARYKGLNLTEDTYKPRI YTSPTWSAFVTDSSWSARKSQLVYQSRRGPLVKYSSDYFQAPSDYRYYPYQ SFQTPQHPSFLFQDKRVSWSLVYLPTIQSCWNYGFSCSSDELPVLGLTKSG GSDRTIAYENKALMLCEGLFVADVTDFEGWKAAIPSALDTNSSKSTSSFPC PAGHFNGFRTVIRPFYLTNSSGVD | 10 |
| TSP1_HUMAN | MGLAWGLGVLFLMHVCGTNRIPESGGDNSVFDIFELTGAARKGSGRRLVKG PDPSSPAFRIEDANLIPPVPDDKFQDLVDAVRAEKGFLLLASLRQMKKTRG TLLALERKDHSGQVFSVVSNKAGTLDLSLTVQGKQHVVSVEEALLATGQW KSITLFVQEDRAQLYIDCEKMENAELDVPIQSVFTRDLASIARLRIAKGGV NDNFQGVLQNVRFVFGTTPEDILRNKGCSSSTSVLLTLDNNVVNGSSPAIR TNYIGHKTKDLQAICGISCDELSSMVLELRGLRTIVTTLQDSIRKVTEENK ELANELRRPPLCYHNGVQYRNNEEWTVDSCTECHCQNSVTICKKVSCPIMP CSNATVPDGECCPRCWPSDSADDGWSPWSEWTSCSTSCGNGIQQRGRSCDS LNNRCEGSSVQTRTCHIQECDKRFKQDGGWSHWSPWSSCSVTCGDGVITRI RLCNSPSPQMNGKPCEGEARETKACKKDACPINGGWGPWSPWDICSVTCGG GVQKRSRLCNNPTPQFGGKDCVGDVTENQICNKQDCPIDGCLSNPCFAGVK CTSYPDGSWKCGACPPGYSGNGIQCTDVDECKEVPDACFNHNGEHRCENTD PGYNCLPCPPRFTGSQPFGQGVEHATANKQVCKPRNPCTDGTHDCNKNAKC NYLGHYSDPMYRCECKPGYAGNGIICGEDTDLDGWPNENLVCVANATYHCK KDNCPNLPNSGQEDYDKDGIGDACDDDDDNDKIPDDRDNCPFHYNPAQYDY DRDDVGDRCDNCPYNHNPDQADTDNNGEGDACAADIDGDGILNERDNCQYV YNVDQRDTDMDGVGDQCDNCPLEHNPDQLDSDSDRIGDTCDNNQDIDEDGH QNNLDNCPYVPNANQADHDKDGKGDACHDDDNDGIPDDKDNCRLVPNPDQ KDSDGDRGDACKDDFDHDSVPDIDDICPENVDISETDFRRFQMIPLDPKG TSQNDPNWVVRHQGKELVQTVNCDPGLAVGYDEFNAVDFSGTFFINTERDD | 11 |

TABLE 7-continued

Amino acid sequences of proteins in high performing panels.

| Protein Name | Amino Acid Sequence | Seq. ID. |
|---|---|---|
| | DYAGFVFGYQSSSRFYVVMWKQVTQSYWDTNPTRAQGYSGLSVKVVNSTTG PGEHLRNALWHTGNTPGQVRTLWHDPRHIGWKDFTAYRWRLSHRPKTGFIR VVMYEGKKIMADSGPIYDKTYAGGRLGLFVFSQEMVFFSDLKYECRDP | |
| CO1A1_HUMAN | MFSFVDLRLLLLLAATALLTHGQEEGQVEGQDEDIPPITCVQNGLRYHDRD VWKPEPCRICVCDNGKVLCDDVICDETKNCPGAEVPEGECCPVCPDGSESP TDQETTGVEGPKGDTGPRGPRGPAGPPGRDGIPGQPGLPGPPGPPGPPGPP GLGGNFAPQLSYGYDEKSTGGISVPGPMGPSGPRGLPGPPGAPGPGGFGGP PGEPGEPGASGPMGPRGPPGPPGKNGDDGEAGKPGRPGERGPPGPGQARGL PGTAGLPGMKGHRGFSGLDGAKGDAGPAGPKGEPGSPGENGAPGQMGPRGL PGERGRPGAPGPAGARGNDGATGAAGPPGPTGPAGPPGFPGAVGAKGEAGP QGPRGSEGPOGVRGEPGPPGPAGAAGPAGNPGADGQPGAKGANGAPGIAGA PGFPGARGPSGPQGPGGPPGPKGNSGEPGAPGSKGDTGAKGEPGPVGVQGP PGPAGEEGKRGARGEPGPTGLPGPPGERGGPGSRGFPGADGVAGPKGPAGE RGSPGPAGPKGSPGEAGRPGEAGLPGAKGLTGSPGSPGPDGKTGPPGPAGQ DGRPGPPGPPGARGQAGVMGFPGPKGAAGEPGKAGERGVPGPPGAVGPAGK DGEAGAQGPPGPAGPAGERGEQGPAGSPGFQGLPGPAGPPGEAGKPGEQGV PGDLGAPGPSGARGERGFPGERGVQGPPGPAGPRGANGAPGNDGAKGDAGA PGAPGSQGAPGLQGMPGERGAAGLPGPKGDRGDAGPKGADGSPGKDGVRGL TGPIGPPGPAGAPGDKGESGPSGPAGPTGARGAPGDRGEPGPPGPAGFAGP PGADGQPGAKGEPGDAGAKGDAGPPGPAGPAGPPGPIGNVGAPGAKGARGS AGPPGATGFPGAAGRVGPPGPSGNAGPPGPPGAGKEGGKGPRGETGPAGR PGEVGPPGPPGPAGEKGSPGADGPAGAPGTPGPQGIAGQRGVVGLPGQRGE RGFPGLPGPSGEPGKQGPSGASGERGPPGPMGPPGLAGPPGESGREGAPGA EGSPGRDGSPGAKGDRGETGPAGPPGAPGAPGAPGPVGPAGKSGDRGETGP AGPTGPVGPVGARGPAGPQGPRGDKGETGEQGDRGIKGHRGFSGLQGPPGP PGSPGEQGPSGASGPAGPRGPPGSAGAPGKDGLNGLPGPIGPPGPRGRTGD AGPVGPPGPPGPPGPPSAGFDFSFLPQPPQEKAHDGGRYYRADDANVV RDRDLEVDTTLKSLSQQIENIRSPEGSRKNPARTCRDLKMCHSDWKSGEYW IDPNQGCNLDAIKVFCNMETGETCVYPTQPSVAQKNWYISKNPKDKRHVWF GESMTDGFQFEYGGQGSDPADVAIQLTFLRLMSTEASQNITYHCKNSVAYM DQQTGNLKKALLLQGSNEIEIRAEGNSRFTYSVTVDGCTSHTGAWGKTVIE YKTTKTSRLPIIDVAPLDVGAPDQEFGEDVGPVCFL | 12 |

TABLE 8

Nucleotide sequences of normalizer proteins in panel.

| Gene Name | Nucleotide Sequence | Seq. ID. |
|---|---|---|
| PEDF_HUMAN | ATGCAGGCCCTGGTGCTACTCCTCTGCATTGGAGCCCTCCTCGGGCACAGC AGCTGCCAGAACCCTGCCAGCCCCCGGAGGAGGGCTCCCCAGACCCCGAC AGCACAGGGCGCTGGTGGAGGAGGAGGATCCTTTCTTCAAAGTCCCCGTG AACAAGCTGGCAGCGGCTGTCTCCAACTTCGGCTATGACCTGTACCGGGTG CGATCCAGCACGAGCCCCACGACCAACGTGCTCCTGTCTCCTCTCAGTGTG GCCACGGCCCTCTCGGCCCTCTCGCTGGGAGCGGAGCAGCGAACAGAATCC ATCATTCACCGGGCTCTCTACTATGACTTGATCAGCAGCCCAGACATCCAT GGTACCTATAAGGAGCTCCTTGACACGGTCACTGCCCCCCAGAAGAACCTC AAGAGTGCCTCCCGGATCGTCTTTGAGAAGAAGCTGCGCATAAAATCCAGC TTTGTGGCACCTCTGGAAAAGTCATATGGGACCAGGCCCAGGTCCTGACG GGCAACCCTCGCTTGGACCTGCAAGAGATCAACAACTGGGTGCAGGCGCAG ATGAAAGGGAAGCTCGCCAGGTCCACAAAGGAAATTCCCGATGAGATCAGC ATTCTCCTTCTCGGTGTGGCGCACTTCAAGGGGCAGTGGGTAACAAAGTTT GACTCCAGAAAGACTTCCCTCGAGGATTTCTACTTGGATGAAGAGAGGACC GTGAGGGTCCCCATGATGTCGGACCCTAAGGCTGTTTTACGCTATGGCTTG GATTCAGATCTCAGCTGCAAGATTGCCCAGCTGCCCTTGACCGGAAGCATG AGTATCATCTTCTTCCTGCCCCTGAAAGTGACCCAGAATTTGACCTTGATA GAGGAGAGCCTCACCTCCGAGTTCATTCATGACATAGACCGGAGAACTGAAG ACCGTGCAGGCGGTCCTCACTGTCCCCAAGCTGAAGCTGAGTTATGAAGGC GAAGTCACCAAGTCCCTGCAGGAGATGAAGCTGCAATCCTTGTTTGATTCA CCAGACTTTAGCAAGATCACAGGCAAACCCATCAAGCTGACTCAGGTGGAA CACCGGGCTGGCTTTGAGTGGAACGAGGATGGGGCGGGAACCACCCCAGC CCAGGGCTGCAGCCTGCCCACCTCACCTTCCCGCTGGACTATCACCTTAAC CAGCCTTTCATCTTCGTACTGAGGGACACAGACACAGGGCCCTTCTCTTC ATTGGCAAGATTCTGGACCCCAGGGGCCCCTAA | 13 |
| MASP1_HUMAN | ATGAGGTGGCTGCTTCTCTATTATGCTCTGTGCTTCTCCCTGTCAAAGGCT TCAGCCCACACCGTGGAGCTAAACAATATGTTTGGCCAGATCCAGTCGCCT GGTTATCCAGACTCCTATCCCAGTGATTCAGAGGTGACTTGGAATATCACT GTCCCAGATGGGTTTCGGATCAAGCTTTACTTCATGCACTTCAACTTGGAA TCCTCCTACCTTTGTGAATATGACTATGTGAAGGTAGAAACTGAGGACCAG | 14 |

TABLE 8-continued

Nucleotide sequences of normalizer proteins in panel.

| Gene Name | Nucleotide Sequence | Seq. ID. |
|---|---|---|
| | GTGCTGGCAACCTTCTGTGGCAGGGAGACCACAGACACAGAGCAGACTCCC<br>GGCCAGGAGGTGGTCCTCTCCCTGGCTCCTTCATGTCCATCACTTTCCGG<br>TCAGATTTCTCCAATGAGGAGCGTTTCACAGGCTTTGATGCCCACTACATG<br>GCTGTGGATGTGGACGAGTGCAAGGAGAGGGAGGACGAGGAGCTGTCCTGT<br>GACCACTACTGCCACAACTACATTGGCGGCTACTACTGCTCCTGCCGCTTC<br>GGCTACATCCTCCACACAGACAACAGGACCTGCCGAGTGGAGTGCAGTGAC<br>AACCTCTTCACTCAAAGGACTGGGGTGATCACCAGCCCTGACTTCCCAAAC<br>CCTTACCCCAAGAGCTCTGAATGCCTGTATACCATCGAGCTGGAGGAGGGT<br>TTCATGGTCAACCTGCAGTTTGAGGACATATTTGACATTGAGGACCATCCT<br>GAGGTGCCCTGCCCCTATGACTACATCAAGATCAAAGTTGGTCCAAAAGTT<br>TTGGGGCCTTTCTGTGGAGAGAAAGCCCCAGAACCCATCAGCACCCAGAGC<br>CACAGTGTCCTGATCCTGTTCCATAGTGACAACTCGGGAGAGAACCGGGGC<br>TGGAGGCTCTCATACAGGGCTGCAGGAAATGAGTGCCCAGAGCTACAGCCT<br>CCTGTCCATGGGAAAATCGAGCCCTCCCAAGCCAAGTATTTCTTCAAAGAC<br>CAAGTGCTCGTCAGCTGTGACACAGGCTACAAAGTGCTGAAGGATAATGTG<br>GAGATGGACACATTCCAGATTGAGTGTCTGAAGGATGGGACGTGGAGTAAC<br>AAGATTCCCACCTGTAAAATTGTAGACTGTAGAGCCCCAGGAGAGCTGGAA<br>CACGGGCTGATCACCTTCTCTACAAGGAACAACCTCACCACATACAAGTCT<br>GAGATCAAATACTCCTGTCAGGAGCCCTATTACAAGATGCTAACAATAAC<br>ACAGGTATATATACCTGTTCTGCCCAAGGAGTCTGGATGAATAAAGTATTG<br>GGGAGAAGCCTACCCACCTGCCTTCCAGTGTGTGGGCTCCCAAGTTCTCC<br>CGGAAGCTGATGGCCAGGATCTTCAATGGACGCCCAGCCCAGAAAGGCACC<br>ACTCCCTGGATTGCCATGCTGTCACACCTGAATGGGCAGCCCTTCTGCGGA<br>GGCTCCCTTCTAGGCTCCAGCTGGATCGTGACCGCCGCACACTGCCTCCAC<br>CAGTCACTCGATCGGAAGATCCGACCCTACGTGATTCAGACTTGCTCAGC<br>CCTTCTGACTTCAAAATCATCCTGGGCAAGCATTGGAGGCTCCGGTCAGAT<br>GAAAATGAACAGCATCTCGGCGTCAAACACACCACTCTCCACCCCCAGTAT<br>GATCCCAACACATTCGAGAATGACGTGGCTCTGGTGGAGCTGTTGGAGAGC<br>CCAGTGCTGAATGCCTTCGTGATGCCCATCTGTCTGCCTGAGGGACCCCAG<br>CAGGAAGGAGCCATGGTCATCGTCAGCGGCTGGGGGAAGCAGTTCTTGCAA<br>AGGTTCCCAGAGACCCTGATGGAGATTGAAATCCCGATTGTTGACCACAGC<br>ACCTGCCAGAAGGCTTATGCCCCGCTGAAGAAGAAAGTGACCAGGGACATG<br>ATCTGTGCTGGGGAGAAGGAAGGGGGAAAGGACGCCTGTGCGGGTGACTCT<br>GGAGGCCCCATGGTGACCCTGAATAGAGAAAGAGGCCAGTGGTACCTGGTG<br>GGCACTGTGTCCTGGGGTGATGACTGTGGGAAGAAGGACCGCTACGGAGTA<br>TACTCTTACATCCACCACAACAAGGACTGGATCCAGAGGGTCACCGGAGTG<br>AGGAACTGA | |
| GELS_HUMAN | ATGGCTCCGCACCGCCCCGCGCCCGCGCTGCTTTGCGCGCTGTCCCTGGCG<br>CTGTGCGCGCTGTCGCTGCCCGTCCGCGCGGCCACTGCGTCGCGGGGGCG<br>TCCCAGGCGGGGCGCCCCAGGGGCGGGTGCCCGAGGCGCGGCCCAACAGC<br>ATGGTGGTGGAACACCCCGAGTTCCTCAAGGCAGGGAAGGAGCCTGGCCTG<br>CAGATCTGGCGTGTGGAGAAGTTCGATCTGGTGCCCGTGCCCACCAACCTT<br>TATGGAGACTTCTTCACGGGCGACGCCTACGTCATCCTGAAGACAGTGCAG<br>CTGAGGAACGGAAATCTGCAGTATGACCTCCACTACTGGCTGGGCAATGAG<br>TGCAGCCAGGATGAGAGCGGGGCGGCCGCCATCTTTACCGTGCAGCTGGAT<br>GACTACCTGAACGGCCGGGCCGTGCAGCACCGTGAGGTCCAGGGCTTCGAG<br>TCGGCCACCTTCCTAGGCTACTTCAAGTCTGGCCTGAAGTACAAGAAAGGA<br>GGTGTGGCATCAGGATTCAAGCACGTGGTACCCAACGAGGTGGTGGTGCAG<br>AGACTCTTCCAGGTCAAAGGGCGGCGTGTGGTCCGTGCCACCGAGGTACCT<br>GTGTCCTGGGAGAGCTTCAACAATGGCGACTGCTTCATCCTGGACCTGGGC<br>AACAACATCCACCAGTGGTGTGGTTCCAACAGCAATCGGTATGAAAGACTG<br>AAGGCCACACAGGTGTCCAAGGGCATCCGGGACAACGAGCGGAGTGGCCGG<br>GCCCGAGTGCACGTGTCTGAGGAGGGCACTGAGCCCGAGGCGATGCTCCAG<br>GTGCTGGGCCCCAAGCCGGCTCTGCCTGCAGGTACCGAGGACACCGCCAAG<br>GAGGATGCGGCCAACCGCAAGCTGGCCAAGCTCTACAAGGTCTCCAATGGT<br>GCAGGGACCATGTCCGTCTCCCTCGTGGCTGATGAGAACCCCTTCGCCCAG<br>GGGGCCCTGAAGTCAGAGGACTGCTTCATCCTGGACACGGCAAAGATGGG<br>AAAATCTTTGTCTGGAAAGGCAAGCAGGCAAACACGGAGGAGAGGAAGGCT<br>GCCCTCAAAACAGCCTCTGACTTCATCACCAAGATGGACTACCCCAAGCAG<br>ACTCAGGTCTCGGTCCTTCCTGAGGGCGGTGAGACCCCACTGTTCAAGCAG<br>TTCTTCAAGAACTGGCGGGACCCAGACCAGACAGATGGCCTGGCTTGTCC<br>TACCTTTCCAGCCATATCGCCAACGTGGAGCGGGTGCCCTTCGACGCCGCC<br>ACCCTGCACACCTCCACTGCCATGGCCGCCCAGCACGGCATGGATGACGAT<br>GGCACAGGCCAGAAACAGATCTGGAGAATGAAGGTTCCAACAAGGTGCCC<br>GTGGACCCTGCCACATATGGACAGTTCTATGAGGCGACAGCTACATCATT<br>CTGTACAACTACCGCCATGGTGGCCGCCAGGGGCAGATAATCTATAACTGG<br>CAGGGTGCCCAGTCTACCCAGGATGAGGTCGCTGCATCTGCCATCCTGACT<br>GCTCAGCTGGATGAGGAGCTGGGAGGTACCCCTGTCCAGAGCCGTGTGGTC<br>CAAGGCAAGGAGCCCGCCCACCTCATGAGCCTGTTTGGTGGGAAGCCCATG<br>ATCATCTACAAGGGCGGCACCTCCCGCGAGGGCGGGCAGACAGCCCCTGCC<br>AGCACCCGCCTCTTCCAGGTCCGCGCCAACAGCGCTGGAGCCACCCGGGCT<br>GTTGAGGTATTGCCTAAGGCTGGTGCACTGAACTCCAACGATGCCTTTGTT<br>CTGAAAACCCCCTCAGCCGCCTACCTGTGGGTGGGTACAGGAGCCAGCGAG<br>GCAGAGAAGACGGGGGCCCAGGAGCTGCTCAGGGTGCTGCGGGCCCAACCT | 15 |

TABLE 8-continued

Nucleotide sequences of normalizer proteins in panel.

| Gene Name | Nucleotide Sequence | Seq. ID. |
|---|---|---|
| | GTGCAGGTGGCAGAAGGCAGCGAGCCAGATGGCTTCTGGGAGGCCCTGGGC<br>GGGAAGGCTGCCTACCGCACATCCCCACGGCTGAAGGACAAGAAGATGGAT<br>GCCCATCCTCCTCGCCTCTTTGCCTGCTCCAACAAGATTGGACGTTTTGTG<br>ATCGAAGAGGTTCCTGGTGAGCTCATGCAGGAAGACCTGGCAACGGATGAC<br>GTCATGCTTCTGGACACCTGGGACCAGGTCTTTGTCTGGGTTGGAAAGGAT<br>TCTCAAGAAGAAGAAAAGACAGAAGCCTTGACTTCTGCTAAGCGGTACATC<br>GAGACGGACCCAGCCAATCGGGATCGGCGGACGCCCATCACCGTGGTGAAG<br>CAAGGCTTTGAGCCTCCCTCCTTTGTGGGCTGGTTCCTTGGCTGGGATGAT<br>GATTACTGGTCTGTGGACCCCTTGGACAGGGCCATGGCTGAGCTGGCTGCC<br>TGA | |
| LUM_HUMAN | ATGAGTCTAAGTGCATTTACTCTCTTCCTGGCATTGATTGGTGGTACCAGT<br>GGCCAGTACTATGATTATGATTTTCCCCTATCAATTTATGGGCAATCATCA<br>CCAAACTGTGCACCAGAATGTAACTGCCCTGAAAGCTACCCAAGTGCCATG<br>TACTGTGATGAGCTGAAATTGAAAAGTGTACCAATGGTGCCTCCTGGAATC<br>AAGTATCTTTACCTTAGGAATAACCAGATTGACCATATTGATGAAAAGGCC<br>TTTGAGAATGTAACTGATCTGCAGTGGCTCATTCTAGATCACAACCTTCTA<br>GAAAACTCCAAGATAAAAGGGAGTTTTCTCTAAATTGAAACAACTGAAG<br>AAGCTGCATATAAACCACAACAACCTGACAGAGTCTGTGGGCCCACTTCCC<br>AAATCTCTGGAGGATCTGCAGCTTACTCATAACAAGATCACAAAGCTGGGC<br>TCTTTTGAAGGATTGGTAAACCTGACCTTCATCCATCTCCAGCACAATCGG<br>CTGAAAGAGGATGCTGTTTCAGCTGCTTTTAAAGGTCTTAAATCACTCGAA<br>TACCTTGACTTGAGCTTCAATCAGATAGCCAGACTGCCTTCTGGTCTCCCT<br>GTCTCTCTTCTAACTCTCTACTTAGACAACAATAAGATCAGCAACATCCCT<br>GATGAGTATTTCAAGCGTTTTAATGCATTGCAGTATCTGCGTTTATCTCAC<br>AACGAACTGGCTGATAGTGGAATACCTGGAAATTCTTTCAATGTGTCATCC<br>CTGGTTGAGCTGGATCTGTCCTATAACAAGCTTAAAAACATACCAACTGTC<br>AATGAAAAACTTGAAAACTATTACCTGGAGGTCAATCAACTTGAGAAGTTT<br>GACATAAAGAGCTTCTGCAAGATCCTGGGGCCATTATCCTACTCCAAGATC<br>AAGCATTTGCGTTTGGATGGCAATCGCATCTCAGAAACCAGTCTTCCACCG<br>GATATGTATGAATGTCTACGTGTTGCTAACGAAGTCACTCTTAATTAA | 16 |
| C163A_HUMAN | ATGAGCAAACTCAGAATGGTGCTACTTGAAGACTCTGGATCTGCTGACTTC<br>AGAAGACATTTTGTCAACTTGAGTCCCTTCACCATTACTGTGGTCTTACTT<br>CTCAGTGCCTGTTTTGTCACCAGTTCTCTTGGAGGAACAGACAAGGAGCTG<br>AGGCTAGTGGATGGTGAAAACAAGTGTAGCGGGAGAGTGGAAGTGAAAGTC<br>CAGGAGGAGTGGGGAACGGTGTGTAATAATGGCTGGAGCATGGAAGCGGTC<br>TCTGTGATTTGTAACCAGCTGGGATGTCCAACTGCTATCAAAGCCCCTGGA<br>TGGGCTAATTCCAGTGCAGGTTCTGGACGCATTTGGATGGATCATGTTTCT<br>TGTCGTGGGAATGAGTCAGCTCTTTGGGATTGCAAACATGATGGATGGGA<br>AAGCATAGTAACTGTACTCACCAACAAGATGCTGGAGTGACCTGCTCAGAT<br>GGATCCAATTTGGAAATGAGGCTGACGCGTGAGGGAATATGTGTTCTGGA<br>AGAATAGAGATCAAATTCCAAGGACGGTGGGGAACAGTGTGATGATAAC<br>TTCAACATAGATCATGCATCTGTCATTTGTAGACAACTTGAATGTGGAAGT<br>GCTGTCAGTTTCTCTGGTTCATCTAATTTTGGAGAAAGGCTCTGGACCAATC<br>TGGTTTGATGATCTTATATGCAACGGAAATGAGTCAGCTCTCTGGAACTGC<br>AAACATCAAGGATGGGAAAGCATAACTGTGATCATGCTGAGGATGCTGGA<br>GTGATTTGCTCAAAGGGAGCAGATCTGAGCCTGAGACTGGTAGATGGAGTC<br>ACTGAATGTTCAGGAAGATTAGAAGTGAGATTCCAAGGAGAATGGGGGACA<br>ATATGTGATGACGGCTGGGACAGTTACGATGCTGCTGTGGCATGCAAGCAA<br>CTGGGATGTCCAACTGCCGTCACAGCCATTGGTCGAGTTAACGCCAGTAAG<br>GGATTTGGACACATCTGGCTTGACAGCGTTTCTTGCCAGGGACATGAACCT<br>GCTATCTGGCAATGTAAACACCATGAATGGGAAAGCATTATTGCAATCAC<br>AATGAAGATGCTGGCGTGACATGTTCTGATGGATCAGATCTGGAGCTAAGA<br>CTTAGAGGTGGAGGCAGCCGCTGTGCTGGGACAGTTGAGGTGGAGATTCAG<br>AGACTGTTAGGGAAGGTGTGTGACAGAGGCTGGGGACTGAAAGAAGCTGAT<br>GTGGTTTGCAGGCAGCTGGGATGTGGATCTGCACTCAAAACATCTTATCAA<br>GTGTACTCCAAAATCCAGGCAACAAACACATGGCTGTTTCTAAGTAGCTGT<br>AACGGAAATGAAACTTCTCTTTGGGACTGCAAGAACTGGCAATGGGGTGGA<br>CTTACCTGTGATCACTATGAAGAAGCCAAAATTACCTGCTCAGCCCACAGG<br>GAACCCAGACTGGTTGGAGGGGACATTCCCTGTTCTGGACGTGTTGAAGTG<br>AAGCATGGTGACACGTGGGGCTCCATCTGTGATTCGGACTTCTCTCTGGAA<br>GCTGCCAGCGTTCTATGCAGGGAATTACAGTGTGGCACAGTTGTCTCTATC<br>CTGGGGGAGCTCACTTTGGAGAGGGAAATGGACAGATCTGGGCTGAAGAA<br>TTCCAGTGTGAGGGACATGAGTCCCATCTTTCACTCTGCCCAGTAGCACCC<br>CGCCCAGAAGGAACTTGTAGCCACAGCAGGGATGTTGGAGTAGTCTGCTCA<br>AGATACACAGAAATTCGCTTGGTGAATGGCAAGACCCCGTGTGAGGGCAGA<br>GTGGAGCTCAAAACGCTTGGTGCCTGGGGATCCCTCTGTAACTCTCACTGG<br>GACATAGAAGATGCCCATGTTCTTTGCCAGCAGCTTAAATGTGGAGTTGCC<br>CTTTCTACCCCAGGAGGAGCACGTTTTGGAAAAGGAAATGGTCAGATCTGG<br>AGGCATATGTTTCACTGCACTGGGACTGAGCAGCACATGGGAGATTGTCCT<br>GTAACTGCTCTAGGTGCTTCATTATGTCCTTCAGAGCAAGTGGCCTCTGTA<br>ATCTGCTCAGGAAACCAGTCCCAAACACTGTCCTCGTGCAATTCATCGTCT<br>TTGGGCCCAACAAGGCCTACCATTCCAGAAGAAAGTGCTGTGGCCTGCATA<br>GAGAGTGGTCAACTTCGCCTGGTAAATGGAGGAGGTCGCTGTGCTGGGAGA | 17 |

TABLE 8-continued

Nucleotide sequences of normalizer proteins in panel.

| Gene Name | Nucleotide Sequence | Seq. ID. |
|---|---|---|
|  | GTAGAGATCTATCATGAGGGCTCCTGGGGCACCATCTGTGATGACAGCTGG<br>GACCTGAGTGATGCCCACGTGGTTTGCAGACAGCTGGGCTGTGGAGAGGCC<br>ATTAATGCCACTGGTTCTGCTCATTTTGGGGAAGGAACAGGGCCCATCTGG<br>CTGGATGAGATGAAATGCAATGGAAAAGAATCCCGCATTTGGCAGTGCCAT<br>TCACACGGCTGGGGGCAGCAAAATTGCAGGCACAAGGAGGATGCGGGAGTT<br>ATCTGCTCAGAATTCATGTCTCTGAGACTGACCAGTGAAGCCAGCAGAGAG<br>GCCTGTGCAGGGCGTCTGGAAGTTTTTTACAATGGAGCTTGGGGCACTGTT<br>GGCAAGAGTAGCATGTCTGAAACCACTGTGGGTGTGGTGTGCAGGCAGCTG<br>GGCTGTGCAGACAAAGGGAAAATCAACCCTGCATCTTTAGACAAGGCCATG<br>TCCATTCCCATGTGGGTGGACAATGTTCAGTGTCCAAAAGGACCTGACACG<br>CTGTGGCAGTGCCCATCATCTCCATGGGAGAAGAGACTGGCCAGCCCCTCG<br>GAGGAGACCTGGATCACATGTGACAACAAGATAAGACTTCAGGAAGGACCC<br>ACTTCCTGTTCTGGACGTGTGGAGATCTGGCATGGAGGTTCCTGGGGGACA<br>GTGTGTGATGACTCTTGGGACTTGGACGATGCTCAGGTGGTGTGTCAACAA<br>CTTGGCTGTGGTCCAGCTTTGAAAGCATTCAAAGAAGCAGAGTTTGGTCAG<br>GGGACTGGACCGATATGGCTCAATGAAGTGAAGTGCAAAGGGAATGAGTCT<br>TCCTTGTGGGATTGTCCTGCCAGACGCTGGGGCCATAGTGAGTGTGGGCAC<br>AAGGAAGACGCTGCAGTGAATTGCACAGATATTTCAGTGCAGAAAACCCCA<br>CAAAAAGCCACAACAGGTCGCTCATCCCGTCAGTCATCCTTTATTGCAGTC<br>GGGATCCTTGGGGTTGTTCTGTTGGCCATTTTCGTCGCATTATTCTTCTTG<br>ACTAAAAAGCGAAGACAGAGACAGCGGCTTGCAGTTTCCTCAAGAGGAGAG<br>AACTTAGTCCACCAAATTCAATACCGGGAGATGAATTCTTGCCTGAATGCA<br>GATGATCTGGACCTAATGAATTCCTCAGGAGGCCATTCTGAGCCACACTGA |  |
| PTPRJ_HUMAN | ATGAAGCCGGCGGCGCGGGAGGCGCGGCTGCCTCCGCGCTCGCCCGGGCTG<br>CGCTGGGCGCTGCCGCTGCTGCTGCTGCTGCGCCTGGGCCAGATCCTG<br>TGCGCAGGTGGCACCCCTAGTCCAATTCCTGACCCTTCAGTAGCAACTGT<br>GCCACAGGGGAAAATGGCATAACGCAGATCAGCAGTACAGCAGAATCCTTT<br>CATAAACAGAATGGAACTGGAACACCTCAGGTGGAAACAAACACCAGTGAG<br>GATGGTGAAAGCTCTGGAGCCAACGATAGTTTAAGAACACCTGAACAAGGA<br>TCTAATGGGACTGATGGGGCATCTCAAAAAACTCCCAGTAGCACTGGGCCC<br>AGTCCTGTGTTTGACATTAAAGCTGTTTCCATCAGTCCAACCAATGTGATC<br>TTAACTTGGAAAAGTAATGACACAGCTGCTTCTGAGTACAAGTATGTAGTA<br>AAGCATAAGATGGAAAATGAGAAGACAATTACTGTTGTGCATCAACCATGG<br>TGTAACATCACAGGCTTACGTCCAGCGACTTCATATGTATTCTCCATCACT<br>CCAGGAATAGGCAATGAGACTTGGGGAGATCCCAGAGTCATAAAAGTCATC<br>ACAGAGCCGATCCCAGTTTCTGATCTCCGTGTTGCCCTCACGGGTGTGAGG<br>AAGGCTGCTCTCCTGGAGCAATGGCAATGGCACTGCCTCCTGCCGGGTT<br>CTTCTTGAAAGCATTGGAAGCCATGAGGAGTTGACTCAAGACTCAAGACTT<br>CAGGTCAATATCTCGGGCCTGAAGCCAGGGGTTCAATACAACATCAACCCG<br>TATCTTCTACAATCAAATAAGACAAAGGGAGACCCCTTGGGCACAGAAGGT<br>GGCTTGGATGCCAGCAATACAGAGAGAAGCCGGGCAGGGAGCCCCACCGCC<br>CCTGTGCATGATGAGTCCCTCGTGGGACCTGTGGACCCATCCTCCGGCCAG<br>CAGTCCCGAGACACGGAAGTCCTGCTTGTCGGGTTAGAGCCTGGCACCCGA<br>TACAATGCCACCGTTTATTCCCAAGCAGCGAATGGCACAGAAGGACAGCCC<br>CAGGCCATAGAGTTCAGGACAAATGCTATTCAGGTTTTTGACGTCACCGCT<br>GTGAACATCAGTGCCACAAGCCTGACCCTGATCTGGAAAGTCAGCGATAAC<br>GAGTCGTCATCTAACTATACCTACAAGATACATGTGGCGGGGGAGACAGAT<br>TCTTCCAATCTCAACGTCAGTGAGCCTCGCGCTGTCATCCCCGGACTCCGC<br>TCCAGCACCTTCTACAACATCACAGTGTGTCCTGTCCTAGGTGACATCGAG<br>GGCACGCCGGGCTTCCTCCAAGTGCACACCCCCCTGTTCCAGTTTCTGAC<br>TTCCGAGTGACAGTGGTCAGCACGACGGAGATCGGCTTAGCATGGAGCAGC<br>CATGATGCAGAATCATTTCAGATGCATATCACACAGGAGGGAGCTGGCAAT<br>TCTCGGGTAGAAATAACCACCAACCAAAGTATTATCATTGGTGGCTTGTTC<br>CCTGGAACCAAGTATTGCTTTGAAATAGTTCAAAAGGACCAAATGGGACT<br>GAAGGGGCATCTCGGACAGTTTGCAATAGAACTGGATGA | 18 |

TABLE 9

Amino acid sequences of normalizer proteins in panel

| Gene Name | Nucleotide Sequence | Seq. ID. |
|---|---|---|
| PEDF_HUMAN | MQALVLLLCIGALLGHSSCQNPASPPEEGSPDPDSTGALVEEEDPFFKVPV<br>NKLAAAVSNFGYDLYRVRSSTSPTTNVLLSPLSVATALSALSLGAEQRTES<br>IIHRALYYDLISSPDIHGTYKELLDTVTAPQKNLKSASRIVFEKKLRIKSS<br>FVAPLEKSYGTRPRVLTGNPRLDLQEINNWVQAMKGKLARSTKEIPDEIS<br>ILLLGVAHFKGQWVTKFDSRKTSLEDFYLDEERTVRVPMMSDPKAVLRYGL<br>DSDLSCKIAQLPLTGSMSIIFFLPLKVTQNLTLIEESLTSEFIHDIDRELK | 19 |

TABLE 9-continued

Amino acid sequences of normalizer proteins in panel

| Gene Name | Nucleotide Sequence | Seq. ID. |
|---|---|---|
| | TVQAVLTVPKLKLSYEGEVTKSLQEMKLQSLFDSPDFSKITGKPIKLTQVE HRAGFEWNEDGAGTTPSPGLQPAHLTFPLDYHLNQPFIFVLRDTDTGALLF IGKILDPRGP | |
| MASP1_HUMAN | MRWLLLYYALCFSLSKASAHTVELNNMFGQIQSPGYPDSYPSDSEVTWNIT VPDGFRIKLYFMHFNLESSYLCEYDYVKVETEDQVLATFCGRETTDTEQTP GQEVVLSPGSFMSITFRSDFSNEERFTGFDAHYMAVDVDECKEREDEELSC DHYCHNYIGGYYCSCRFGYILHTDNRTCRVECSDNLFTQRTGVITSPDFPN PYPESSECLYTIELEEGFMVNLQFEDIFDIEDHPEVPCPYDYIKIKVGPKV LGPFCGEKAPEPISTQSNSVLILFHSDNSGENRGWRLSYRAAGNECPELQP PVHGKIEPSQAKYFFKDQVLVSCDTGYKVLKDNVEMDTFQIECLKDGTWSN KIPTCKIVDCRAPGELEHGLITFSTRNNLTTYKSEIKYSCQEPYYKMLNNN TGIYTCSAQGVWMNKVLGRSLPTCLPVCGLPKFSRKLMARIFNGRPAQKGT TPWIAMLSHLNGQPFCGGSLLGSSWIVTAAHCLHQSLDPEDPTLRDSDLLS PSDFKIILGKHWRLRSDENEQHLGVKHTTLHPQYDPNTFENDVALVELLES PVLNAFVMPICLPEGPQQEGAMVIVSGWGKQFLQRFPETLMEIETPIVDHS TCQKAYAPLKKKVTRDMICAGEKEGGKDACAGDSGGPMVTLNRERGQWYLV GTVSWGDDCGKKDRYGVYSYIHHNKDWIQRVTGVRN | 20 |
| GELS_HUMAN | MAPHRPAPALLCALSLALCALSLPVRAATASRGASQAGAPQGRVPEARPNS MVVEHPEFLKAGKEPGLQIWRVEKFDLVPVPTNLYGDFFTGDAYVILKTVQ LRNGNLQYDLHYWLGNECSQDESGAAAIFTVQLDDYLNGRAVQHREVQGFE SATFLGYFKSGLKYKKGGVASGFKHVVPNEVVVQRLFQVKGRRVVRATEVP VSWESFNNGDCFILDLGNNIHQWCGSNSNRYERLKATQVSKGIRDNERSGR ARVHVSEEGTEPEAMLQVLGPKPALPAGTEDTAKEDAANRKLAKLTASDFI TKMDYPKQTQVSVLPEGGETPLFKQFFKNWRDPDQTDGLGLSYLSSHIANV ERVPFDAATLHTSTAMAAQHGMDDDGTGQKQIWRIEGSNKVPVDPATYGQF YGGDSYTILYNYRHGGRQGQIIYNWQGAQSTQDEVAASAILTAQLDEELGG TPVQSRVVQGKEPAHLMSLFGGKPMIIYKGGTSREGGQTAPASTRLFQVRA NSAGATRAVEVLPKAGALNSNDAFVLKTPSAAYLWVGTGASEAEKTGAQEL LRVLRAQPVQVAEGSEPDGFWEALGGKAAYRTSPRLKDKKMDAHPPRLFAC SNKIGRFVIEEVPGELMQEDLATDDVMLLDTWDQVFVWVGKDSQEEEKTEA LTSAKRYIETDPANRDRRTPITVVKQGFEPPSFVGWFLGWDDDYWSVDPLD RAMAELAA | 21 |
| LUM_HUMAN | MSLSAFTLFLALIGGTSGQYYDYDFPLSIYGQSSPNCAPECNCPESYPSAM YCDELKLKSVPMVPPGIKYLYLRNNQIDHIDEKAFENVTDLQWLILDHNLL ENSKIKGRVFSKLKQLKKLHINHNNLTESVGPLPKSLEDLQLTHNKITKLG SFEGLVNLTFIHLQHNRLKEDAVSAAFKGLKSLEYLDLSFNQIARLPSGLP VSLLTLYLDNNKISNIPDEYFKRFNALQYLRLSHNELADSGIPGNSFNVSS LVELDLSYNKLKNIPTVNENLENYYLEVNQLEKFDIKSFCKILGPLSYSKI KHLRLDGNRISETSLPPDMYECLRVANEVTLN | 22 |
| C163A_HUMAN | MSKLRMVLLEDSGSADFRRHFVNLSPFTITVVLLLSACFVTSSLGGTDKEL RLVDGENKCSGRVEVKVQEEWGTVCNNGWSMEAVSVICNQLGCPTAIKAPG WANSSAGSGRIWMDHVSCRGNESALWDCKHDGWGKHSNCTHQQDAGVTCSD GSNLEMRLTRGGNMCSGRIEIKFQGRWGTVCDDNFNIDHASVICRQLECGS AVSFSGSSNFGEGSGPIWFDDLICNGNESALWNCKHQGWGKHNCDHAEDAG VICSKGADLSLRLVDGVTECSGRLEVRFQGEWGTICDDGWDSYDAAVACKQ LGCPTAVTAIGRVNASKGFGHIWLDSVSCQGHEPAIWQCKHHEWGKHYCNH NEDAGVTCSDGSDLELRLRGGGSRCAGTVEVEIQRLLGKVCDRGWGLKEAD VVCRQLGCGSALKTSYQVYSKIQATNTWLFLSSCNGNETSLWDCKNWQWGG LTCDHYEEAKITCSAHREPRLVGGDIPCSGRVEVKHGDTWGSICDSDFSLE AASVLCRELQCGTVVSILGGAHFGEGNGQIWAEEFQCEGHESHLSLCPVAP RPEGTCSHSRDVGVVCSRYTEIRLVNGKTPCEGRVELKTLGAWGSLCNSHW DIEDAHVLCQQLKCGVALSTPGGARFGKGNGQIWRHMFHCTGTEQHMGDCP VTALGASLCPSEQVASVICSGNQSQTLSSCNSSSLGPTRPTIPEESAVACI ESGQLRLVNGGGRCAGRVEIYHEGSWGTICDDSWDLSDAHVVCRQLGCGEA INATGSAHFGEGTGPIWLDEMKCNGKESRIWQCHSHGWGQQNCRHKEDAGV ICSEFMSLRLTSEASREACAGRLEVFYNGAWGTVGKSSMSETTVGVVCRQL GCADKGKINPASLDKAMSIPMWVDNVQCPKGPDTLWQCPSSPWEKRLASPS EETWITCDNKIRLQEGPTSCSGRVEIWHGGSWGTVCDDSWDLDDAQVVCQQ LGCGPALKAFKEAEFGQGTGPIWLNEVKCKGNESSLWDCPARRWGHSECGH KEDAAVNCTDISVQKTPQKATTGRSSRQSSFIAVGILGVVLLAIFVALFFL TKKRRQRQLRAVSSRGENLVHQIQYREMNSCLNADDLDLMNSSENSHESAD FSAAELISVSKFLPISGMEKEAILSHTEKENGNL | 23 |
| PTPRJ_HUMAN | MKPAAREARLPPRSPGLRWALPLLLLLLRLGQILCAGGTPSPIPDPSVATV ATGENGITQISSTAESFHKQNGTGTPQVETNTSEDGESSGANDSLRTPEQG SNGTDGASQKTPSSTGPSPVFDIKAVSISPTNVLITWKSNDTAASEYKYVV KHKMENEKTITVVHQPWCNITGLRPATSYVFSITPGIGNETWGDPRVIKVI TEPIPVSDLRVALTGVRKAALSWSNGNGTASCRVLLESIGSHEELTQDSRL QVNISGLKPGVQYNINPYLLQSNKTKGDPLGTEGGLDASNTERSRAGSPTA PVHDESLVGPVDPSSGQQSRDTEVLLVGLEPGTRYNATVYSQAANGTEGQP QAIEFRTNAIQVFDTAVNISATSLTLIWKVSDNESSSNYTYKIHVAGETD | 24 |

TABLE 9-continued

Amino acid sequences of normalizer proteins in panel

| Gene Name | Nucleotide Sequence | Seq. ID. |
|---|---|---|
| | SSNLNVSEPRAVIPGLRSSTFYNITVCPVLGDIEGTPGFLQVHTPPVPVSD FRVTVVSTTEIGLAWSSHDAESFQMHITQEGAGNSRVEITTNQSIIIGGLF PGTKYCFEIVPKGPNGTEGASRTGCNRTVPSAVFHIHVVYVTTTEMWLDWK SPDGASEYVYHLVIESKHGSNHTSTYDKAITLQGLIPGTLYNITISPEVDH VWGDPNSTAQYTRPSNVSNIDVSTNTTAATLSWQNFDDASPTYSYCLLIEK AGNSSNATQVVTDIGITDATVTELIPGSSYTVEIFAQVGDGIKSLEPGRKS FCTDPASMASFDCEVVPKEPALVLKWTCPPGANAGFELEVSSGAWNNATHL ESCSSENGTEYRTEVTYLNFSTSYNISITTVSCGKMAAPTRNTCTTGITDP PPPDGSPNITSVSHNSVKVKFSGFEASHGPIKAYAVILTTGEAGHPSADVL KYTYEDFKKGASDTYVTYLIRTEEKGRSQSLSEVLKYEIDVGNESTTLGYY NGKLEPLGSYRACVAGFTNITFHPQNKGLIDGAESYVSFSRYSDAVSLPQD PGVICGAVFGCIFGALVIVTVGGFIFWRKKRKDAKNNEVSFSQIKPKKSKL IRVENFEAYFKKQQADSNCGFAEEYEDLKLVGISQPKYAAELAENRGKNRY NNVLPYDISRVKLSVQTHSTDDYINANYMPGYHSKKDFIATQGPLPNTLKD FWRMVWEKNVYAIIMLTKCVEQGRTKCEEYWPSKQAQDYGDITVAMTSEIV LPEWTIRDFTVKNIQTSESHPLRQFHFTSWPDHGVPDTTDLLINFRYLVRD YMKQSPPESPILVHCSAGVGRTGTFIAIDRLIYQIENENTVDVYGIVYDLR MHRPLMVQTEDQYVFLNQCVLDIVRSQKDSKVDLIYQNTTAMTIYENLAPV TTFGKTNGYIA | |

What is claimed is:

1. A method of scoring a pulmonary nodule in a subject comprising:
   (a) assaying the expression of a plurality of proteins comprising determining the protein expression level of at least each of ALDOA_HUMAN, FRIL_HUMAN, LG3BP_HUMAN, TSP1_HUMAN and COIA1_HUMAN from a biological sample obtained from the subject by selected reaction monitoring mass spectrometry of proteolytically digested fragments of the plurality of proteins contacted to labeled synthetic peptide fragments, wherein the determining step comprises detecting peptide transitions comprising at least ALQASALK (SEQ ID NO:25) (401.25, 617.4), AVGLAGTFR (SEQ ID NO:26) (446.26, 721.4), GFLLLASLR (SEQ ID NO:27) (495.31, 559.4), LGGPEAGLGEYLFER (SEQ ID NO:28) (804.4, 1083.6), and VEIFYR (SEQ ID NO:29) (413.73, 598.3);
   (b) calculating a score from the protein expression of at least each of ALDOA_HUMAN, FRIL_HUMAN, LG3BP_HUMAN, TSP1 HUMAN and COIA1_HUMAN from the biological sample determined in step (a);
   wherein said score is determined as $P_s=1/[1+\exp(-\alpha-\Sigma_{i=1}^{5}\beta_i*\breve{I}_{i,s}-\gamma*\breve{I}_{COIA1}*\breve{I}_{FRIL})]$, where $\breve{I}_{i,s}$ is Box-Cox transformed and normalized intensity of transition i in said sample (s), $\beta_i$ is the corresponding logistic regression coefficient, $\alpha$ is a panel-specific constant, and $\gamma$ is a coefficient for the interaction term.

2. The method of claim 1, wherein the subject has a lung condition.

3. The method of claim 1, wherein the pulmonary nodule is 30 mm or less.

4. The method of claim 3, wherein the pulmonary nodule is between 8-30 mm.

5. The method of claim 2, wherein said lung condition is cancer or a non-cancerous lung condition.

6. The method of claim 2, wherein said lung condition is non-small cell lung cancer.

7. The method of claim 5, wherein said non-cancerous lung condition is chronic obstructive pulmonary disease, hamartoma, fibroma, neurofibroma, granuloma, sarcoidosis, bacterial infection or fungal infection.

8. The method of claim 1, wherein the subject is a human.

9. The method of claim 1, wherein said biological sample is tissue, blood, plasma, serum, whole blood, urine, saliva, genital secretions, cerebrospinal fluid, sweat, excreta, or bronchoalveolar lavage.

10. The method of claim 1, wherein assaying the expression of a plurality of proteins further comprises determining the protein expression level of at least one of PEDF_HUMAN, MASP1_HUMAN, GELS_HUMAN, LUM_HUMAN, C163A_HUMAN and PTPRJ_HUMAN.

11. The method of claim 1, wherein determining the protein expression level of at least each of ALDOA_HUMAN, FRIL_HUMAN, LG3BP_HUMAN, TSP1_HUMAN and COIA1_HUMAN comprises fragmenting each protein to generate at least one peptide.

12. The method of claim 11, wherein the proteins are fragmented by trypsin digestion.

13. The method of claim 12, further comprising providing a synthetic, modified, heavy peptides corresponding to each peptide generated from each of ALDOA_HUMAN, FRIL_HUMAN, LG3BP_HUMAN, TSP1_HUMAN and COIA1_HUMAN.

14. The method of claim 13, wherein at least one of the synthetic peptides has an isotopic label attached.

15. The method of claim 1, wherein the expression of a plurality of proteins is performed by liquid chromatography-selected reaction monitoring/mass spectrometry (LC-SRM-MS).

16. The method of claim 11, wherein a transition for each peptide is determined by liquid chromatography-selected reaction monitoring/mass spectrometry (LC-SRM-MS).

17. A method of determining that a pulmonary nodule in a subject is not lung cancer, comprising:
   (a) contacting a biological sample obtained from the subject with a proteolytic enzyme to produce peptide fragments from a panel of proteins present in the biological sample, wherein the panel comprises ALDOA_HUMAN, FRIL_HUMAN, LG3BP_HUMAN, TSP1_HUMAN and COIA1_HUMAN;
   (b) combining the produced peptide fragments from the panel from step (a) with labeled, synthetic peptide fragments which correspond to the produced peptide fragments from the panel;
   (c) performing selected reaction monitoring mass spectrometry to measure the abundance of the peptide fragments from step (b), wherein the measuring step comprises detecting the peptide transitions comprising at least ALQASALK (SEQ ID NO:25) (401.25, 617.4), AVGLAGTFR (SEQ ID NO:26) (446.26, 721.4), GFLLLASLR (SEQ ID NO:27) (495.31, 559.4), LGGPEAGLGEYLFER (SEQ ID NO:28) (804.4, 1083.6), and VEIFYR (SEQ ID NO:29) (413.73, 598.3);

(d) calculating a score based on the peptide fragment measurements of step (c) and one protein-protein interaction comprising peptide fragments produced from FRIL_HUMAN and COIA1_HUMAN, wherein said score is determined as $P_s=1/[1+\exp(-\alpha-\Sigma_{i=1}^{5}\beta_i *\breve{I}_{i,s} - \gamma *\breve{I}_{COIA1}*\breve{I}_{FRIL})]$, where $\breve{I}_{i,s}$ is Box-Cox transformed and normalized intensity of transition i in said sample (s), $\beta_i$ is the corresponding logistic regression coefficient, $\alpha$ is a panel-specific constant, and $\gamma$ is a coefficient for the interaction term; and (e) ruling out lung cancer for the human subject if the score in step (d) is closer to 0.0 than to 1.0.

18. The method of claim 17, further comprising:

(f) Performing image monitoring on the subject for at least a one-year period if the pulmonary nodule is determined not to be lung cancer.

* * * * *

SEQUENCE LISTING

<160> NUMBER OF SEQ ID NOS: 29

<210> SEQ ID NO 1
<211> LENGTH: 1095
<212> TYPE: DNA
<213> ORGANISM: Homo sapiens

<400> SEQUENCE: 1

```
atgccctacc aatatccagc actgaccccg gagcagaaga aggagctgtc tgacatcgct      60
caccgcatcg tggcacctgg caagggcatc ctggctgcag atgagtccac tgggagcatt     120
gccaagcggc tgcagtccat tggcaccgag aacaccgagg agaaccggcg cttctaccgc     180
cagctgctgc tgacagctga cgaccgcgtg aaccccctgca ttgggggtgt catcctcttc     240
catgagacac tctaccagaa ggcggatgat gggcgtccct tcccccaagt tatcaaatcc     300
aagggcggtg ttgtgggcat caaggtagac aagggcgtgg tcccccctggc agggacaaat     360 ggcgagacta ccacccaagg gttggatggg ctgtctgagc gctgtgccca gtacaagaag     420 gacgagctg  acttcgccaa gtggcgttgt gtgctgaaga ttggggaaca cacccccctca     480 gccctcgcca tcatggaaaa tgccaatgtt ctggcccgtt atgccagtat ctgccagcag     540
aatggcattg tgcccatcgt ggagcctgag atcctccctg atgggaccat gacttgaag      600 cgctgccagt atgtgaccga aaggtgctg gctgctgtct acaaggctct gagtgaccac      660
cacatctacc tggaaggcac cttgctgaag cccaacatgg tcaccccagg ccatgcttgc     720
actcagaagt tttctcatga ggagattgcc atggcgaccg tcacagcgct cgccgcaca      780 gtgcccccg  ctgtcactgg gatcaccttc ctgtctggag ccagagtga ggaggaggcg      840 tccatcaacc tcaatgccat taacaagtgc ccctgctga agccctgggc cctgaccttc      900
tcctacggcc gagccctgca ggcctctgcc ctgaaggcct ggggcgggaa aaggagaac     960 ctgaaggctg cgcaggagga gtatgtcaag cgagccctgg ccaacagcct tgcctgtcaa    1020
ggaaagtaca ctccgagcgg tcaggctggg gctgctgcca gcgagtccct cttcgtctct    1080
aaccacgcct attaa                                                     1095
```

<210> SEQ ID NO 2
<211> LENGTH: 1257
<212> TYPE: DNA
<213> ORGANISM: Homo sapiens

<400> SEQUENCE: 2

```
atggcaaggc gcaagccaga agggtccagc ttcaacatga cccacctgtc catggctatg      60
gccttttcct ttcccccagt tgccagtggg caactccacc ctcagctggg caacacccag     120
caccagacag agttaggaaa ggaacttgct actaccagca ccatgcccta ccaatatcca     180
gcactgaccc cggagcagaa gaaggagctg tctgacatcg ctcaccgcat cgtggcacct     240
ggcaagggca tcctggctgc agatgagtcc actgggagca ttgccaagcg gctgcagtcc     300
attggcaccg agaacaccga ggagaaccgg cgcttctacc gccagctgct gctgacagct     360
gacgaccgcg tgaaccctg cattgggggt gtcatcctct ccatgagac actctaccag      420 aaggcggatg atgggcgtcc cttcccccaa gttatcaaat ccaagggcgg tgttgtgggc     480
atcaaggtag acaagggcgt ggtccccctg gcagggacaa atggcgagac taccacccaa     540
gggttggatg ggctgtctga gcgctgtgcc cagtacaaga ggacggagc tgacttcgcc      600 aagtggcgtt gtgtgctgaa gattggggaa cacacccct cagccctcgc catcatggaa      660
aatgccaatg ttctggcccg ttatgccagt atctgccagc agaatggcat tgtgcccatc     720
gtggagcctg agatcctccc tgatggggac atgacttga gcgctgcca gtatgtgacc       780 gagaaggtgc tggctgctgt ctacaaggct ctgagtgacc accacatcta cctggaaggc     840
accttgctga gcccaacat ggtcacccca ggccatgctt gcactcagaa gtttttctcat     900 gaggagattg ccatggcgac cgtcacagcg ctgcgccgca cagtgccccc cgctgtcact     960
gggatcacct tcctgtctgg aggccagagt gaggaggagg cgtccatcaa cctcaatgcc    1020
attaacaagt gcccctgct gaagccctgg gccctgacct tctcctacgg ccgagccctg     1080
caggcctctg ccctgaaggc ctggggcggg aagaaggaga acctgaaggc tgcgcaggag    1140
gagtatgtca gcgagccct ggccaacagc cttgcctgtc aaggaaagta cactccgagc     1200
ggtcaggctg ggctgctgc cagcgagtcc ctcttcgtct ctaaccacgc ctattaa       1257
```

<210> SEQ ID NO 3
<211> LENGTH: 528
<212> TYPE: DNA
<213> ORGANISM: Homo sapiens

<400> SEQUENCE: 3

```
atgagctccc agattcgtca gaattattcc accgacgtgg aggcagccgt caacagcctg      60
gtcaatttgt acctgcaggc ctcctacacc tacctctctc tgggcttcta tttcgaccgc     120
gatgatgtgg ctctggaagg cgtgagccac ttcttccgcg aattggccga ggagaagcgc     180
gagggctacg agcgtctcct gaagatgcaa aaccagcgtg gcggccgcgc tctcttccag     240
gacatcaaga gccagctga agatgagtgg ggtaaaaccc cagacgccat gaaagctgcc      300 atggcctgg agaaaagct gaaccaggcc cttttggatc ttcatgccct gggttctgcc      360
cgcacggacc ccatctctg tgacttcctg gagactcact tcctagatga ggaagtgaag     420
cttatcaaga gatgggtga ccacctgacc aacctccaca ggctgggtgg cccggaggct     480
gggctgggcg agtatctctt cgaaaggctc actctcaagc acgactaa                528
```

<210> SEQ ID NO 4
<211> LENGTH: 1758
<212> TYPE: DNA

<213> ORGANISM: Homo sapiens

<400> SEQUENCE: 4

| | |
|---|---|
| atgacccctc cgaggctctt ctgggtgtgg ctgctggttg caggaaccca aggcgtgaac | 60 |
| gatggtgaca tgcggctggc cgatgggggc gccaccaacc agggccgcgt ggagatcttc | 120 |
| tacagaggcc agtggggcac tgtgtgtgac aacctgtggg acctgactga tgccagcgtc | 180 |
| gtctgccggg ccctgggctt cgagaacgcc acccaggctc tgggcagagc tgccttcggg | 240 |
| caaggatcag gccccatcat gctggatgag gtccagtgca cgggaaccga ggcctcactg | 300 |
| gccgactgca gtccctgggg ctggctgaag agcaactgca ggcacgagag agacgctggt | 360 |
| gtggtctgca ccaatgaaac caggagcacc cacaccctgg acctctccag ggagctctcg | 420 |
| gaggcccttg ccagatcttt tgacagccag cggggctgcg acctgtccat cagcgtgaat | 480 |
| gtgcagggcg aggacgccct gggcttctgt ggccacacgg tcatcctgac tgccaacctg | 540 |
| gaggcccagg ccctgtggaa ggagccgggc agcaatgtca ccatgagtgt ggatgctgag | 600 |
| tgtgtgccca tggtcaggga ccttctcagg tacttctact cccgaaggat tgacatcacc | 660 |
| ctgtcgtcag tcaagtgctt ccacaagctg gcctctgcct atgggggccag gcagctgcag | 720 |
| ggctactgcg caagcctctt tgccatcctc ctcccccagg acccctcgtt ccagatgccc | 780 |
| ctggacctgt atgcctatgc agtggccaca ggggacgccc tgctggagaa gctctgccta | 840 |
| cagttcctgg cctggaactt cgaggccttg acgcaggccg aggcctggcc cagtgtcccc | 900 |
| acagacctgc tccaactgct gctgcccagg agcgacctgg cggtgcccag cgagctggcc | 960 |
| ctactgaagg ccgtggacac ctggagctgg ggggagcgtg cctcccatga ggaggtggag | 1020 |
| ggcttggtgg agaagatccg cttccccatg atgctccctg aggagctctt tgagctgcag | 1080 |
| ttcaacctgt ccctgtactg gagccacgag gccctgttcc agaagaagac tctgcaggcc | 1140 |
| ctggaattcc acactgtgcc cttccagttg ctggcccggt acaaaggcct gaacctcacc | 1200 |
| gaggatacct acaagccccg gatttacacc tcgcccacct ggagtgcctt tgtgacagac | 1260 |
| agttcctgga gtgcacggaa gtcacaactg gtctatcagt ccagacgggg gcctttggtc | 1320 |
| aaatattctt ctgattactt ccaagccccc tctgactaca gatactaccc ctaccagtcc | 1380 |
| ttccagactc cacaacaccc cagcttcctc ttccaggaca gagggtgtc ctggtccctg | 1440 |
| gtctacctcc ccaccatcca gagctgctgg aactacggct tctcctgctc ctcggacgag | 1500 |
| ctccctgtcc tgggcctcac caagtctggc ggctcagatc gcaccattgc ctacgaaaac | 1560 |
| aaagccctga tgctctgcga agggctcttc gtggcagacg tcaccgatttt cgagggctgg | 1620 |
| aaggctgcga ttcccagtgc cctggacacc aacagctcga gagcacctc ctccttcccc | 1680 |
| tgcccggcag ggcacttcaa cggcttccgc acggtcatcc gccccttcta cctgaccaac | 1740 |
| tcctcaggtg tggactag | 1758 |

<210> SEQ ID NO 5
<211> LENGTH: 3513
<212> TYPE: DNA
<213> ORGANISM: Homo sapiens

<400> SEQUENCE: 5

| | |
|---|---|
| atggggctgg cctggggact aggcgtcctg ttcctgatgc atgtgtgtgg caccaaccgc | 60 |
| attccagagt ctggcggaga caacagcgtg tttgacatct ttgaactcac cggggccgcc | 120 |
| cgcaagggt ctgggcgccg actggtgaag ggccccgacc cttccagccc agcttttccgc | 180 |
| atcgaggatg ccaacctgat ccccctgtg cctgatgaca agttccaaga cctggtggat | 240 |

-continued

```
gctgtgcggg cagaaaaggg tttcctcctt ctggcatccc tgaggcagat gaagaagacc      300
cggggcacgc tgctggccct ggagcggaaa gaccactctg gccaggtctt cagcgtggtg      360
tccaatggca aggcgggcac cctggacctc agcctgaccg tccaaggaaa gcagcacgtg      420
gtgtctgtgg aagaagctct cctggcaacc ggccagtgga gagcatcac cctgtttgtg       480
caggaagaca gggcccagct gtacatcgac tgtgaaaaga tggagaatgc tgagttggac      540
gtccccatcc aaagcgtctt caccagagac ctggccagca tcgccagact ccgcatcgca      600
aaggggggcg tcaatgacaa tttccagggg gtgctgcaga atgtgaggtt tgtctttgga      660
accacaccag aagacatcct caggaacaaa ggctgctcca gctctaccag tgtcctcctc      720
acccttgaca caacgtggt gaatggttcc agccctgcca tccgcactaa ctacattggc       780
cacaagacaa aggacttgca agccatctgc ggcatctcct gtgatgagct gtccagcatg      840
gtcctggaac tcaggggcct gcgcaccatt gtgaccacgc tgcaggacag catccgcaaa      900
gtgactgaag agaacaaaga gttggccaat gagctgaggc ggcctcccct atgctatcac      960
aacggagttc agtacagaaa taacgaggaa tggactgttg atagctgcac tgagtgtcac     1020
tgtcagaact cagttaccat ctgcaaaaag gtgtcctgcc ccatcatgcc ctgctccaat     1080
gccacagttc ctgatggaga atgctgtcct cgctgttggc ccagcgactc tgcggacgat     1140
ggctggtctc catggtccga gtggaccctcc tgttctacga gctgtggcaa tggaattcag    1200
cagcgcggcc gctcctgcga tagcctcaac aaccgatgtg agggctcctc ggtccagaca     1260
cggacctgcc acattcagga gtgtgacaag agatttaaac aggatggtgg ctggagccac     1320
tggtccccgt ggtcatcttg ttctgtgaca tgtggtgatg gtgtgatcac aaggatccgg     1380
ctctgcaact ctcccagccc ccagatgaac gggaaaccct gtgaaggcga agcgcgggag     1440
accaaagcct gcaagaaaga cgcctgcccc atcaatgag gctggggtcc ttggtcacca      1500
tgggacatct gttctgtcac ctgtggagga ggggtacaga aacgtagtcg tctctgcaac     1560
aaccccacac cccagtttgg aggcaaggac tgcgttggtg atgtaacaga aaaccagatc     1620
tgcaacaagc aggactgtcc aattgatgga tgcctgtcca atccctgctt tgccggcgtg     1680
aagtgtacta gctaccctga tggcagctgg aaatgtggtg cttgtcccc tggttacagt      1740
ggaaatggca tccagtgcac agatgttgat gagtgcaaag aagtgcctga tgcctgcttc     1800
aaccacaatg gagagcaccg gtgtgagaac acggaccccg gctacaactg cctgccctgc     1860
cccccacgct tcaccggctc acagcccttc ggccagggtg tcgaacatgc cacggccaac     1920
aaacaggtgt gcaagccccg taaccctgc acggatggga cccacgactg caacaagaac     1980
gccaagtgca actacctggg ccactatagc gaccccatgt accgctgcga gtgcaagcct     2040
ggctacgctg gcaatggcat catctgcggg gaggacacag acctggatgg ctggcccaat     2100
gagaacctgg tgtgcgtggc caatgcgact taccactgca aaaaggataa ttgccccaac     2160
cttcccaact cagggcagga agactatgac aaggatggaa ttggtgatgc ctgtgatgat     2220
gacgatgaca atgataaaat tccagatgac agggacaact gtccattcca ttacaaccca     2280
gctcagtatg actatgacag agatgatgtg ggagaccgct gtgacaactg tccctacaac     2340
cacaacccag atcaggcaga cacagacaac aatgggaag gagacgcctg tgctgcagac     2400
attgatggag acggtatcct caatgaacgg gacaactgcc agtacgtcta caatgtggac     2460
cagagagaca ctgatatgga tgggggttgga gatcagtgtg acaattgccc cttggaacac     2520
aatccggatc agctggactc tgactcagac cgcattggag ataccctgtga caacaatcag    2580
```

```
gatattgatg aagatggcca ccagaacaat ctggacaact gtccctatgt gcccaatgcc    2640
aaccaggctg accatgacaa agatggcaag ggagatgcct gtgaccacga tgatgacaac    2700
gatggcattc ctgatgacaa ggacaactgc agactcgtgc ccaatcccga ccagaaggac    2760
tctgacggcg atggtcgagg tgatgcctgc aaagatgatt ttgaccatga cagtgtgcca    2820
gacatcgatg acatctgtcc tgagaatgtt gacatcagtg agaccgattt ccgccgattc    2880
cagatgattc ctctggaccc caaagggaca tcccaaaatg accctaactg ggttgtacgc    2940
catcagggta agaactcgt  ccagactgtc aactgtgatc ctggactcgc tgtaggttat    3000
gatgagttta atgctgtgga cttcagtggc accttcttca tcaacaccga agggacgat     3060 gactatgctg gatttgtctt tggctaccag tccagcagcc gcttttatgt tgtgatgtgg    3120
aagcaagtca cccagtccta ctgggacacc aaccccacga gggctcaggg atactcgggc    3180
ctttctgtga agttgtaaa  ctccaccaca gggcctggcg agcacctgcg gaacgccctg    3240
tggcacacag gaaacacccc tggccaggtg cgcaccctgt ggcatgaccc tcgtcacata    3300
ggctggaaag atttcaccgc ctacagatgg cgtctcagcc acaggccaaa gacgggtttc    3360
attagagtgg tgatgtatga agggaagaaa atcatggctg actcaggacc catctatgat    3420
aaaacctatg ctggtggtag actagggttg tttgtcttct ctcaagaaat ggtgttcttc    3480
tctgacctga atacgaatg  tagagatccc taa                                3513

<210> SEQ ID NO 6
<211> LENGTH: 4395
<212> TYPE: DNA
<213> ORGANISM: Homo sapiens

<400> SEQUENCE: 6
atgttcagct ttgtggacct ccggctcctg ctcctcttag cggccaccgc cctcctgacg      60
cacggccaag aggaaggcca gtcgagggc  caagacgaag acatcccacc aatcacctgc     120
gtacagaacg gcctcaggta ccatgaccga gacgtgtgga acccgagcc  ctgccggatc     180 tgcgtctgcg acaacggcaa ggtgttgtgc gatgacgtga tctgtgacga gaccaagaac     240
tgccccggcg ccgaagtccc cgagggcgag tgctgtccg  tctgccccga cggctcagag     300
tcacccaccg accaagaaac caccggcgtc gagggaccca agggagacac tggcccccga     360
ggcccaaggg gacccgcagg cccccctggc cgagatggca tccctggaca gcctggactt     420
cccggacccc ccgaccccc  cggacctccc ggaccccctg gcctcggagg aaactttgct     480
ccccagctgt cttatggcta tgatgagaaa tcaaccggag gaatttccgt gcctggcccc     540
atgggtccct ctggtcctcg tggtctccct ggcccccctg gtgcacctgg tccccaaggc     600
ttccaaggtc cccctggtga gcctggcgag cctggagctt caggtcccat gggtccccga     660
ggtcccccag gtcccccg   aaagaatgga gatgatgggg aagctggaaa acctggtcgt     720
cctggtgagc gtgggcctcc tgggcctcag ggtgctcgag gattgcccgg aacagctggc     780
ctccctggaa tgaagggaca cagaggtttc agtggtttgg atggtgccaa gggagatgct     840
ggtcctgctg gtcctaaggg tgagcctggc agccctggtg aaaatggagc tcctggtcag     900
atgggccccc gtggcctgcc tggtgagaga ggtcgccctg gagcccctgg ccctgctggt     960
gctcgtggaa atgatggtgc tactggtgct gccgggcccc ctggtccca  cggccccgct    1020 ggtcctcctg gcttccctgg tgctgttggt gctaagggtg aagctggtcc ccaagggccc    1080
cgaggctctc aaggtcccca gggtgtgcgt ggtgagcctg gccccctgg  ccctgctggt    1140 gctgctggcc ctgctggaaa ccctggtgct gatggacagc ctggtgctaa aggtgccaat    1200
```

```
ggtgctcctg gtattgctgg tgctcctggc ttccctggtg cccgaggccc ctctggaccc      1260
cagggccccg gcggccctcc tggtcccaag ggtaacagcg gtgaacctgg tgctcctggc      1320
agcaaaggag acactggtgc taagggagag cctggccctg ttggtgttca aggaccccct      1380
ggccctgctg gagaggaagg aaagcgagga gctcgaggtg aacccggacc cactggcctg      1440
cccggacccc ctggcgagcg tggtggacct ggtagccgtg gtttccctgg cgcagatggt      1500
gttgctggtc ccaagggtcc cgctggtgaa cgtggttctc ctggccctgc tggccccaaa      1560
ggatctcctg gtgaagctgg tcgtcccggt gaagctggtc tgcctggtgc aagggtctg      1620 actgaaagcc ctggcagccc tggtcctgat ggcaaaactg gccccctgg tcccgccggt      1680 caagatggtc gccccggacc cccaggccca cctggtgccc gtggtcaggc tggtgtgatg      1740
ggattccctg gacctaaagg tgctgctgga gagcccggca aggctggaga gcaggtgtt      1800 cccggacccc ctggcgctgt cggtcctgct ggcaaagatg gagaggctgg agctcaggga      1860 cccctggcc ctgctggtcc cgctggcgag agaggtgaac aaggccctgc tggctccccc      1920
ggattccagg gtctccctgg tcctgctggt cctccaggtg aagcaggcaa acctggtgaa      1980
cagggtgttc ctggagacct tggcgcccct ggccctctg gagcaagagg cgagagaggt      2040
ttccctggcg agcgtggtgt gcaaggtccc cctggtcctg ctggtccccg aggggccaac      2100
ggtgctcccg gcaacgatgg tgctaagggt gatgctggtg cccctggagc tcccggtagc      2160
cagggcgccc ctggccttca gggaatgcct ggtgaacgtg gtgcagctgg tcttccaggg      2220
cctaagggtg acagaggtga tgctggtccc aaaggtgctg atggctctcc tggcaaagat      2280
ggcgtccgtg gtctgactgg ccccattggt cctcctggcc ctgctggtgc ccctggtgac      2340
aagggtgaaa gtggtcccag cggccctgct ggtcccactg gagctcgtgg tgccccgga      2400 gaccgtggtg agcctggtcc cccggccct gctggctttg ctgcccccc tggtgctgac      2460 ggccaacctg gtgctaaagg cgaacctggt gatgctggtg ctaaaggcga tgctggtccc      2520
cctggccctg ccggacccgc tggacccct ggccccattg gtaatgttgg tgctcctgga      2580
gccaaaggtg ctcgcggcag cgctggtccc cctggtgcta ctggtttccc tggtgctgct      2640
ggccgagtcg gtcctcctgg cccctctgga aatgctggac cccctggccc tcctggtcct      2700
gctggcaaag aaggcggcaa aggtcccgcgt ggtgagactg ccctgctgg acgtcctggt      2760 gaagttggtc ccctggtcc ccctggccct gctggcgaga aaggatcccc tggtgctgat      2820
ggtcctgctg gtgctcctgg tactcccggg cctcaaggta ttgctggaca gcgtggtgtg      2880
gtcggcctgc ctggtcagag aggagagaga ggcttccctg gtcttcctgg ccctctggt      2940 gaacctggca acaaggtcc ctctggagca agtggtgaac gtggtccccc tggtccatg      3000 ggccccctg gattggctgg accccctggt gaatctggac gtgaggggc tcctggtgcc      3060 gaaggttccc ctggacgaga cggttctcct ggcgccaagg gtgaccgtgg tgagaccggc      3120
cccgctggac ccctggtgc tcctggtgct cctggtgccc ctggccccgt ggccctgct      3180 ggcaagagtg gtgatcgtgg tgagactggt cctgctggtc ccaccggtcc tgtcggccct      3240
gttggcgccc gtggccccgc cggacccca ggccccgtg gtgacaaggg tgagacaggc      3300
gaacagggcg acagaggcat aaagggtcac cgtggcttct ctggcctcca gggtcccct      3360 ggccctcctg gctctcctgg tgaacaaggt ccctctggag cctctggtcc tgctggtccc      3420
cgaggtcccc ctggctctgc tggtgctcct ggcaaagatg gactcaacgg tctccctggc      3480
cccattgggc cccctggtcc tcgcggtcgc actggtgatg ctggtcctgt tggtccccc      3540
```

-continued

```
ggccctcctg gacctcctgg tcccctggt cctcccagcg ctggtttcga cttcagcttc    3600
ctgccccagc cacctcaaga gaaggctcac gatggtggcc gctactaccg ggctgatgat    3660
gccaatgtgg ttcgtgaccg tgacctcgag gtggacacca ccctcaagag cctgagccag    3720
cagatcgaga acatccggag cccagagggc agccgcaaga accccgcccg cacctgccgt    3780
gacctcaaga tgtgccactc tgactggaag agtggagagt actggattga ccccaaccaa    3840
ggctgcaacc tggatgccat caaagtcttc tgcaacatgg agactggtga cctgcgtg     3900 taccccactc agcccagtgt ggcccagaag aactggtaca tcagcaagaa ccccaaggac    3960
aagaggcatg tctggttcgg cgagagcatg accgatggat ccagttcga gtatggcggc     4020 cagggctccg accctgccga tgtggccatc agctgacct tcctgcgcct gatgtccacc    4080
gaggcctccc agaacatcac ctaccactgc aagaacagcg tggcctacat ggaccagcag    4140
actggcaacc tcaagaaggc cctgctcctc cagggctcca cgagatcga gatccgcgcc    4200 gagggcaaca gccgcttcac ctacagcgtc actgtcgatg ctgcacgag tcacaccgga    4260 gcctggggca agacagtgat tgaatacaaa accaccaaga cctcccgcct gcccatcatc    4320
gatgtggccc ccttggacgt tggtgcccca gaccaggaat tcggcttcga cgttggccct    4380
gtctgcttcc tgtaa                                                    4395
```

```
<210> SEQ ID NO 7
<211> LENGTH: 364
<212> TYPE: PRT
<213> ORGANISM: Homo sapiens

<400> SEQUENCE: 7

Met Pro Tyr Gln Tyr Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Ile Tyr Leu
    210                 215                 220
```

```
Glu Gly Thr Leu Leu Lys Pro Asn Met Val Thr Pro Gly His Ala Cys
225                 230                 235                 240

Thr Gln Lys Phe Ser His Glu Glu Ile Ala Met Ala Thr Val Thr Ala
            245                 250                 255

Leu Arg Arg Thr Val Pro Pro Ala Val Thr Gly Ile Thr Phe Leu Ser
        260                 265                 270

Gly Gly Gln Ser Glu Glu Ala Ser Ile Asn Leu Asn Ala Ile Asn
        275                 280                 285

Lys Cys Pro Leu Leu Lys Pro Trp Ala Leu Thr Phe Ser Tyr Gly Arg
290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
            340                 345                 350

Ala Ser Glu Ser Leu Phe Val Ser Asn His Ala Tyr
            355                 360

<210> SEQ ID NO 8
<211> LENGTH: 418
<212> TYPE: PRT
<213> ORGANISM: Homo sapiens

<400> SEQUENCE: 8

Met Ala Arg Arg Lys Pro Glu Gly Ser Ser Phe Asn Met Thr His Leu
1               5                   10                  15

Ser Met Ala Met Ala Phe Ser Phe Pro Pro Val Ala Ser Gly Gln Leu
            20                  25                  30

His Pro Gln Leu Gly Asn Thr Gln His Thr Glu Leu Gly Lys Glu
            35                  40                  45

Leu Ala Thr Thr Ser Thr Met Pro Tyr Gln Tyr Pro Ala Leu Thr Pro
    50                  55                  60

Glu Gln Lys Lys Glu Leu Ser Asp Ile Ala His Arg Ile Val Ala Pro
65                  70                  75                  80

Gly Lys Gly Ile Leu Ala Ala Asp Glu Ser Thr Gly Ser Ile Ala Lys
                85                  90                  95

Arg Leu Gln Ser Ile Gly Thr Glu Asn Thr Glu Glu Asn Arg Arg Phe
            100                 105                 110

Tyr Arg Gln Leu Leu Leu Thr Ala Asp Asp Arg Val Asn Pro Cys Ile
        115                 120                 125

Gly Gly Val Ile Leu Phe His Glu Thr Leu Tyr Gln Lys Ala Asp Asp
    130                 135                 140

Gly Arg Pro Phe Pro Gln Val Ile Lys Ser Lys Gly Gly Val Val Gly
145                 150                 155                 160

Ile Lys Val Asp Lys Gly Val Val Pro Leu Ala Gly Thr Asn Gly Glu
                165                 170                 175

Thr Thr Thr Gln Gly Leu Asp Gly Leu Ser Glu Arg Cys Ala Gln Tyr
            180                 185                 190

Lys Lys Asp Gly Ala Asp Phe Ala Lys Trp Arg Cys Val Leu Lys Ile
        195                 200                 205

Gly Glu His Thr Pro Ser Ala Leu Ala Ile Met Glu Asn Ala Asn Val
    210                 215                 220

Leu Ala Arg Tyr Ala Ser Ile Cys Gln Gln Asn Gly Ile Val Pro Ile
```

```
                225                 230                 235                 240
Val Glu Pro Glu Ile Leu Pro Asp Gly Asp His Asp Leu Lys Arg Cys
                245                 250                 255

Gln Tyr Val Thr Glu Lys Val Leu Ala Ala Val Tyr Lys Ala Leu Ser
                260                 265                 270

Asp His His Ile Tyr Leu Glu Gly Thr Leu Leu Lys Pro Asn Met Val
                275                 280                 285

Thr Pro Gly His Ala Cys Thr Gln Lys Phe Ser His Glu Glu Ile Ala
                290                 295                 300

Met Ala Thr Val Thr Ala Leu Arg Arg Thr Val Pro Pro Ala Val Thr
305                 310                 315                 320

Gly Ile Thr Phe Leu Ser Gly Gly Gln Ser Glu Glu Glu Ala Ser Ile
                325                 330                 335

Asn Leu Asn Ala Ile Asn Lys Cys Pro Leu Leu Lys Pro Trp Ala Leu
                340                 345                 350

Thr Phe Ser Tyr Gly Arg Ala Leu Gln Ala Ser Ala Leu Lys Ala Trp
                355                 360                 365

Gly Gly Lys Lys Glu Asn Leu Lys Ala Ala Gln Glu Glu Tyr Val Lys
                370                 375                 380

Arg Ala Leu Ala Asn Ser Leu Ala Cys Gln Gly Lys Tyr Thr Pro Ser
385                 390                 395                 400

Gly Gln Ala Gly Ala Ala Ser Glu Ser Leu Phe Val Ser Asn His
                405                 410                 415

Ala Tyr

<210> SEQ ID NO 9
<211> LENGTH: 175
<212> TYPE: PRT
<213> ORGANISM: Homo sapiens

<400> SEQUENCE: 9

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
                20                  25                  30

Ser Leu Gly Phe Tyr Phe Asp Arg Asp Asp Val Ala Leu Glu Gly Val
                35                  40                  45

Ser His Phe Phe Arg Glu Leu Ala Glu Glu Lys Arg Glu Gly Tyr Glu
                50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
                100                 105                 110

Asp Leu His Ala Leu Gly Ser Ala Arg Thr Asp Pro His Leu Cys Asp
                115                 120                 125

Phe Leu Glu Thr His Phe Leu Asp Glu Glu Val Lys Leu Ile Lys Lys
                130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175
```

```
<210> SEQ ID NO 10
<211> LENGTH: 585
<212> TYPE: PRT
<213> ORGANISM: Homo sapiens

<400> SEQUENCE: 10

Met Thr Pro Pro Arg Leu Phe Trp Val Trp Leu Leu Val Ala Gly Thr
 1               5                  10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
    50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
                165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205

Leu Arg Tyr Phe Tyr Ser Arg Arg Ile Asp Ile Thr Leu Ser Ser Val
    210                 215                 220

Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
                245                 250                 255

Phe Gln Met Pro Leu Asp Leu Tyr Ala Tyr Ala Val Ala Thr Gly Asp
            260                 265                 270

Ala Leu Leu Glu Lys Leu Cys Leu Gln Phe Leu Ala Trp Asn Phe Glu
        275                 280                 285

Ala Leu Thr Gln Ala Glu Ala Trp Pro Ser Val Pro Thr Asp Leu Leu
    290                 295                 300

Gln Leu Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
                325                 330                 335

Glu Glu Val Glu Gly Leu Val Glu Lys Ile Arg Phe Pro Met Met Leu
            340                 345                 350

Pro Glu Glu Leu Phe Glu Leu Gln Phe Asn Leu Ser Leu Tyr Trp Ser
        355                 360                 365

His Glu Ala Leu Phe Gln Lys Lys Thr Leu Gln Ala Leu Glu Phe His
    370                 375                 380
```

-continued

```
Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
            405                 410                 415

Phe Val Thr Asp Ser Ser Trp Ser Ala Arg Lys Ser Gln Leu Val Tyr
        420                 425                 430

Gln Ser Arg Arg Gly Pro Leu Val Lys Tyr Ser Ser Asp Tyr Phe Gln
    435                 440                 445

Ala Pro Ser Asp Tyr Arg Tyr Tyr Pro Tyr Gln Ser Phe Gln Thr Pro
450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
            485                 490                 495

Ser Ser Asp Glu Leu Pro Val Leu Gly Leu Thr Lys Ser Gly Gly Ser
        500                 505                 510

Asp Arg Thr Ile Ala Tyr Glu Asn Lys Ala Leu Met Leu Cys Glu Gly
    515                 520                 525

Leu Phe Val Ala Asp Val Thr Asp Phe Glu Gly Trp Lys Ala Ala Ile
530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
            565                 570                 575

Tyr Leu Thr Asn Ser Ser Gly Val Asp
        580                 585

<210> SEQ ID NO 11
<211> LENGTH: 1170
<212> TYPE: PRT
<213> ORGANISM: Homo sapiens

<400> SEQUENCE: 11

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
            85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
            165                 170                 175
```

```
Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
            195                 200                 205

Gln Gly Val Leu Gln Asn Val Arg Phe Val Phe Gly Thr Thr Pro Glu
            210                 215                 220

Asp Ile Leu Arg Asn Lys Gly Cys Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
            275                 280                 285

Thr Ile Val Thr Thr Leu Gln Asp Ser Ile Arg Lys Val Thr Glu Glu
            290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
            355                 360                 365

Cys Pro Arg Cys Trp Pro Ser Asp Ser Ala Asp Asp Gly Trp Ser Pro
            370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
            435                 440                 445

Val Thr Cys Gly Asp Gly Val Ile Thr Arg Ile Arg Leu Cys Asn Ser
450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
            485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
            515                 520                 525

Lys Asp Cys Val Gly Asp Val Thr Glu Asn Gln Ile Cys Asn Lys Gln
            530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
            565                 570                 575

Pro Gly Tyr Ser Gly Asn Gly Ile Gln Cys Thr Asp Val Asp Glu Cys
            580                 585                 590
```

-continued

Lys Glu Val Pro Asp Ala Cys Phe Asn His Asn Gly Glu His Arg Cys
        595                 600                 605

Glu Asn Thr Asp Pro Gly Tyr Asn Cys Leu Pro Cys Pro Pro Arg Phe
    610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
        660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
    690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
        740                 745                 750

Asn Cys Pro Phe His Tyr Asn Pro Ala Gln Tyr Asp Tyr Asp Arg Asp
    755                 760                 765

Asp Val Gly Asp Arg Cys Asp Asn Cys Pro Tyr Asn His Asn Pro Asp
770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
        805                 810                 815

Tyr Asn Val Asp Gln Arg Asp Thr Asp Met Asp Gly Val Gly Asp Gln
    820                 825                 830

Cys Asp Asn Cys Pro Leu Glu His Asn Pro Asp Gln Leu Asp Ser Asp
        835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
        900                 905                 910

Val Pro Asn Pro Asp Gln Lys Asp Ser Asp Gly Asp Gly Arg Gly Asp
    915                 920                 925

Ala Cys Lys Asp Asp Phe Asp His Asp Ser Val Pro Asp Ile Asp Asp
        930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
        980                 985                 990

Asp Pro Gly Leu Ala Val Gly Tyr Asp Glu Phe Asn Ala Val Asp Phe
    995                 1000                1005

Ser Gly Thr Phe Phe Ile Asn Thr Glu Arg Asp Asp Asp Tyr Ala

-continued

```
              1010                1015                1020

Gly Phe Val Phe Gly Tyr Gln Ser Ser Ser Arg Phe Tyr Val Val
            1025                1030                1035

Met Trp Lys Gln Val Thr Gln Ser Tyr Trp Asp Thr Asn Pro Thr
            1040                1045                1050

Arg Ala Gln Gly Tyr Ser Gly Leu Ser Val Lys Val Val Asn Ser
            1055                1060                1065

Thr Thr Gly Pro Gly Glu His Leu Arg Asn Ala Leu Trp His Thr
            1070                1075                1080

Gly Asn Thr Pro Gly Gln Val Arg Thr Leu Trp His Asp Pro Arg
            1085                1090                1095

His Ile Gly Trp Lys Asp Phe Thr Ala Tyr Arg Trp Arg Leu Ser
            1100                1105                1110

His Arg Pro Lys Thr Gly Phe Ile Arg Val Val Met Tyr Glu Gly
            1115                1120                1125

Lys Lys Ile Met Ala Asp Ser Gly Pro Ile Tyr Asp Lys Thr Tyr
            1130                1135                1140

Ala Gly Gly Arg Leu Gly Leu Phe Val Phe Ser Gln Glu Met Val
            1145                1150                1155

Phe Phe Ser Asp Leu Lys Tyr Glu Cys Arg Asp Pro
            1160                1165                1170

<210> SEQ ID NO 12
<211> LENGTH: 1464
<212> TYPE: PRT
<213> ORGANISM: Homo sapiens

<400> SEQUENCE: 12

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
            35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
            195                 200                 205
```

-continued

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro

-continued

```
            625                 630                 635                 640

Gly Phe Gln Gly Leu Pro Gly Ala Gly Pro Gly Glu Ala Gly
                    645                 650                 655

Lys Pro Gly Glu Gln Gly Val Pro Gly Asp Leu Gly Ala Pro Gly Pro
                660                 665                 670

Ser Gly Ala Arg Gly Glu Arg Gly Phe Pro Gly Glu Arg Gly Val Gln
                675                 680                 685

Gly Pro Pro Gly Pro Ala Gly Pro Arg Gly Ala Asn Gly Ala Pro Gly
            690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                    725                 730                 735

Gly Leu Pro Gly Pro Lys Gly Asp Arg Gly Asp Ala Gly Pro Lys Gly
                740                 745                 750

Ala Asp Gly Ser Pro Gly Lys Asp Gly Val Arg Gly Leu Thr Gly Pro
                755                 760                 765

Ile Gly Pro Pro Gly Pro Ala Gly Ala Pro Gly Asp Lys Gly Glu Ser
        770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
        850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
                900                 905                 910

Thr Gly Pro Ala Gly Arg Pro Gly Glu Val Gly Pro Pro Gly Pro Pro
                915                 920                 925

Gly Pro Ala Gly Glu Lys Gly Ser Pro Gly Ala Asp Gly Pro Ala Gly
            930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
                980                 985                 990

Glu Arg Gly Pro Pro Gly Pro Met  Gly Pro Pro Gly Leu Ala Gly Pro
            995                 1000                1005

Pro Gly Glu Ser Gly Arg Glu  Gly Ala Pro Gly Ala  Glu Gly Ser
    1010                1015                1020

Pro Gly Arg Asp Gly Ser Pro  Gly Ala Lys Gly Asp  Arg Gly Glu
    1025                1030                1035

Thr Gly Pro Ala Gly Pro Pro  Gly Ala Pro Gly Ala  Pro Gly Ala
    1040                1045                1050
```

-continued

Pro Gly Pro Val Gly Pro Ala Gly Lys Ser Gly Asp Arg Gly Glu
    1055            1060              1065

Thr Gly Pro Ala Gly Pro Thr Gly Pro Val Gly Pro Val Gly Ala
    1070            1075              1080

Arg Gly Pro Ala Gly Pro Gln Gly Pro Arg Gly Asp Lys Gly Glu
    1085            1090              1095

Thr Gly Glu Gln Gly Asp Arg Gly Ile Lys Gly His Arg Gly Phe
    1100            1105              1110

Ser Gly Leu Gln Gly Pro Pro Gly Pro Pro Gly Ser Pro Gly Glu
    1115            1120              1125

Gln Gly Pro Ser Gly Ala Ser Gly Pro Ala Gly Pro Arg Gly Pro
    1130            1135              1140

Pro Gly Ser Ala Gly Ala Pro Gly Lys Asp Gly Leu Asn Gly Leu
    1145            1150              1155

Pro Gly Pro Ile Gly Pro Pro Gly Pro Arg Gly Arg Thr Gly Asp
    1160            1165              1170

Ala Gly Pro Val Gly Pro Pro Gly Pro Pro Gly Pro Pro Gly Pro
    1175            1180              1185

Pro Gly Pro Pro Ser Ala Gly Phe Asp Phe Ser Phe Leu Pro Gln
    1190            1195              1200

Pro Pro Gln Glu Lys Ala His Asp Gly Gly Arg Tyr Tyr Arg Ala
    1205            1210              1215

Asp Asp Ala Asn Val Val Arg Asp Arg Asp Leu Glu Val Asp Thr
    1220            1225              1230

Thr Leu Lys Ser Leu Ser Gln Gln Ile Glu Asn Ile Arg Ser Pro
    1235            1240              1245

Glu Gly Ser Arg Lys Asn Pro Ala Arg Thr Cys Arg Asp Leu Lys
    1250            1255              1260

Met Cys His Ser Asp Trp Lys Ser Gly Glu Tyr Trp Ile Asp Pro
    1265            1270              1275

Asn Gln Gly Cys Asn Leu Asp Ala Ile Lys Val Phe Cys Asn Met
    1280            1285              1290

Glu Thr Gly Glu Thr Cys Val Tyr Pro Thr Gln Pro Ser Val Ala
    1295            1300              1305

Gln Lys Asn Trp Tyr Ile Ser Lys Asn Pro Lys Asp Lys Arg His
    1310            1315              1320

Val Trp Phe Gly Glu Ser Met Thr Asp Gly Phe Gln Phe Glu Tyr
    1325            1330              1335

Gly Gly Gln Gly Ser Asp Pro Ala Asp Val Ala Ile Gln Leu Thr
    1340            1345              1350

Phe Leu Arg Leu Met Ser Thr Glu Ala Ser Gln Asn Ile Thr Tyr
    1355            1360              1365

His Cys Lys Asn Ser Val Ala Tyr Met Asp Gln Gln Thr Gly Asn
    1370            1375              1380

Leu Lys Lys Ala Leu Leu Leu Gln Gly Ser Asn Glu Ile Glu Ile
    1385            1390              1395

Arg Ala Glu Gly Asn Ser Arg Phe Thr Tyr Ser Val Thr Val Asp
    1400            1405              1410

Gly Cys Thr Ser His Thr Gly Ala Trp Gly Lys Thr Val Ile Glu
    1415            1420              1425

Tyr Lys Thr Thr Lys Thr Ser Arg Leu Pro Ile Ile Asp Val Ala
    1430            1435              1440

```
Pro Leu Asp Val Gly Ala Pro  Asp Gln Glu Phe Gly  Phe Asp Val
   1445                1450                 1455

Gly Pro  Val Cys Phe Leu
   1460

<210> SEQ ID NO 13
<211> LENGTH: 1257
<212> TYPE: DNA
<213> ORGANISM: Homo sapiens

<400> SEQUENCE: 13
atgcaggccc tggtgctact cctctgcatt ggagccctcc tcgggcacag cagctgccag      60
aaccctgcca gcccccggga ggagggctcc ccagaccccg acagcacagg ggcgctggtg     120
gaggaggagg atcctttctt caaagtcccc gtgaacaagc tggcagcggc tgtctccaac     180
ttcggctatg acctgtaccg ggtgcgatcc agcacgagcc ccacgaccaa cgtgctcctg     240
tctcctctca gtgtggccac ggccctctcg ccctctcgc tgggagcgga gcagcgaaca      300
gaatccatca ttcaccgggc tctctactat gacttgatca gcagcccaga catccatggt     360
acctataagg agctccttga cacggtcact gcccccaga agaacctcaa gagtgcctcc     420
cggatcgtct tgagaagaa gctgcgcata aaatccagct tgtggcacc tctggaaaag      480 tcatatggga ccaggcccag agtcctgacg ggcaaccctc gcttggacct gcaagagatc     540
aacaactggg tgcaggcgca gatgaaaggg aagctcgcca ggtccacaaa ggaaattccc     600
gatgagatca gcattctcct ctcggtgtg gcgcacttca gggggcagtg ggtaacaaag     660
tttgactcca gaaagacttc cctcgaggat ttctacttgg atgaagagag gaccgtgagg     720
gtccccatga tgtcggaccc taaggctgtt ttacgctatg gcttggattc agatctcagc     780
tgcaagattg cccagctgcc cttgaccgga agcatgagta tcatcttctt cctgcccctg     840
aaagtgaccc agaatttgac cttgatagag gagagcctca cctccgagtt cattcatgac     900
atagaccgag aactgaagac cgtgcaggcg gtcctcactg tccccaagct gaagctgagt     960
tatgaaggcg aagtcaccaa gtccctgcag gagatgaagc tgcaatcctt gtttgattca    1020
ccagacttta gcaagatcac aggcaaaccc atcaagctga ctcaggtgga acaccgggct    1080
ggctttgagt ggaacgagga tggggcggga accaccccca gcccagggct gcagcctgcc    1140
cacctcacct tcccgctgga ctatcacctt aaccagcctt tcatcttcgt actgagggac    1200
acagacacag ggccccttct cttcattggc aagattctgg accccagggg ccccctaa      1257

<210> SEQ ID NO 14
<211> LENGTH: 2100
<212> TYPE: DNA
<213> ORGANISM: Homo sapiens

<400> SEQUENCE: 14
atgaggtggc tgcttctcta ttatgctctg tgcttctccc tgtcaaaggc ttcagcccac      60
accgtggagc taaacaatat gtttggccag atccagtcgc ctggttatcc agactcctat     120
cccagtgatt cagaggtgac ttggaatatc actgtcccag atgggtttcg gatcaagctt     180
tacttcatgc acttcaactt ggaatcctcc taccttgtg aatatgacta tgtgaaggta     240
gaaactgagg accaggtgct ggcaaccttc tgtggcaggg agaccacaga cacagagcag     300
actcccggcc aggaggtggt cctctcccct ggctccttca tgtccatcac tttccggtca     360
gatttctcca atgaggagcg tttcacaggc tttgatgccc actacatggc tgtggatgtg     420
gacgagtgca aggagaggga ggacgaggag ctgtcctgtg accactactg ccacaactac     480
```

```
attggcggct actactgctc ctgccgcttc ggctacatcc tccacacaga caacaggacc      540
tgccgagtgg agtgcagtga caacctcttc actcaaagga ctggggtgat caccagccct      600
gacttcccaa acccttaccc caagagctct gaatgcctgt ataccatcga gctggaggag      660
ggtttcatgg tcaacctgca gtttgaggac atatttgaca ttgaggacca tcctgaggtg      720
ccctgcccct atgactacat caagatcaaa gttggtccaa aagttttggg gcctttctgt      780
ggagagaaag ccccagaacc catcagcacc cagagccaca gtgtcctgat cctgttccat      840
agtgacaact cgggagagaa ccggggctgg aggctctcat acagggctgc aggaaatgag      900
tgcccagagc tacagcctcc tgtccatggg aaaatcgagc cctcccaagc caagtatttc      960
ttcaaagacc aagtgctcgt cagctgtgac acaggctaca agtgctgaa ggataatgtg      1020 gagatggaca cattccagat tgagtgtctg aaggatggga cgtggagtaa caagattccc     1080
acctgtaaaa ttgtagactg tagagcccca ggagagctgg aacacgggct gatcaccttc      1140
tctacaagga caacctcac cacatacaag tctgagatca aatactcctg tcaggagccc      1200
tattacaaga tgctcaacaa taacacaggt atatatacct gttctgccca aggagtctgg      1260
atgaataaag tattggggag aagcctaccc acctgccttc cagtgtgtgg gctccccaag      1320
ttctcccgga agctgatggc caggatcttc aatggacgcc cagcccagaa aggcaccact      1380
ccctggattg ccatgctgtc acacctgaat gggcagccct tctgcggagg ctcccttcta      1440
ggctccagct ggatcgtgac cgccgcacac tgcctccacc agtcactcga tccggaagat      1500
ccgaccctac gtgattcaga cttgctcagc ccttctgact tcaaaatcat cctgggcaag      1560
cattggaggc tccggtcaga tgaaaatgaa cagcatctcg gcgtcaaaca caccactctc      1620
cacccccagt atgatcccaa cacattcgag aatgacgtgg ctctggtgga gctgttggag      1680
agcccagtgc tgaatgcctt cgtgatgccc atctgtctgc ctgagggacc ccagcaggaa      1740
ggagccatgg tcatcgtcag cggctggggg aagcagttct tgcaaaggtt cccagagacc      1800
ctgatggaga ttgaaatccc gattgttgac cacagcacct gccagaaggc ttatgccccg      1860
ctgaagaaga aagtgaccag ggacatgatc tgtgctgggg agaaggaagg gggaaaggac      1920
gcctgtgcgg gtgactctgg aggccccatg gtgaccctga atagagaaag aggccagtgg      1980
tacctggtgg gcactgtgtc ctggggtgat gactgtggga agaaggaccg ctacggagta      2040
tactcttaca tccaccacaa caaggactgg atccagaggg tcaccggagt gaggaactga      2100
```

<210> SEQ ID NO 15
<211> LENGTH: 2349
<212> TYPE: DNA
<213> ORGANISM: Homo sapiens

<400> SEQUENCE: 15

```
atggctccgc accgccccgc gcccgcgctg ctttgcgcgc tgtccctggc gctgtgcgcg       60
ctgtcgctgc ccgtccgcgc ggccactgcg tcgcgggggg cgtcccaggc ggggcgcccc      120
caggggcggg tgcccgaggc gcggcccaac agcatggtgg tggaacaccc cgagttcctc      180
aaggcaggga aggagcctgg cctgcagatc tggcgtgtgg agaagttcga tctggtgccc      240
gtgcccacca acctttatgg agacttcttc acgggcgacg cctacgtcat cctgaagaca      300
gtgcagctga ggaacggaaa tctgcagtat gacctccact actggctggg caatgagtgc      360
agccaggatg agagcggggc ggccgccatc tttaccgtgc agctggatga ctacctgaac      420
ggccgggccg tgcagcaccg tgaggtccag ggcttcgagt cggccaccct cctaggctac      480
```

| | |
|---|---|
| ttcaagtctg gcctgaagta caagaaagga ggtgtggcat caggattcaa gcacgtggta | 540 |
| cccaacgagg tggtggtgca gagactcttc caggtcaaag gcggcgtgt ggtccgtgcc | 600 |
| accgaggtac ctgtgtcctg ggagagcttc aacaatggcg actgcttcat cctggacctg | 660 |
| ggcaacaaca tccaccagtg gtgtggttcc aacagcaatc ggtatgaaag actgaaggcc | 720 |
| acacaggtgt ccaagggcat ccgggacaac gagcggagtg gccgggcccg agtgcacgtg | 780 |
| tctgaggagg gcactgagcc cgaggcgatg ctccaggtgc tgggcccaa gccggctctg | 840 |
| cctgcaggta ccgaggacac cgccaaggag gatgcggcca accgcaagct ggccaagctc | 900 |
| tacaaggtct ccaatggtgc agggaccatg tccgtctccc tcgtggctga tgagaacccc | 960 |
| ttcgcccagg gggccctgaa gtcagaggac tgcttcatcc tggaccacgg caaagatggg | 1020 |
| aaaatctttg tctggaaagg caagcaggca aacacggagg agaggaaggc tgccctcaaa | 1080 |
| acagcctctg acttcatcac caagatggac taccccaagc agactcaggt ctcggtcctt | 1140 |
| cctgagggcg gtgagacccc actgttcaag cagttcttca agaactggcg ggacccagac | 1200 |
| cagacagatg gcctgggctt gtcctacctt tccagccata tcgccaacgt ggagcgggtg | 1260 |
| cccttcgacg ccgccaccct gcacacctcc actgccatgg ccgcccagca cggcatggat | 1320 |
| gacgatggca caggccagaa acagatctgg agaatcgaag gttccaacaa ggtgcccgtg | 1380 |
| gaccctgcca catatggaca gttctatgga ggcgacagct acatcattct gtacaactac | 1440 |
| cgccatggtg gccgccaggg gcagataatc tataactggc agggtgccca gtctacccag | 1500 |
| gatgaggtcg ctgcatctgc catcctgact gctcagctgg atgaggagct gggaggtacc | 1560 |
| cctgtccaga gccgtgtggt ccaaggcaag gagcccgccc acctcatgag cctgtttggt | 1620 |
| gggaagccca tgatcatcta aagggcggc acctcccgcg agggcgggca gacagcccct | 1680 |
| gccagcaccc gcctcttcca ggtccgcgcc aacagcgctg gagccacccg ggctgttgag | 1740 |
| gtattgccta aggctggtgc actgaactcc aacgatgcct ttgttctgaa accccctca | 1800 |
| gccgcctacc tgtgggtggg tacaggagcc agcgaggcag agaagacggg ggcccaggag | 1860 |
| ctgctcaggg tgctgcgggc ccaacctgtg caggtggcag aaggcagcga gccagatggc | 1920 |
| ttctgggagg ccctgggcgg gaaggctgcc taccgcacat ccccacggct gaaggacaag | 1980 |
| aagatggatg cccatcctcc tcgcctcttt gcctgctcca acaagattgg acgttttgtg | 2040 |
| atcgaagagg ttcctggtga gctcatgcag gaagacctgg caacggatga cgtcatgctt | 2100 |
| ctggacacct gggaccaggt cttgtctgg gttggaaagg attctcaaga agaagaaaag | 2160 |
| acagaagcct tgacttctgc taagcggtac atcgagacgg acccagccaa tcgggatcgg | 2220 |
| cggacgccca tcaccgtggt gaagcaaggc tttgagcctc cctcctttgt gggctggttc | 2280 |
| cttggctggg atgatgatta ctggtctgtg gaccccttgg acagggccat ggctgagctg | 2340 |
| gctgcctga | 2349 |

<210> SEQ ID NO 16
<211> LENGTH: 1017
<212> TYPE: DNA
<213> ORGANISM: Homo sapiens

<400> SEQUENCE: 16

| | |
|---|---|
| atgagtctaa gtgcatttac tctcttcctg gcattgattg gtggtaccag tggccagtac | 60 |
| tatgattatg atttcccct atcaatttat gggcaatcat caccaaactg tgcaccagaa | 120 |
| tgtaactgcc ctgaaagcta cccaagtgcc atgtactgtg atgagctgaa attgaaaagt | 180 |
| gtaccaatgg tgcctcctgg aatcaagtat ctttaccttta ggaataacca gattgaccat | 240 |

```
attgatgaaa aggcctttga gaatgtaact gatctgcagt ggctcattct agatcacaac      300
cttctagaaa actccaagat aaaagggaga gttttctcta aattgaaaca actgaagaag      360
ctgcatataa accacaacaa cctgacagag tctgtgggcc cacttcccaa atctctggag      420
gatctgcagc ttactcataa caagatcaca agctgggct cttttgaagg attggtaaac       480
ctgaccttca tccatctcca gcacaatcgg ctgaagagg atgctgtttc agctgctttt       540
aaaggtctta atcactcga ataccttgac ttgagcttca atcagatagc cagactgcct       600
tctggtctcc ctgtctctct tctaactctc tacttagaca acaataagat cagcaacatc      660
cctgatgagt atttcaagcg ttttaatgca ttgcagtatc tgcgtttatc tcacaacgaa      720
ctggctgata gtggaatacc tggaaattct ttcaatgtgt catccctggt tgagctggat      780
ctgtcctata acaagcttaa aaacatacca actgtcaatg aaaaccttga aaactattac      840
ctggaggtca atcaacttga gaagtttgac ataaagagct tctgcaagat cctggggcca      900
ttatcctact ccaagatcaa gcatttgcgt ttggatggca atcgcatctc agaaaccagt      960
cttccaccgg atatgtatga atgtctacgt gttgctaacg aagtcactct taattaa       1017

<210> SEQ ID NO 17
<211> LENGTH: 3366
<212> TYPE: DNA
<213> ORGANISM: Homo sapiens

<400> SEQUENCE: 17
atgagcaaac tcagaatggt gctacttgaa gactctggat ctgctgactt cagaagacat       60
tttgtcaact tgagtcccct caccattact gtggtcttac ttctcagtgc ctgttttgtc      120
accagttctc ttggaggaac agacaaggag ctgaggctag tggatggtga aaacaagtgt      180
agcgggagag tggaagtgaa agtccaggag gagtggggaa cggtgtgtaa taatggctgg      240
agcatggaag cggtctctgt gatttgtaac cagctgggat gtccaactgc tatcaaagcc      300
cctggatggg ctaattccag tgcaggttct ggacgcattt ggatggatca tgtttcttgt      360
cgtgggaatg agtcagctct ttgggattgc aaacatgatg gatggggaaa gcatagtaac      420
tgtactcacc aacaagatgc tggagtgacc tgctcagatg gatccaattt ggaaatgagg      480
ctgacgcgtg gagggaatat gtgttctgga agaatagaga tcaaattcca aggacggtgg      540
ggaacagtgt gtgatgataa cttcaacata gatcatgcat ctgtcatttg tagacaactt      600
gaatgtggaa gtgctgtcag ttttctctgg tcatctaatt ttggagaagg ctctggacca      660
atctggtttg atgatcttat atgcaacgga aatgagtcag ctctctggaa ctgcaaacat      720
caaggatggg gaaagcataa ctgtgatcat gctgaggatg ctggagtgat tgctcaaag       780 ggagcagatc tgagcctgag actggtagat ggagtcactg aatgttcagg aagattagaa      840
gtgagattcc aaggagaatg ggggacaata tgtgatgacg ctgggacag ttacgatgct       900 gctgtggcat gcaagcaact gggatgtcca actgccgtca cagccattgg tcgagttaac      960
gccagtaagg gatttggaca catctggctt gacagcgttt cttgccaggg acatgaacct     1020
gctatctggc aatgtaaaca ccatgaatgg ggaaagcatt attgcaatca caatgaagat     1080
gctggcgtga catgttctga tggatcagat ctggagctaa gacttagagg tggaggcagc     1140
cgctgtgctg ggacagttga ggtggagatt cagagactgt tagggaaggt gtgtgacaga     1200
ggctggggac tgaagaagagc tgatgtggtt tgcaggcagc tgggatgtgg atctgcactc     1260
aaaacatctt atcaagtgta ctccaaaatc caggcaacaa acacatggct gtttctaagt     1320
```

```
agctgtaacg gaaatgaaac ttctctttgg gactgcaaga actggcaatg gggtggactt    1380
acctgtgatc actatgaaga agccaaaatt acctgctcag cccacaggga acccagactg    1440
gttggagggg acattccctg ttctggacgt gttgaagtga agcatggtga cacgtggggc    1500
tccatctgtg attcggactt ctctctggaa gctgccagcg ttctatgcag ggaattacag    1560
tgtggcacag ttgtctctat cctgggggga gctcactttg gagagggaaa tggacagatc    1620
tgggctgaag aattccagtg tgagggacat gagtcccatc tttcactctg cccagtagca    1680
ccccgcccag aaggaacttg tagccacagc agggatgttg gagtagtctg ctcaagatac    1740
acagaaattc gcttggtgaa tggcaagacc ccgtgtgagg gcagagtgga gctcaaaacg    1800
cttggtgcct ggggatccct ctgtaactct cactgggaca tagaagatgc ccatgttctt    1860
tgccagcagc ttaaatgtgg agttgccctt tctaccccag gaggagcacg tttttggaaaa   1920 ggaaatggtc agatctggag gcatatgttt cactgcactg ggactgagca gcacatggga    1980
gattgtcctg taactgctct aggtgcttca ttatgtcctt cagagcaagt ggcctctgta    2040
atctgctcag gaaccagtc ccaaacactg tcctcgtgca attcatcgtc tttgggccca     2100
acaaggccta ccattccaga gaaagtgct gtggcctgca tagagagtgg tcaacttcgc     2160
ctggtaaatg gaggaggtcg ctgtgctggg agagtagaga tctatcatga gggctcctgg    2220
ggcaccatct gtgatgacag ctgggacctg agtgatgccc acgtggtttg cagacagctg    2280
ggctgtggag aggccattaa tgccactggt tctgctcatt tggggaagg aacagggccc      2340 atctggctgg atgagatgaa atgcaatgga aagaatccc gcatttggca gtgccattca     2400
cacggctggg ggcagcaaaa ttgcaggcac aaggaggatg cgggagttat ctgctcagaa    2460
ttcatgtctc tgagactgac cagtgaagcc agcagagagg cctgtgcagg gcgtctggaa    2520
gttttttaca atggagcttg gggcactgtt ggcaagagta gcatgtctga aaccactgtg     2580
ggtgtggtgt gcaggcagct gggctgtgca gacaaaggga aaatcaaccc tgcatcttta    2640
gacaaggcca tgtccattcc catgtgggtg gacaatgttc agtgtccaaa aggacctgac    2700
acgctgtggc agtgcccatc atctccatgg gagaagagac tggccagccc ctcggaggag   2760
acctggatca catgtgacaa caagataaga cttcaggaag acccacttc ctgttctgga     2820 cgtgtggaga tctggcatgg aggttcctgg gggacagtgt gtgatgactc ttgggacttg    2880
gacgatgctc aggtggtgtg tcaacaactt ggctgtggtc cagctttgaa agcattcaaa   2940
gaagcagagt ttggtcaggg gactggaccg atatggctca atgaagtgaa gtgcaaaggg   3000
aatgagtctt ccttgtggga ttgtcctgcc agacgctggg gccatagtga gtgtgggcac    3060
aaggaagacg ctgcagtgaa ttgcacagat atttcagtgc agaaaacccc acaaaaagcc    3120
acaacaggtc gctcatcccg tcagtcatcc tttattgcag tcgggatcct tgggggttgtt  3180 ctgttggcca ttttcgtcgc attattcttc ttgactaaaa agcgaagaca gagacagcgg    3240
cttgcagttt cctcaagagg agagaactta gtccaccaaa ttcaataccg ggagatgaat    3300
tcttgcctga atgcagatga tctggaccta atgaattcct caggaggcca ttctgagcca    3360
cactga                                                              3366

<210> SEQ ID NO 18
<211> LENGTH: 1620
<212> TYPE: DNA
<213> ORGANISM: Homo sapiens

<400> SEQUENCE: 18
atgaagccgg cggcgcggga ggcgcggctg cctccgcgct cgcccgggct cgcgctgggcg      60
```

```
ctgccgctgc tgctgctgct gctgcgcctg ggccagatcc tgtgcgcagg tggcacccct    120
agtccaattc ctgacccttc agtagcaact gttgccacag gggaaaatgg cataacgcag    180
atcagcagta cagcagaatc ctttcataaa cagaatggaa ctggaacacc tcaggtggaa    240
acaaacacca gtgaggatgg tgaaagctct ggagccaacg atagtttaag aacacctgaa    300
caaggatcta atgggactga tggggcatct caaaaaactc ccagtagcac tgggcccagt    360
cctgtgtttg acattaaagc tgtttccatc agtccaacca atgtgatctt aacttggaaa    420
agtaatgaca cagctgcttc tgagtacaag tatgtagtaa agcataagat ggaaaatgag    480
aagacaatta ctgttgtgca tcaaccatgg tgtaacatca caggcttacg tccagcgact    540
tcatatgtat tctccatcac tccaggaata ggcaatgaga cttggggaga tcccagagtc    600
ataaaagtca tcacagagcc gatcccagtt tctgatctcc gtgttgccct cacgggtgtg    660
aggaaggctg ctctctcctg gagcaatggc aatggcactg cctcctgccg ggttcttctt    720
gaaagcattg gaagccatga ggagttgact caagactcaa gacttcaggt caatatctcg    780
ggcctgaagc caggggttca atacaacatc aacccgtatc ttctacaatc aaataagaca    840
aagggagacc ccttgggcac agaaggtggc ttggatgcca gcaatacaga gagaagccgg    900
gcagggagcc ccaccgcccc tgtgcatgat gagtccctcg tgggacctgt ggacccatcc    960
tccggccagc agtcccgaga cacggaagtc ctgcttgtcg ggttagagcc tggcacccga   1020
tacaatgcca ccgtttattc ccaagcagcg aatggcacag aaggacagcc ccaggccata   1080
gagttcagga caaatgctat tcaggttttt gacgtcaccg ctgtgaacat cagtgccaca   1140
agcctgaccc tgatctggaa agtcagcgat aacgagtcgt catctaacta tacctacaag   1200
atacatgtgg cggggggagac agattcttcc aatctcaacg tcagtgagcc tcgcgctgtc   1260
atccccggac tccgctccag caccttctac aacatcacag tgtgtcctgt cctaggtgac   1320
atcgagggca cgccgggctt cctccaagtg cacaccccccc ctgttccagt ttctgacttc   1380
cgagtgacag tggtcagcac gacggagatc ggcttagcat ggagcagcca tgatgcagaa   1440
tcatttcaga tgcatatcac acaggaggga gctggcaatt ctcgggtaga aataaccacc   1500
aaccaaagta ttatcattgg tggcttgttc cctggaacca agtattgctt tgaaatagtt   1560
ccaaaaggac caaatgggac tgaaggggca tctcggacag tttgcaatag aactggatga   1620
```

<210> SEQ ID NO 19
<211> LENGTH: 418
<212> TYPE: PRT
<213> ORGANISM: Homo sapiens

<400> SEQUENCE: 19

Met Gln Ala Leu Val Leu Leu Cys Ile Gly Ala Leu Leu Gly His
1               5                   10                  15

Ser Ser Cys Gln Asn Pro Ala Ser Pro Glu Glu Gly Ser Pro Asp
                20                  25                  30

Pro Asp Ser Thr Gly Ala Leu Val Glu Glu Asp Pro Phe Phe Lys
                35                  40                  45

Val Pro Val Asn Lys Leu Ala Ala Ala Val Ser Asn Phe Gly Tyr Asp
        50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
             100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 20
<211> LENGTH: 699
<212> TYPE: PRT
<213> ORGANISM: Homo sapiens

<400> SEQUENCE: 20

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
                20                  25                  30

Ser Pro Gly Tyr Pro Asp Ser Tyr Pro Ser Asp Ser Glu Val Thr Trp
            35                  40                  45

```
Asn Ile Thr Val Pro Asp Gly Phe Arg Ile Lys Leu Tyr Phe Met His
 50                  55                  60

Phe Asn Leu Glu Ser Ser Tyr Leu Cys Glu Tyr Asp Tyr Val Lys Val
 65                  70                  75                  80

Glu Thr Glu Asp Gln Val Leu Ala Thr Phe Cys Gly Arg Glu Thr Thr
                 85                  90                  95

Asp Thr Glu Gln Thr Pro Gly Gln Glu Val Leu Ser Pro Gly Ser
                100                 105                 110

Phe Met Ser Ile Thr Phe Arg Ser Asp Phe Ser Asn Glu Glu Arg Phe
            115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
                180                 185                 190

Arg Thr Gly Val Ile Thr Ser Pro Asp Phe Pro Asn Pro Tyr Pro Lys
            195                 200                 205

Ser Ser Glu Cys Leu Tyr Thr Ile Glu Leu Glu Gly Phe Met Val
210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
            275                 280                 285

Gly Trp Arg Leu Ser Tyr Arg Ala Ala Gly Asn Glu Cys Pro Glu Leu
290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
    355                 360                 365

Ala Pro Gly Glu Leu Glu His Gly Leu Ile Thr Phe Ser Thr Arg Asn
370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Val Cys Gly Leu Pro Lys Phe Ser Arg Lys Leu Met Ala Arg
            435                 440                 445

Ile Phe Asn Gly Arg Pro Ala Gln Lys Gly Thr Thr Pro Trp Ile Ala
450                 455                 460

Met Leu Ser His Leu Asn Gly Gln Pro Phe Cys Gly Gly Ser Leu Leu
```

```
                465                 470                 475                 480
Gly Ser Ser Trp Ile Val Thr Ala Ala His Cys Leu His Gln Ser Leu
                    485                 490                 495
Asp Pro Glu Asp Pro Thr Leu Arg Asp Ser Asp Leu Leu Ser Pro Ser
                500                 505                 510
Asp Phe Lys Ile Ile Leu Gly Lys His Trp Arg Leu Arg Ser Asp Glu
            515                 520                 525
Asn Glu Gln His Leu Gly Val Lys His Thr Thr Leu His Pro Gln Tyr
        530                 535                 540
Asp Pro Asn Thr Phe Glu Asn Asp Val Ala Leu Val Glu Leu Leu Glu
545                 550                 555                 560
Ser Pro Val Leu Asn Ala Phe Val Met Pro Ile Cys Leu Pro Glu Gly
                565                 570                 575
Pro Gln Gln Glu Gly Ala Met Val Ile Val Ser Gly Trp Gly Lys Gln
                580                 585                 590
Phe Leu Gln Arg Phe Pro Glu Thr Leu Met Glu Ile Glu Ile Pro Ile
            595                 600                 605
Val Asp His Ser Thr Cys Gln Lys Ala Tyr Ala Pro Leu Lys Lys Lys
        610                 615                 620
Val Thr Arg Asp Met Ile Cys Ala Gly Glu Lys Gly Gly Lys Asp
625                 630                 635                 640
Ala Cys Ala Gly Asp Ser Gly Gly Pro Met Val Thr Leu Asn Arg Glu
                645                 650                 655
Arg Gly Gln Trp Tyr Leu Val Gly Thr Val Ser Trp Gly Asp Asp Cys
                660                 665                 670
Gly Lys Lys Asp Arg Tyr Gly Val Tyr Ser Tyr Ile His His Asn Lys
            675                 680                 685
Asp Trp Ile Gln Arg Val Thr Gly Val Arg Asn
        690                 695

<210> SEQ ID NO 21
<211> LENGTH: 722
<212> TYPE: PRT
<213> ORGANISM: Homo sapiens

<400> SEQUENCE: 21

Met Ala Pro His Arg Pro Ala Pro Ala Leu Leu Cys Ala Leu Ser Leu
1               5                   10                  15
Ala Leu Cys Ala Leu Ser Leu Pro Val Arg Ala Ala Thr Ala Ser Arg
            20                  25                  30
Gly Ala Ser Gln Ala Gly Ala Pro Gln Gly Arg Val Pro Glu Ala Arg
        35                  40                  45
Pro Asn Ser Met Val Val Glu His Pro Glu Phe Leu Lys Ala Gly Lys
    50                  55                  60
Glu Pro Gly Leu Gln Ile Trp Arg Val Glu Lys Phe Asp Leu Val Pro
65                  70                  75                  80
Val Pro Thr Asn Leu Tyr Gly Asp Phe Phe Thr Gly Asp Ala Tyr Val
                85                  90                  95
Ile Leu Lys Thr Val Gln Leu Arg Asn Gly Asn Leu Gln Tyr Asp Leu
            100                 105                 110
His Tyr Trp Leu Gly Asn Glu Cys Ser Gln Asp Glu Ser Gly Ala Ala
        115                 120                 125
Ala Ile Phe Thr Val Gln Leu Asp Asp Tyr Leu Asn Gly Arg Ala Val
        130                 135                 140
```

```
Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Gln Arg Leu Phe Gln Val
            180                 185                 190

Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
        210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
            275                 280                 285

Lys Glu Asp Ala Ala Asn Arg Lys Leu Ala Lys Leu Thr Ala Ser Asp
290                 295                 300

Phe Ile Thr Lys Met Asp Tyr Pro Lys Gln Thr Gln Val Ser Val Leu
305                 310                 315                 320

Pro Glu Gly Gly Glu Thr Pro Leu Phe Lys Gln Phe Phe Lys Asn Trp
                325                 330                 335

Arg Asp Pro Asp Gln Thr Asp Gly Leu Gly Leu Ser Tyr Leu Ser Ser
                340                 345                 350

His Ile Ala Asn Val Glu Arg Val Pro Phe Asp Ala Ala Thr Leu His
            355                 360                 365

Thr Ser Thr Ala Met Ala Ala Gln His Gly Met Asp Asp Asp Gly Thr
        370                 375                 380

Gly Gln Lys Gln Ile Trp Arg Ile Glu Gly Ser Asn Lys Val Pro Val
385                 390                 395                 400

Asp Pro Ala Thr Tyr Gly Gln Phe Tyr Gly Gly Asp Ser Tyr Ile Ile
                405                 410                 415

Leu Tyr Asn Tyr Arg His Gly Gly Arg Gln Gly Gln Ile Ile Tyr Asn
            420                 425                 430

Trp Gln Gly Ala Gln Ser Thr Gln Asp Glu Val Ala Ala Ser Ala Ile
        435                 440                 445

Leu Thr Ala Gln Leu Asp Glu Glu Leu Gly Gly Thr Pro Val Gln Ser
        450                 455                 460

Arg Val Val Gln Gly Lys Glu Pro Ala His Leu Met Ser Leu Phe Gly
465                 470                 475                 480

Gly Lys Pro Met Ile Ile Tyr Lys Gly Gly Thr Ser Arg Glu Gly Gly
                485                 490                 495

Gln Thr Ala Pro Ala Ser Thr Arg Leu Phe Gln Val Arg Ala Asn Ser
                500                 505                 510

Ala Gly Ala Thr Arg Ala Val Glu Val Leu Pro Lys Ala Gly Ala Leu
            515                 520                 525

Asn Ser Asn Asp Ala Phe Val Leu Lys Thr Pro Ser Ala Ala Tyr Leu
            530                 535                 540

Trp Val Gly Thr Gly Ala Ser Glu Ala Glu Lys Thr Gly Ala Gln Glu
545                 550                 555                 560

Leu Leu Arg Val Leu Arg Ala Gln Pro Val Gln Val Ala Glu Gly Ser
```

```
                    565                 570                 575

Glu Pro Asp Gly Phe Trp Glu Ala Leu Gly Gly Lys Ala Ala Tyr Arg
            580                 585                 590

Thr Ser Pro Arg Leu Lys Asp Lys Met Asp Ala His Pro Pro Arg
        595                 600                 605

Leu Phe Ala Cys Ser Asn Lys Ile Gly Arg Phe Val Ile Glu Glu Val
    610                 615                 620

Pro Gly Glu Leu Met Gln Glu Asp Leu Ala Thr Asp Val Met Leu
625                 630                 635                 640

Leu Asp Thr Trp Asp Gln Val Phe Val Trp Val Gly Lys Asp Ser Gln
                645                 650                 655

Glu Glu Glu Lys Thr Glu Ala Leu Thr Ser Ala Lys Arg Tyr Ile Glu
            660                 665                 670

Thr Asp Pro Ala Asn Arg Asp Arg Arg Thr Pro Ile Thr Val Val Lys
        675                 680                 685

Gln Gly Phe Glu Pro Pro Ser Phe Val Gly Trp Phe Leu Gly Trp Asp
    690                 695                 700

Asp Asp Tyr Trp Ser Val Asp Pro Leu Asp Arg Ala Met Ala Glu Leu
705                 710                 715                 720

Ala Ala

<210> SEQ ID NO 22
<211> LENGTH: 338
<212> TYPE: PRT
<213> ORGANISM: Homo sapiens

<400> SEQUENCE: 22

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
            20                  25                  30

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
    50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
    130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
```

```
                    210                 215                 220
Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
                260                 265                 270

Asn Glu Asn Leu Glu Asn Tyr Tyr Leu Glu Val Asn Gln Leu Glu Lys
                275                 280                 285

Phe Asp Ile Lys Ser Phe Cys Lys Ile Leu Gly Pro Leu Ser Tyr Ser
                290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 23
<211> LENGTH: 1156
<212> TYPE: PRT
<213> ORGANISM: Homo sapiens

<400> SEQUENCE: 23

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
                100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
                180                 185                 190

Ala Ser Val Ile Cys Arg Gln Leu Glu Cys Gly Ser Ala Val Ser Phe
            195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
```

-continued

```
                245                 250                 255
Ile Cys Ser Lys Gly Ala Asp Leu Ser Leu Arg Leu Val Asp Gly Val
            260                 265                 270
Thr Glu Cys Ser Gly Arg Leu Glu Val Arg Phe Gln Gly Glu Trp Gly
            275                 280                 285
Thr Ile Cys Asp Asp Gly Trp Asp Ser Tyr Asp Ala Ala Val Ala Cys
            290                 295                 300
Lys Gln Leu Gly Cys Pro Thr Ala Val Thr Ala Ile Gly Arg Val Asn
305                 310                 315                 320
Ala Ser Lys Gly Phe Gly His Ile Trp Leu Asp Ser Val Ser Cys Gln
                325                 330                 335
Gly His Glu Pro Ala Ile Trp Gln Cys Lys His His Glu Trp Gly Lys
            340                 345                 350
His Tyr Cys Asn His Asn Glu Asp Ala Gly Val Thr Cys Ser Asp Gly
            355                 360                 365
Ser Asp Leu Glu Leu Arg Leu Arg Gly Gly Ser Arg Cys Ala Gly
            370                 375                 380
Thr Val Glu Val Glu Ile Gln Arg Leu Leu Gly Lys Val Cys Asp Arg
385                 390                 395                 400
Gly Trp Gly Leu Lys Glu Ala Asp Val Val Cys Arg Gln Leu Gly Cys
                405                 410                 415
Gly Ser Ala Leu Lys Thr Ser Tyr Gln Val Tyr Ser Lys Ile Gln Ala
            420                 425                 430
Thr Asn Thr Trp Leu Phe Leu Ser Ser Cys Asn Gly Asn Glu Thr Ser
            435                 440                 445
Leu Trp Asp Cys Lys Asn Trp Gln Trp Gly Gly Leu Thr Cys Asp His
450                 455                 460
Tyr Glu Glu Ala Lys Ile Thr Cys Ser Ala His Arg Glu Pro Arg Leu
465                 470                 475                 480
Val Gly Gly Asp Ile Pro Cys Ser Gly Arg Val Glu Val Lys His Gly
                485                 490                 495
Asp Thr Trp Gly Ser Ile Cys Asp Ser Asp Phe Ser Leu Glu Ala Ala
            500                 505                 510
Ser Val Leu Cys Arg Glu Leu Gln Cys Gly Thr Val Val Ser Ile Leu
            515                 520                 525
Gly Gly Ala His Phe Gly Glu Gly Asn Gly Gln Ile Trp Ala Glu Glu
            530                 535                 540
Phe Gln Cys Glu Gly His Glu Ser His Leu Ser Leu Cys Pro Val Ala
545                 550                 555                 560
Pro Arg Pro Glu Gly Thr Cys Ser His Ser Arg Asp Val Gly Val Val
                565                 570                 575
Cys Ser Arg Tyr Thr Glu Ile Arg Leu Val Asn Gly Lys Thr Pro Cys
            580                 585                 590
Glu Gly Arg Val Glu Leu Lys Thr Leu Gly Ala Trp Gly Ser Leu Cys
            595                 600                 605
Asn Ser His Trp Asp Ile Glu Asp Ala His Val Leu Cys Gln Gln Leu
            610                 615                 620
Lys Cys Gly Val Ala Leu Ser Thr Pro Gly Gly Ala Arg Phe Gly Lys
625                 630                 635                 640
Gly Asn Gly Gln Ile Trp Arg His Met Phe His Cys Thr Gly Thr Glu
                645                 650                 655
Gln His Met Gly Asp Cys Pro Val Thr Ala Leu Gly Ala Ser Leu Cys
            660                 665                 670
```

```
Pro Ser Glu Gln Val Ala Ser Val Ile Cys Ser Gly Asn Gln Ser Gln
    675                 680                 685

Thr Leu Ser Ser Cys Asn Ser Ser Leu Gly Pro Thr Arg Pro Thr
690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
                740                 745                 750

Ala His Val Val Cys Arg Gln Leu Gly Cys Gly Glu Ala Ile Asn Ala
                755                 760                 765

Thr Gly Ser Ala His Phe Gly Glu Gly Thr Gly Pro Ile Trp Leu Asp
770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
                820                 825                 830

Glu Ala Cys Ala Gly Arg Leu Glu Val Phe Tyr Asn Gly Ala Trp Gly
                835                 840                 845

Thr Val Gly Lys Ser Ser Met Ser Glu Thr Thr Val Gly Val Val Cys
850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
                900                 905                 910

Arg Leu Ala Ser Pro Ser Glu Glu Thr Trp Ile Thr Cys Asp Asn Lys
                915                 920                 925

Ile Arg Leu Gln Glu Gly Pro Thr Ser Cys Ser Gly Arg Val Glu Ile
930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
                980                 985                 990

Leu Asn Glu Val Lys Cys Lys Gly Asn Glu Ser Ser Leu Trp Asp Cys
                995                 1000                1005

Pro Ala Arg Arg Trp Gly His Ser Glu Cys Gly His Lys Glu Asp
    1010                1015                1020

Ala Ala Val Asn Cys Thr Asp Ile Ser Val Gln Lys Thr Pro Gln
    1025                1030                1035

Lys Ala Thr Thr Gly Arg Ser Arg Gln Ser Ser Phe Ile Ala
    1040                1045                1050

Val Gly Ile Leu Gly Val Val Leu Leu Ala Ile Phe Val Ala Leu
    1055                1060                1065

Phe Phe Leu Thr Lys Lys Arg Arg Gln Arg Gln Arg Leu Ala Val
    1070                1075                1080
```

```
Ser  Ser  Arg  Gly  Glu  Asn  Leu  Val  His  Gln  Ile  Gln  Tyr  Arg  Glu
    1085                1090                1095

Met  Asn  Ser  Cys  Leu  Asn  Ala  Asp  Asp  Leu  Asp  Leu  Met  Asn  Ser
    1100                1105                1110

Ser  Glu  Asn  Ser  His  Glu  Ser  Ala  Asp  Phe  Ser  Ala  Ala  Glu  Leu
    1115                1120                1125

Ile  Ser  Val  Ser  Lys  Phe  Leu  Pro  Ile  Ser  Gly  Met  Glu  Lys  Glu
    1130                1135                1140

Ala  Ile  Leu  Ser  His  Thr  Glu  Lys  Glu  Asn  Gly  Asn  Leu
    1145                1150                1155

<210> SEQ ID NO 24
<211> LENGTH: 1337
<212> TYPE: PRT
<213> ORGANISM: Homo sapiens

<400> SEQUENCE: 24

Met  Lys  Pro  Ala  Ala  Arg  Glu  Ala  Arg  Leu  Pro  Pro  Arg  Ser  Pro  Gly
  1                  5                   10                  15

Leu  Arg  Trp  Ala  Leu  Pro  Leu  Leu  Leu  Leu  Leu  Arg  Leu  Gly  Gln
                    20                  25                  30

Ile  Leu  Cys  Ala  Gly  Gly  Thr  Pro  Ser  Pro  Ile  Pro  Asp  Pro  Ser  Val
             35                  40                  45

Ala  Thr  Val  Ala  Thr  Gly  Glu  Asn  Gly  Ile  Thr  Gln  Ile  Ser  Ser  Thr
 50                      55                  60

Ala  Glu  Ser  Phe  His  Lys  Gln  Asn  Gly  Thr  Gly  Thr  Pro  Gln  Val  Glu
 65                      70                  75                      80

Thr  Asn  Thr  Ser  Glu  Asp  Gly  Glu  Ser  Ser  Gly  Ala  Asn  Asp  Ser  Leu
                         85                  90                  95

Arg  Thr  Pro  Glu  Gln  Gly  Ser  Asn  Gly  Thr  Asp  Gly  Ala  Ser  Gln  Lys
                    100                 105                 110

Thr  Pro  Ser  Ser  Thr  Gly  Pro  Ser  Pro  Val  Phe  Asp  Ile  Lys  Ala  Val
                    115                 120                 125

Ser  Ile  Ser  Pro  Thr  Asn  Val  Ile  Leu  Thr  Trp  Lys  Ser  Asn  Asp  Thr
    130                 135                 140

Ala  Ala  Ser  Glu  Tyr  Lys  Tyr  Val  Val  Lys  His  Lys  Met  Glu  Asn  Glu
145                      150                 155                     160

Lys  Thr  Ile  Thr  Val  Val  His  Gln  Pro  Trp  Cys  Asn  Ile  Thr  Gly  Leu
                    165                 170                 175

Arg  Pro  Ala  Thr  Ser  Tyr  Val  Phe  Ser  Ile  Thr  Pro  Gly  Ile  Gly  Asn
                    180                 185                 190

Glu  Thr  Trp  Gly  Asp  Pro  Arg  Val  Ile  Lys  Val  Ile  Thr  Glu  Pro  Ile
                    195                 200                 205

Pro  Val  Ser  Asp  Leu  Arg  Val  Ala  Leu  Thr  Gly  Val  Arg  Lys  Ala  Ala
    210                 215                 220

Leu  Ser  Trp  Ser  Asn  Gly  Asn  Gly  Thr  Ala  Ser  Cys  Arg  Val  Leu  Leu
225                      230                 235                     240

Glu  Ser  Ile  Gly  Ser  His  Glu  Glu  Leu  Thr  Gln  Asp  Ser  Arg  Leu  Gln
                    245                 250                 255

Val  Asn  Ile  Ser  Gly  Leu  Lys  Pro  Gly  Val  Gln  Tyr  Asn  Ile  Asn  Pro
                    260                 265                 270

Tyr  Leu  Leu  Gln  Ser  Asn  Lys  Thr  Lys  Gly  Asp  Pro  Leu  Gly  Thr  Glu
                    275                 280                 285

Gly  Gly  Leu  Asp  Ala  Ser  Asn  Thr  Glu  Arg  Ser  Arg  Ala  Gly  Ser  Pro
    290                 295                 300
```

```
Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
            325                 330                 335

Pro Gly Thr Arg Tyr Asn Ala Thr Val Tyr Ser Gln Ala Ala Asn Gly
            340                 345                 350

Thr Glu Gly Gln Pro Gln Ala Ile Glu Phe Arg Thr Asn Ala Ile Gln
            355                 360                 365

Val Phe Asp Val Thr Ala Val Asn Ile Ser Ala Thr Ser Leu Thr Leu
        370                 375                 380

Ile Trp Lys Val Ser Asp Asn Glu Ser Ser Asn Tyr Thr Tyr Lys
385                 390                 395                 400

Ile His Val Ala Gly Glu Thr Asp Ser Ser Asn Leu Asn Val Ser Glu
                405                 410                 415

Pro Arg Ala Val Ile Pro Gly Leu Arg Ser Ser Thr Phe Tyr Asn Ile
            420                 425                 430

Thr Val Cys Pro Val Leu Gly Asp Ile Glu Gly Thr Pro Gly Phe Leu
        435                 440                 445

Gln Val His Thr Pro Pro Val Pro Val Ser Asp Phe Arg Val Thr Val
        450                 455                 460

Val Ser Thr Thr Glu Ile Gly Leu Ala Trp Ser Ser His Asp Ala Glu
465                 470                 475                 480

Ser Phe Gln Met His Ile Thr Gln Glu Gly Ala Gly Asn Ser Arg Val
                485                 490                 495

Glu Ile Thr Thr Asn Gln Ser Ile Ile Gly Gly Leu Phe Pro Gly
            500                 505                 510

Thr Lys Tyr Cys Phe Glu Ile Val Pro Lys Gly Pro Asn Gly Thr Glu
            515                 520                 525

Gly Ala Ser Arg Thr Val Cys Asn Arg Thr Val Pro Ser Ala Val Phe
        530                 535                 540

Asp Ile His Val Val Tyr Val Thr Thr Thr Glu Met Trp Leu Asp Trp
545                 550                 555                 560

Lys Ser Pro Asp Gly Ala Ser Glu Tyr Val Tyr His Leu Val Ile Glu
                565                 570                 575

Ser Lys His Gly Ser Asn His Thr Ser Thr Tyr Asp Lys Ala Ile Thr
            580                 585                 590

Leu Gln Gly Leu Ile Pro Gly Thr Leu Tyr Asn Ile Thr Ile Ser Pro
        595                 600                 605

Glu Val Asp His Val Trp Gly Asp Pro Asn Ser Thr Ala Gln Tyr Thr
610                 615                 620

Arg Pro Ser Asn Val Ser Asn Ile Asp Val Ser Thr Asn Thr Thr Ala
625                 630                 635                 640

Ala Thr Leu Ser Trp Gln Asn Phe Asp Asp Ala Ser Pro Thr Tyr Ser
                645                 650                 655

Tyr Cys Leu Leu Ile Glu Lys Ala Gly Asn Ser Ser Asn Ala Thr Gln
            660                 665                 670

Val Val Thr Asp Ile Gly Ile Thr Asp Ala Thr Val Thr Glu Leu Ile
        675                 680                 685

Pro Gly Ser Ser Tyr Thr Val Glu Ile Phe Ala Gln Val Gly Asp Gly
        690                 695                 700

Ile Lys Ser Leu Glu Pro Gly Arg Lys Ser Phe Cys Thr Asp Pro Ala
705                 710                 715                 720
```

-continued

```
Ser Met Ala Ser Phe Asp Cys Glu Val Val Pro Lys Glu Pro Ala Leu
            725                 730                 735

Val Leu Lys Trp Thr Cys Pro Pro Gly Ala Asn Ala Gly Phe Glu Leu
            740                 745                 750

Glu Val Ser Ser Gly Ala Trp Asn Asn Ala Thr His Leu Glu Ser Cys
            755                 760             765

Ser Ser Glu Asn Gly Thr Glu Tyr Arg Thr Glu Val Thr Tyr Leu Asn
            770                 775                 780

Phe Ser Thr Ser Tyr Asn Ile Ser Ile Thr Thr Val Ser Cys Gly Lys
785                 790                 795                 800

Met Ala Ala Pro Thr Arg Asn Thr Cys Thr Thr Gly Ile Thr Asp Pro
                805                 810                 815

Pro Pro Pro Asp Gly Ser Pro Asn Ile Thr Ser Val Ser His Asn Ser
            820                 825                 830

Val Lys Val Lys Phe Ser Gly Phe Glu Ala Ser His Gly Pro Ile Lys
            835                 840                 845

Ala Tyr Ala Val Ile Leu Thr Thr Gly Glu Ala Gly His Pro Ser Ala
            850                 855                 860

Asp Val Leu Lys Tyr Thr Tyr Glu Asp Phe Lys Lys Gly Ala Ser Asp
865                 870                 875                 880

Thr Tyr Val Thr Tyr Leu Ile Arg Thr Glu Glu Lys Gly Arg Ser Gln
                885                 890                 895

Ser Leu Ser Glu Val Leu Lys Tyr Glu Ile Asp Val Gly Asn Glu Ser
            900                 905                 910

Thr Thr Leu Gly Tyr Tyr Asn Gly Lys Leu Glu Pro Leu Gly Ser Tyr
            915                 920                 925

Arg Ala Cys Val Ala Gly Phe Thr Asn Ile Thr Phe His Pro Gln Asn
            930                 935                 940

Lys Gly Leu Ile Asp Gly Ala Glu Ser Tyr Val Ser Phe Ser Arg Tyr
945                 950                 955                 960

Ser Asp Ala Val Ser Leu Pro Gln Asp Pro Gly Val Ile Cys Gly Ala
                965                 970                 975

Val Phe Gly Cys Ile Phe Gly Ala Leu Val Ile Val Thr Val Gly Gly
            980                 985                 990

Phe Ile Phe Trp Arg Lys Lys Arg  Lys Asp Ala Lys Asn  Asn Glu Val
            995                 1000                1005

Ser Phe  Ser Gln Ile Lys Pro  Lys Lys Ser Lys Leu  Ile Arg Val
            1010                1015                1020

Glu Asn  Phe Glu Ala Tyr Phe  Lys Lys Gln Gln Ala  Asp Ser Asn
            1025                1030                1035

Cys Gly  Phe Ala Glu Glu Tyr  Glu Asp Leu Lys Leu  Val Gly Ile
            1040                1045                1050

Ser Gln  Pro Lys Tyr Ala Ala  Glu Leu Ala Glu Asn  Arg Gly Lys
            1055                1060                1065

Asn Arg  Tyr Asn Asn Val Leu  Pro Tyr Asp Ile Ser  Arg Val Lys
            1070                1075                1080

Leu Ser  Val Gln Thr His Ser  Thr Asp Asp Tyr Ile  Asn Ala Asn
            1085                1090                1095

Tyr Met  Pro Gly Tyr His Ser  Lys Lys Asp Phe Ile  Ala Thr Gln
            1100                1105                1110

Gly Pro  Leu Pro Asn Thr Leu  Lys Asp Phe Trp Arg  Met Val Trp
            1115                1120                1125

Glu Lys  Asn Val Tyr Ala Ile  Ile Met Leu Thr Lys  Cys Val Glu
```

-continued

```
                1130                1135                1140

Gln Gly Arg Thr Lys Cys Glu Glu Tyr Trp Pro Ser Lys Gln Ala
        1145                1150                1155

Gln Asp Tyr Gly Asp Ile Thr Val Ala Met Thr Ser Glu Ile Val
        1160                1165                1170

Leu Pro Glu Trp Thr Ile Arg Asp Phe Thr Val Lys Asn Ile Gln
        1175                1180                1185

Thr Ser Glu Ser His Pro Leu Arg Gln Phe His Phe Thr Ser Trp
        1190                1195                1200

Pro Asp His Gly Val Pro Asp Thr Thr Asp Leu Leu Ile Asn Phe
        1205                1210                1215

Arg Tyr Leu Val Arg Asp Tyr Met Lys Gln Ser Pro Pro Glu Ser
        1220                1225                1230

Pro Ile Leu Val His Cys Ser Ala Gly Val Gly Arg Thr Gly Thr
        1235                1240                1245

Phe Ile Ala Ile Asp Arg Leu Ile Tyr Gln Ile Glu Asn Glu Asn
        1250                1255                1260

Thr Val Asp Val Tyr Gly Ile Val Tyr Asp Leu Arg Met His Arg
        1265                1270                1275

Pro Leu Met Val Gln Thr Glu Asp Gln Tyr Val Phe Leu Asn Gln
        1280                1285                1290

Cys Val Leu Asp Ile Val Arg Ser Gln Lys Asp Ser Lys Val Asp
        1295                1300                1305

Leu Ile Tyr Gln Asn Thr Thr Ala Met Thr Ile Tyr Glu Asn Leu
        1310                1315                1320

Ala Pro Val Thr Thr Phe Gly Lys Thr Asn Gly Tyr Ile Ala
        1325                1330                1335

<210> SEQ ID NO 25
<211> LENGTH: 8
<212> TYPE: PRT
<213> ORGANISM: Homo sapiens

<400> SEQUENCE: 25

Ala Leu Gln Ala Ser Ala Leu Lys
1               5

<210> SEQ ID NO 26
<211> LENGTH: 9
<212> TYPE: PRT
<213> ORGANISM: Homo sapiens

<400> SEQUENCE: 26

Ala Val Gly Leu Ala Gly Thr Phe Arg
1               5

<210> SEQ ID NO 27
<211> LENGTH: 9
<212> TYPE: PRT
<213> ORGANISM: Homo sapiens

<400> SEQUENCE: 27

Gly Phe Leu Leu Leu Ala Ser Leu Arg
1               5

<210> SEQ ID NO 28
<211> LENGTH: 15
<212> TYPE: PRT
<213> ORGANISM: Homo sapiens
```

-continued

```
<400> SEQUENCE: 28

Leu Gly Gly Pro Glu Ala Gly Leu Gly Glu Tyr Leu Phe Glu Arg
1               5                   10                  15

<210> SEQ ID NO 29
<211> LENGTH: 6
<212> TYPE: PRT
<213> ORGANISM: Homo sapiens

<400> SEQUENCE: 29

Val Glu Ile Phe Tyr Arg
1               5
```